(12) United States Patent
Raitano et al.

(10) Patent No.: US 6,790,631 B1
(45) Date of Patent: Sep. 14, 2004

(54) G PROTEIN-COUPLED RECEPTOR UP-REGULATED IN PROSTATE CANCER AND USES THEREOF

(75) Inventors: Arthur B. Raitano, Los Angeles, CA (US); Daniel E. H. Afar, Brisbane, CA (US); Aya Jakobovits, Beverly Hills, CA (US); Mary Faris, Los Angeles, CA (US); Rene S. Hubert, Los Angeles, CA (US); Steve Chappell Mitchell, Santa Monica, CA (US); Douglas C. Saffran, Los Angeles, CA (US)

(73) Assignee: Agensys, Inc., Santa Monica, CA (US)

( * ) Notice: Subject to any disclaimer, the term of this patent is extended or adjusted under 35 U.S.C. 154(b) by 0 days.

(21) Appl. No.: 09/680,728

(22) Filed: Oct. 5, 2000

Related U.S. Application Data

(60) Provisional application No. 60/157,902, filed on Oct. 5, 1999.

(51) Int. Cl.$^7$ ............................................. G01M 33/53
(52) U.S. Cl. ...................... 435/7.23; 435/7.1; 530/350; 530/387.1; 424/185.1
(58) Field of Search ............................... 435/7.1, 7.23; 530/350, 387.1; 424/185.1

(56) References Cited

U.S. PATENT DOCUMENTS

| 5,756,309 A | 5/1998 | Soppet et al. ............... 435/69.1 |
| 2002/0022248 A1 | 2/2002 | Xu et al. .................... 435/69.1 |

FOREIGN PATENT DOCUMENTS

| GB | 2211504 | 7/1989 |
| WO | 00/04149 | 1/1900 |
| WO | 00/20590 | 4/1900 |
| WO | 96/39435 | 12/1996 |
| WO | 99/06550 | 2/1999 |

OTHER PUBLICATIONS

Roitt et al, 1988, Immunology, 4th ed, Mosby, London, pp. 7.7–7.8.*
Holmes. Exp. Opin.Invest. Drugs, 2001, 10(3):511–519.*
Herbert et al. The Dictionary of Immunology, Academic Press, 4th edition, 1995, p. 58.*
Greenspan et al. 1Nature Biotechnology 7:936–937 (1999).*
Fu et al EMBOJ. 15: 4392–4401. 1996.*
Burgers, J cells. Biol. 11: 2129–2138, 1990.*
Rampsrch Granli Reports, pp. 2–5, earli, 2002.*
Lazar, Mol. Cell Biol. 8P 1297–1252, 1988.*
Tao J. Immunol. 143(8): 2595–2601, 1989.*
Gillies Human Antibod., Hybudonas 1(1): 47–54, 1990.*
Harrison, P.R. Immunol. Series, 49: 411–64, 1990.*
Maruatis et al. (Eds). Mol. Cloning., Cold Spring Harbor Lab, Cold Spring Harbor, p. 17.31, 1989.*
Jansen, M. Pediatric Res. 37(6): 681–686, 1995.*
Alberts, Mol. Biol. Cell, 3rd ed, p. 465, 1994.*
Shantz, Mol. J. Biochem. Cell Biol. 31: 107–122, 1999.*
McClean, Eur. J. Cancer, 29A: 2243–2248, 1993.*
Hubert et al., Proc. Natl. Acad. Sci. USA (1999) 96(25):14523–14528.
Klein et al., Nat. Med. (1997) 3:402.
Pinto et al., Clin. Cancer Res. (1996) 2(9):1445–1451.
Reiter et al., Proc. Natl. Acad. Sci. USA (1998) 95:1735.
Su et al., Proc. Natl. Acad. Sci. USA (1996) 93:7252.
EMBL Sequence Accession No. AF101565, Jan. 29, 1999, Nov. 8, 2000.
NAGENESEQ, EMBI, Sequence Accession No. X40518, Jun. 18, 1999 (first entry).
EMBL Sequence Accession No. A06681, Geg Geneseq D, Jun. 13, 2000 (first entry).
H.O. Sjogren, "Therapeutic immunization against cancer antigens using genetically engineered cells," Immunotechnology, 1997, 3(3):161–172.
G. Bepler et al., "A 1,4–Mb high resolution physical map and contig of chromosome segment 11p13.3 and genes in the JOH11A metastasis suppressor region," *Genomics* 1999, 55(2) 164–175.
Birnbaumer, Cell (1992) 71:1069.
Craft et al., Cancer Res. (1999 59:5030–5036.
Evans et al., Am. J. Obstet. Gynecol. (1994) 171(4): 1055–1057.
Greulich and Erikson, J. Biol. Chem. (1998) 273:13280.
Lai et al., Clin. Cancer Res. (2000) 6(8):3172–3176.
Liebmann and Bohmer, Curr. Med. Chem. (2000) 7:911.
Malnic et al., Cell (1999) 96:713.
Maudsley et al., J. Biol. Chem. (2000) 275:9572.
Muller et al., MCB (1991) 11:1785.
Oya and Schulz, Br. J. Cancer (2000) 83(5):626–631.
Raming et al., Nature (1993) 361:353.
Raming et al., Receptor (1998) Receptor Channels 6:141.
Walter et al., Nat. Genetics (1994) 7:22.
Welch et al., Int. J. Cancer (1989) 43:449–457.

\* cited by examiner

*Primary Examiner*—Susan Ungar
*Assistant Examiner*—Minh-Tam Davis
(74) *Attorney, Agent, or Firm*—Morrison & Foerster LLP

(57) ABSTRACT

A novel gene (designated PHOR-1) that is highly over-expressed in prostate and other cancers and its encoded protein are described. PHOR-1 is a G protein-coupled receptor with homology to receptors involved in olfaction. PHOR-1 in normal human tissues is restricted to prostate, and this gene is highly over-expressed in prostate cancer as well as in cancers of the kidney, uterus, cervix, stomach and rectum. Consequently, PHOR-1 provides a diagnostic and/or therapeutic target for prostate cancer.

3 Claims, 25 Drawing Sheets

FIG. 1A

```
            9              18             27             36             45             54
5' CAG AGA GGC TGT ATT TCA GTG CAG CCT GCC AGA CCT CTT CTG GAG GAA GAC TGG
   --- --- --- --- --- --- --- --- --- --- --- --- --- --- --- --- --- ---
               63             72             81             90             99            108
   ACA AAG GGG GTC ACA CAT TCC TTC CAT ACG GTT GAG CCT CTA CCT GCC TGG TGC
   --- --- --- --- --- --- --- --- --- --- --- --- --- --- --- --- --- ---
              117            126            135            144            153            162
   TGG TCA CAG TTC AGC TTC TTC ATG ATG GTG GAT CCC AAT GGC AAT GAA TCC AGT
   --- --- --- --- --- --- --- --- --- --- --- --- --- --- --- --- --- ---
                                   M   M   V   D   P   N   G   N   E   S   S
              171            180            189            198            207            216
   GCT ACA TAC TTC ATC CTA ATA GGC CTC CCT GGT TTA GAA GAG GCT CAG TTC TGG
   --- --- --- --- --- --- --- --- --- --- --- --- --- --- --- --- --- ---
    A   T   Y   F   I   L   I   G   L   P   G   L   E   E   A   Q   F   W
              225            234            243            252            261            270
   TTG GCC TTC CCA TTG TGC TCC CTC TAC CTT ATT GCT GTG CTA GGT AAC TTG ACA
   --- --- --- --- --- --- --- --- --- --- --- --- --- --- --- --- --- ---
   |L   A   F   P   L   C   S   L   Y   L   I   A   V   L   G   N   L   T|
              279            288            297            306            315            324
   ATC ATC TAC ATT GTG CGG ACT GAG CAC AGC CTG CAT GAG CCC ATG TAT ATA TTT
   --- --- --- --- --- --- --- --- --- --- --- --- --- --- --- --- --- ---
   |I   I   Y   I   V|  R   T   E   H   S   L   H   E   P   M   Y  |I   F|
              333            342            351            360            369            378
   CTT TGC ATG CTT TCA GGC ATT GAC ATC CTC ATC TCC ACC TCA TCC ATG CCC AAA
   --- --- --- --- --- --- --- --- --- --- --- --- --- --- --- --- --- ---
   |L   C   M   L   S   G   I   D   I   L   I   S   T   S   S   M   P   K|
              387            396            405            414            423            432
   ATG CTG GCC ATC TTC TGG TTC AAT TCC ACT ACC ATC CAG TTT GAT GCT TGT CTG
   --- --- --- --- --- --- --- --- --- --- --- --- --- --- --- --- --- ---
   |M   L   A|  I   F   W   F   N   S   T   T   I   Q   F   D   A   C  |L|
              441            450            459            468            477            486
   CTA CAG ATT TTT GCC ATC CAC TCC TTA TCT GGC ATG GAA TCC ACA GTG CTG CTG
   --- --- --- --- --- --- --- --- --- --- --- --- --- --- --- --- --- ---
   |L   Q   I   F   A   I   H   S   L   S   G   M   E   S   T   V   L   L|
              495            504            513            522            531            540
   GCC ATG GCT TTT GAC CGC TAT GTG GCC ATC TGT CAC CCA CTG CGC CAT.GCC ACA
   --- --- --- --- --- --- --- --- --- --- --- --- --- --- --- --- --- ---
   |A   M   A   F|  D   R   Y   V   A   I   C   H   P   L   R   H   A  |T|
              549            558            567            576            585            594
   GTA CTT ACG TTG CCT CGT GTC ACC AAA ATT GGT GTG GCT GCT GTG GTG CGG GGG
   --- --- --- --- --- --- --- --- --- --- --- --- --- --- --- --- --- ---
   |V   L   T   L   P   R   V   T   K   I   G   V   A   A   V   V   R   G|
              603            612            621            630            639            648
   GCT GCA CTG ATG GCA CCC CTT CCT GTC TTC ATC AAG CAG CTG CCC TTC TGC CGC
   --- --- --- --- --- --- --- --- --- --- --- --- --- --- --- --- --- ---
   |A   A   L   M|  A   P   L   P   V   F   I   K   Q   L   P   F   C   R
```

FIG. 1B

```
        657         666         675         684         693         702
TCC AAT ATC CTT TCC CAT TCC TAC TGC CTA CAC CAA GAT GTC ATG AAG CTG GCC
--- --- --- --- --- --- --- --- --- --- --- --- --- --- --- --- --- ---
 S   N   I   L   S   H   S   Y   C   L   H   Q   D   V   M   K   L   A 711         720         729         738         747         756
TGT GAT GAT ATC CGG GTC AAT GTC GTC TAT GGC CTT ATC GTC ATC ATC TCC GCC
--- --- --- --- --- --- --- --- --- --- --- --- --- --- --- --- --- ---
 C   D   D   I   R   V   N   V   V   Y   G   L  |I   V   I   I   S   A|

765         774         783         792         801         810
ATT GGC CTG GAC TCA CTT CTC ATC TCC TTC TCA TAT CTG CTT ATT CTT AAG ACT
--- --- --- --- --- --- --- --- --- --- --- --- --- --- --- --- --- ---
|I   G   L   D   S   L   L   I   S   F   S   Y   L   L   I   L   K|  T 819         828         837         846         855         864
GTG TTG GGC TTG ACA CGT GAA GCC CAG GCC AAG GCA TTT GGC ACT TGC GTC TCT
--- --- --- --- --- --- --- --- --- --- --- --- --- --- --- --- --- ---
 V   L   G   L   T   R   E   A   Q   A   K   A  |F   G   T   C   V   S|

873         882         891         900         909         918
CAT GTG TGT GCT GTG TTC ATA TTC TAT GTA CCT TTC ATT GGA TTG TCC ATG GTG
--- --- --- --- --- --- --- --- --- --- --- --- --- --- --- --- --- ---
|H   V   C   A   V   F   I   F   Y   V   P   F   I   G   L   S   M|  V 927         936         945         954         963         972
CAT CGC TTT AGC AAG CGG CGT GAC TCT CCG CTG CCC GTC ATC TTG GCC AAT ATC
--- --- --- --- --- --- --- --- --- --- --- --- --- --- --- --- --- ---
 H   R   F   S   K   R   R   D   S   P  |L   P   V   I   L   A   N   I|

981         990         999        1008        1017        1026
TAT CTG CTG GTT CCT CCT GTG CTC AAC CCA ATT GTC TAT GGA GTG AAG ACA AAG
--- --- --- --- --- --- --- --- --- --- --- --- --- --- --- --- --- ---
|Y   L   L   V   P   P   V   L   N   P   I   V   Y   G   V|  K   T   K 1035        1044        1053        1062        1071        1080
GAG ATT CGA CAG CGC ATC CTT CGA CTT TTC CAT GTG GCC ACA CAC GCT TCA GAG
--- --- --- --- --- --- --- --- --- --- --- --- --- --- --- --- --- ---
 E   I   R   Q   R   I   L   R   L   F   H   V   A   T   H   A   S   E 1089        1098        1107        1116        1125        1134
CCC TAG GTG TCA GTG ATC AAA CTT CTT TTC CAT TCA GAG TCC TCT GAT TCA GAT
--- --- --- --- --- --- --- --- --- --- --- --- --- --- --- --- --- ---
 P   *

1143        1152        1161        1170        1179        1188
TTT AAT GTT AAC ATT TTG GAA GAC AGT ATT CAG AAA AAA AAT TTC CTT AAT AAA
       1197        1206        1215        1224        1233        1242
AAA TAC AAC TCA GAT CCT TCA AAT ATG AAA CTG GTT GGG GAA TCT CCA TTT TTT
       1251        1260        1269        1278        1287        1296
CAA TAT TAT TTT CTT CTT TGT TTT CTT GCT ACA TAT AAT TAT TAA TAC CCT GAC
       1305        1314        1323        1332        1341        1350
TAG GTT GTG GTT GGA GGG TTA TTA CTT TTC ATT TTA CCA TGC AGT CCA AAT CTA
```

FIG. 1C

```
        1359        1368        1377        1386        1395        1404
AAC TGC TTC TAC TGA TGG TTT ACA GCA TTC TGA GAT AAG AAT GGT ACA TCT AGA
--- --- --- --- --- --- --- --- --- --- --- --- --- --- --- --- --- ---
        1413        1422        1431        1440        1449        1458
GAA CAT TTG CCA AAG GCC TAA GCA CGG CAA AGG AAA ATA AAC ACA GAA TAT AAT
--- --- --- --- --- --- --- --- --- --- --- --- --- --- --- --- --- ---
        1467        1476        1485        1494        1503        1512
AAA ATG AGA TAA TCT AGC TTA AAA CTA TAA CTT CCT CTT CAG AAC TCC AAA CCA
--- --- --- --- --- --- --- --- --- --- --- --- --- --- --- --- --- ---
        1521        1530        1539        1548        1557        1566
CAT TGG ATC TCA GAA AAA TGC TGT CTT CAA AAT GAC TTC TAC AGA GAA GAA ATA
--- --- --- --- --- --- --- --- --- --- --- --- --- --- --- --- --- ---
        1575        1584        1593        1602        1611        1620
ATT TTT CCT CTG GAC ACT AGC ACT TAA GGG GAA GAT TGG AAG TAA AGC CTT GAA
--- --- --- --- --- --- --- --- --- --- --- --- --- --- --- --- --- ---
        1629        1638        1647        1656        1665        1674
AAG AGT ACA TTT ACC TAC GTT AAT GAA AGT TGA CAC ACT GTT CTG AGA GTT TTC
--- --- --- --- --- --- --- --- --- --- --- --- --- --- --- --- --- ---
        1683        1692        1701        1710        1719        1728
ACA GCA TAT GGA CCC TGT TTT TCC TAT TTA ATT TTC TTA TCA ACC CTT TAA TTA
--- --- --- --- --- --- --- --- --- --- --- --- --- --- --- --- --- ---
        1737        1746        1755        1764        1773        1782
GGC AAA GAT ATT ATT AGT ACC CTC ATT GTA GCC ATG GGA AAA TTG ATG TTC AGT
--- --- --- --- --- --- --- --- --- --- --- --- --- --- --- --- --- ---
        1791        1800        1809        1818        1827        1836
GGG GAT CAG TGA ATT AAA TGG GGT CAT ACA AGT ATA AAA ATT AAA AAA AAA AAA
--- --- --- --- --- --- --- --- --- --- --- --- --- --- --- --- --- ---
        1845        1854        1863        1872        1881        1890
GAC TTC ATG CCC AAT CTC ATA TGA TGT GGA AGA ACT GTT AGA GAG ACC AAC AGG
--- --- --- --- --- --- --- --- --- --- --- --- --- --- --- --- --- ---
        1899        1908        1917        1926        1935        1944
GTA GTG GGT TAG AGA TTT CCA GAG TCT TAC ATT TTC TAG AGG AGG TAT TTA ATT
--- --- --- --- --- --- --- --- --- --- --- --- --- --- --- --- --- ---
        1953        1962        1971        1980        1989        1998
TCT TCT CAC TCA TCC AGT GTT GTA TTT AGG AAT TTC CTG GCA ACA GAA CTC ATG
--- --- --- --- --- --- --- --- --- --- --- --- --- --- --- --- --- ---
        2007        2016        2025        2034        2043        2052
GCT TTA ATC CCA CTA GCT ATT GCT TAT TGT CCT GGT CCA ATT GCC AAT TAC CTG
--- --- --- --- --- --- --- --- --- --- --- --- --- --- --- --- --- ---
        2061        2070        2079        2088        2097        2106
TGT CTT GGA AGA AGT GAT TTC TAG GTT CAC CAT TAT GGA AGA TTC TTA TTC AGA
--- --- --- --- --- --- --- --- --- --- --- --- --- --- --- --- --- ---
        2115        2124        2133        2142        2151        2160
AAG TCT GCA TAG GGC TTA TAG CAA GTT ATT TAT TTT TAA AAG TTC CAT AGG TGA
--- --- --- --- --- --- --- --- --- --- --- --- --- --- --- --- --- ---
        2169        2178        2187        2196        2205        2214
TTC TGA TAG GCA GTG AGG TTA GGG AGC CAC CAG TTA TGA TGG GAA GTA TGG AAT
--- --- --- --- --- --- --- --- --- --- --- --- --- --- --- --- --- ---
        2223        2232        2241        2250        2259        2268
GGC AGG TCT TGA AGA TAA CAT TGG CCT TTT GAG TGT GAC TCG TAG CTG GAA AGT
--- --- --- --- --- --- --- --- --- --- --- --- --- --- --- --- --- ---
        2277        2286        2295        2304        2313        2322
GAG GGA ATC TTC AGG ACC ATG CTT TAT TTG GGG CTT TGT GCA GTA TGG AAC AGG
--- --- --- --- --- --- --- --- --- --- --- --- --- --- --- --- --- ---
        2331        2340        2349        2358        2367        2376
GAC TTT GAG ACC AGG AAA GCA ATC TGA CTT AGG CAT GGG AAT CAG GCA TTT TTG
--- --- --- --- --- --- --- --- --- --- --- --- --- --- --- --- --- ---
```

FIG. 1D

```
     2385        2394        2403        2412        2421        2430
CTT CTG AGG GGC TAT TAC CAA GGG TTA ATA GGT TTC ATC TTC AAC AGG ATA TGA
--- --- --- --- --- --- --- --- --- --- --- --- --- --- --- --- --- ---
            2439        2448        2457        2466        2475        2484
CAA CAG TGT TAA CCA AGA AAC TCA AAT TAC AAA TAC TAA AAC ATG TGA TCA TAT
--- --- --- --- --- --- --- --- --- --- --- --- --- --- --- --- --- ---
            2493        2502        2511        2520        2529        2538
ATG TGG TAA GTT TCA TTT TCT TTT TCA ATC CTC AGG TTC CCT GAT ATG GAT TCC
--- --- --- --- --- --- --- --- --- --- --- --- --- --- --- --- --- ---
            2547        2556        2565        2574        2583        2592
TAT AAC ATG CTT TCA TCC CCT TTT GTA ATG GAT ATC ATA TTT GGA AAT GCC TAT
--- --- --- --- --- --- --- --- --- --- --- --- --- --- --- --- --- ---
            2601        2610        2619        2628        2637        2646
TTA ATA CTT GTA TTT GCT GCT GGA CTG TAA GCC CAT GAG GGC ACT GTT TAT TAT
--- --- --- --- --- --- --- --- --- --- --- --- --- --- --- --- --- ---
            2655        2664        2673        2682        2691        2700
TGA ATG TCA TCT CTG TTC ATC ATT GAC TGC TCT TTG CTC ATC ATT GAA TCC CCC
--- --- --- --- --- --- --- --- --- --- --- --- --- --- --- --- --- ---
            2709        2718        2727        2736        2745        2754
AGC AAA GTG CCT AGA ACA TAA TAG TGC TTA TGC TTG ACA CCG GTT ATT TTT CAT
--- --- --- --- --- --- --- --- --- --- --- --- --- --- --- --- --- ---
            2763        2772        2781        2790        2799        2808
CAA ACC TGA TTC CTT CTG TCC TGA ACA CAT AGC CAG GCA ATT TTC CAG CCT TCT
--- --- --- --- --- --- --- --- --- --- --- --- --- --- --- --- --- ---
            2817        2826        2835        2844        2853        2862
TTG AGT TGG GTA TTA TTA AAT TCT GGC CAT TAC TTC CAA TGT GAG TGG AAG TGA
--- --- --- --- --- --- --- --- --- --- --- --- --- --- --- --- --- ---
            2871        2880        2889        2898        2907        2916
CAT GTG CAA TTT CTA TAC CTG GCT CAT AAA ACC CTC CCA TGT GCA GCC TTT CAT
--- --- --- --- --- --- --- --- --- --- --- --- --- --- --- --- --- ---
            2925        2934        2943        2952        2961        2970
GTT GAC ATT AAA TGT GAC TTG GGA AGC TAT GTG TTA CAC AGA GTA AAT CAC CAG
--- --- --- --- --- --- --- --- --- --- --- --- --- --- --- --- --- ---
            2979        2988        2997        3006        3015        3024
AAG CCT GGA TTT CTG AAA AAA CTG TGC AGA GCC AAA CCT CTG TCA TTT GCA ACT
--- --- --- --- --- --- --- --- --- --- --- --- --- --- --- --- --- ---
            3033        3042        3051        3060        3069        3078
CCC ACT TGT ATT TGT ACG AGG CAG TTG GAT AAG TGA AAA ATA AAG TAC TAT TGT
--- --- --- --- --- --- --- --- --- --- --- --- --- --- --- --- --- ---
            3087        3096        3105        3114        3123        3132
GTC AAG AAA AAA AAA AAA AAA AAA AAA AAA AAA AAA AAA AAA AAA AAA AAA AAA
--- --- --- --- --- --- --- --- --- --- --- --- --- --- --- --- --- ---

AAA A 3'
--- -
```

FIG. 2

```
              15 16            30 31             45 46            60 61            75 76             90
1 101P3A11  MMVDPNGNESSATYF  ILIGLPGLEBAQFNL  APPLCSLYLIAVLGN  LFIYIVRTEHSLHE  PMYIFLCMLSQIDIL  LSTSSMPKMLAIFNF   90
2 RA1c      -MSSCN---FTHATF  MLIGIPGLSEAHFWF  GFPLLSMTAVALFGN  CIVFIVRTERSLHA  PNYLPLCNLAAIDLA  LSTSTNPKILALFWF   86
3 HPRAJ70   -MSSCN---FTRATC  VLIGIPGLEMANFWV  GFPLLSMYVVAMCGN  CIVVFIVRTERSLHA  PNYLPLCNLAAIDLA  LSTSTMPKILALFWF   86

91              105 106            120 121           135 136           150 151  165 166           180
1 101P3A11  NSTTIQPDACLLQIP  AIHSLSGMESTVLLA  MAFDRYVAICHPLRH  ATVLTLPRVTKIGVA  AVVRGAALM APLFVF  IKQLPFCRSNILSHS  180
2 RA1c      DSREITFDACLAQMF  FIHALSAIESTILLA  MAFDRYVAICHPLRH  AAVLAMFVVQIGMV  ALVRGSLFFFPLPLL  IKRLAFCHSNVLSHS  176
3 HPRAJ70   DSREISIBACLTQMF  FIHALSAIESTILLA  MAFDRYVAICHPLRH  AAVLAMTVTAQIGIV  AVVRGSLFFFPLPLL  IKRLAFCHSNVLSHS  176

181             195 196            210 211           225 226           240 241  255 256           270
1 101P3A11  YCLHQDVMKLACDDI  RVNVVYGLIVISAI  GLDSLLISFSYLLIL  KTVLGLT-RSAQAKA  FGTCVSHVCAVFIFY  VPPIGLSMVHRFSKR  269
2 RA1c      YCVHQDVMKLAYTDT  LPNVVYGLTAILLVM  GVDVMPISLSYFLII  RAVLQLPSKSERAKA  FGTCVSHRIGVVLAFY  VPLIGLSVVHRFGNS  266
3 HPRAJ70   YCVHQDVMKLAYADT  LPNVVYGLTAILLVM  GVDVMPISLSYFLII  RTVLQLPSKSERAKA  FGTCVSHIGVVLAFY  VPLIGLSVVHRFGNS  266

271             285 286            300 301           315 316           330 331              345 346  360
1 101P3A11  RDSPLPVILANTYLL  VPPVLMPIVYGVKTK  EIRQRILRLFHVATH  ASEP----         KDIEAQGNT                         345
2 RA1c      LPIVHVLMGDVYLL  LPPVINPIIYGAKTK  QIRTRVLAMFKISCO  KDIEAQGNT        320
3 HPRAJ70   LHPIVRVMGDIYLL  LPPVINPIIYGAKTK  QIRTRVLAMFKISCD  KDLQAVGK         320
```

FIG. 3

GATCAAACTTCTTTTCCATTCAGAGTCCTCTGATTCAGATTTTAATGTTAACATTTTGGAAGACAGTATTCAGAAAAAA
AATTTCCTTAATAAAAATACAACTCAGATCCTTCAAATATGAAACTGGTTGGGGAATCTCCATTTTTTCAATATTATTT
TCTTCTTTGTTTTCTTGCTACGTATAATTATTAATATCCTGACTAGGTTGTGGTTGGAGGGTTATTACTTTTCATTTTA
CCATGCAGTCCAAATCTAAACTGCTTCTACTGATGGTTTACAGCATTCTGAGATAAGAATGGTACATCTAGAGAACATT
TGCCAAAGGCCTAAGCACAGCAAAGGAAAATAAACACAGAATATAATAAAATGAGATAATCTAGCTTAAAACTATAACT
TCCTCTTTAGAACTCCCAACCACATTTGGATC

FIG. 8A
FIG. 8B
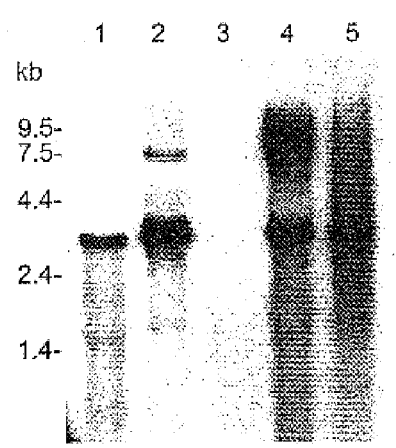
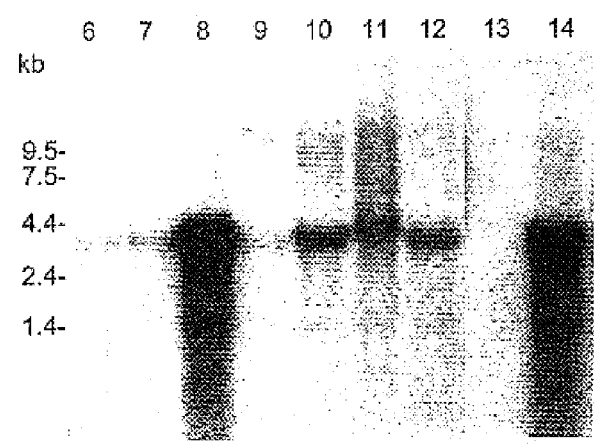

Figure 9A
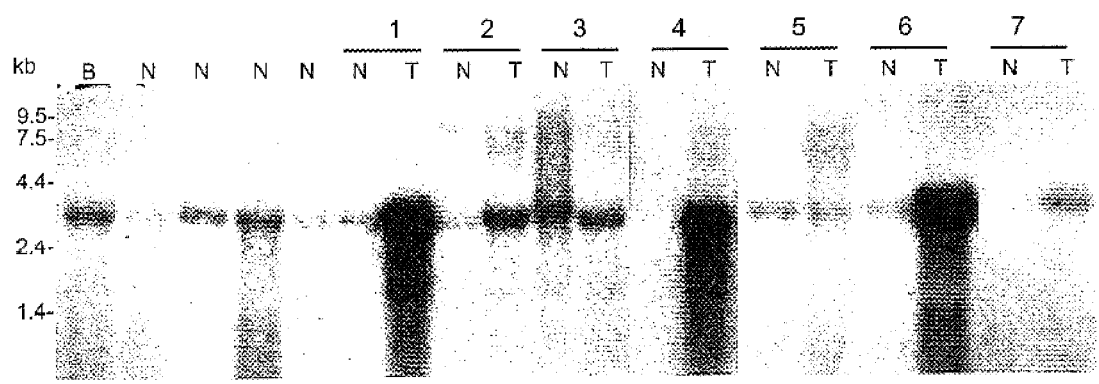
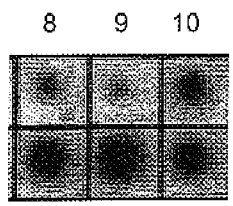
Figure 9B

FIG. 11A
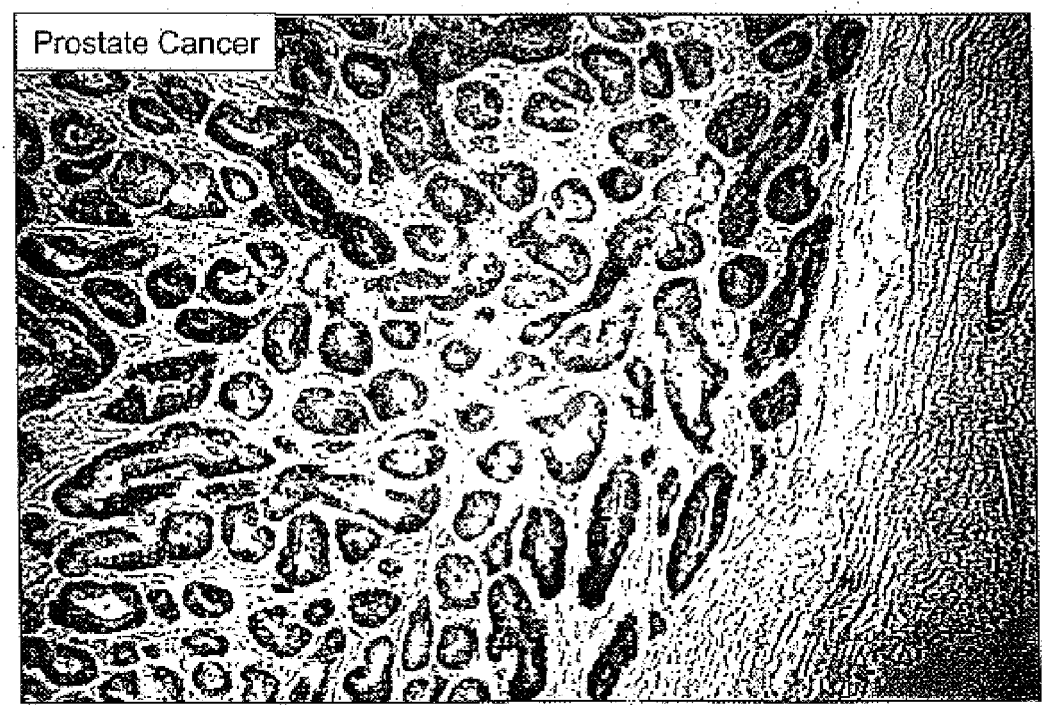
FIG.11B

FIG. 12A
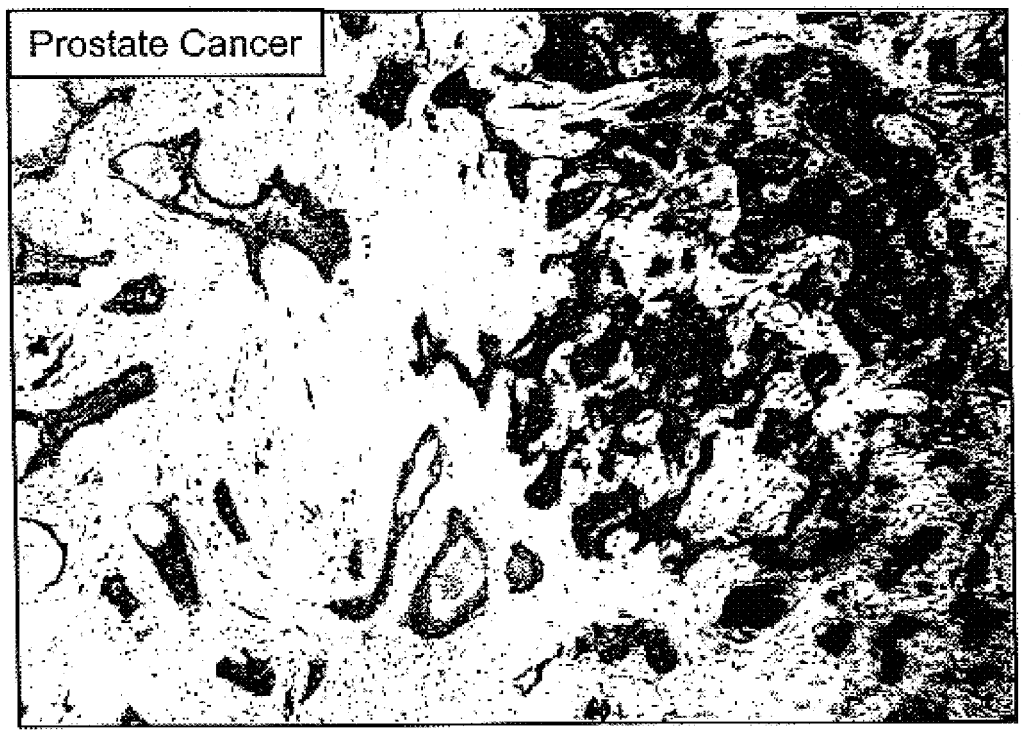
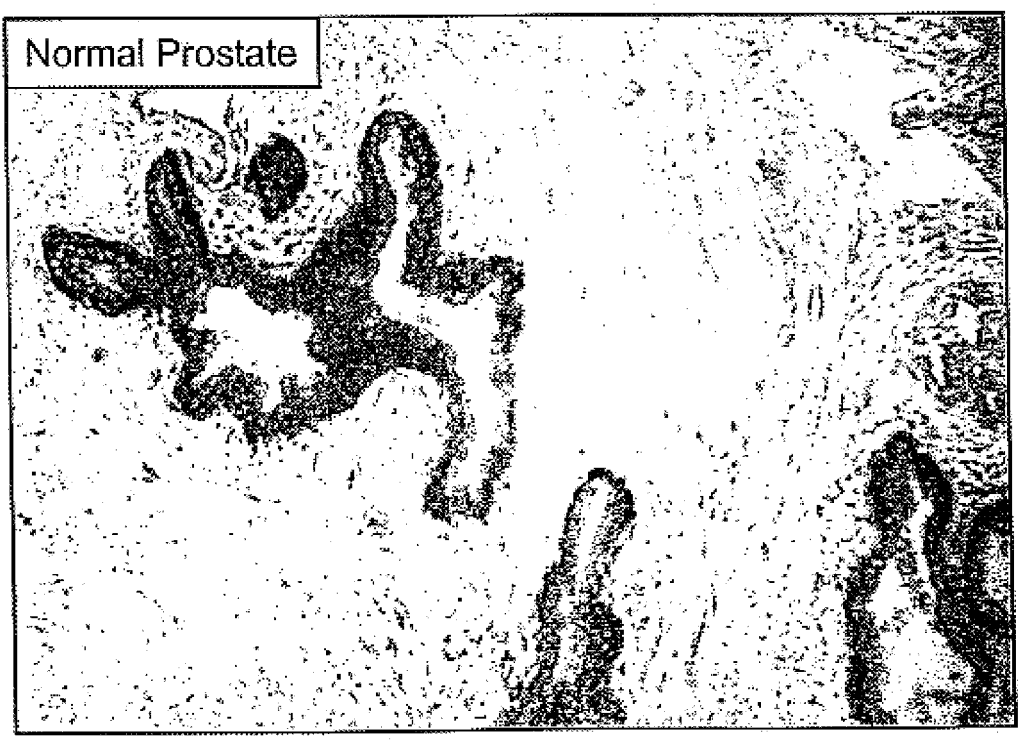
FIG. 12B

Relative fluorescence

Relative fluorescence

FIG. 20A
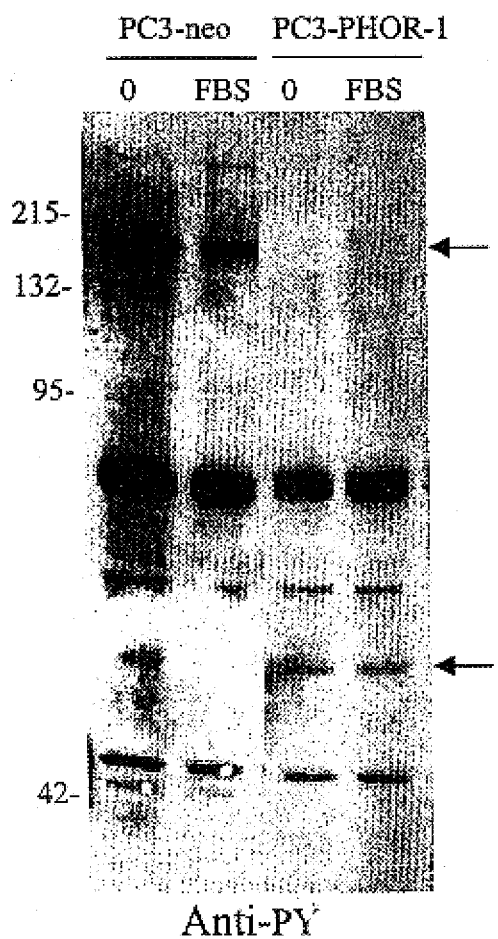
Anti-PY
FIG. 20B
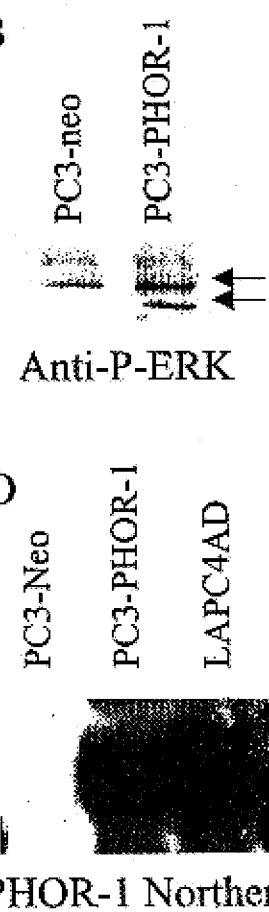
Anti-P-ERK
FIG. 20D
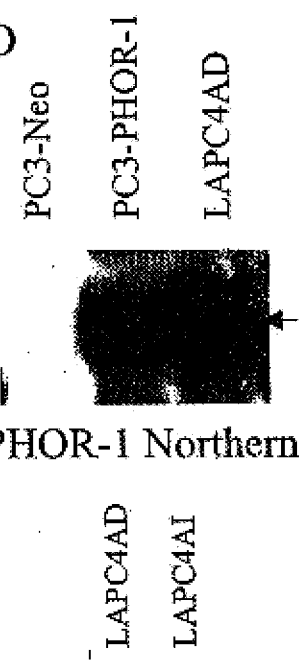
PHOR-1 Northern
PC3-neo PC3-PHOR-1
0 FBS 0 FBS
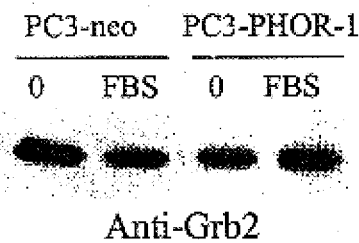
Anti-Grb2
FIG. 20C
FIG. 20E
PHOR1 Northern

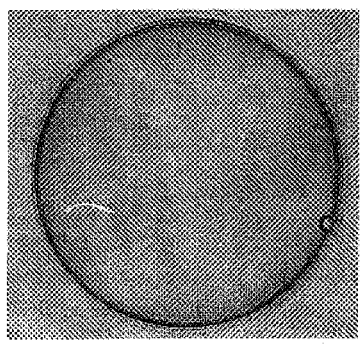 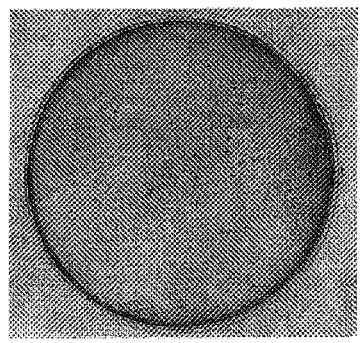 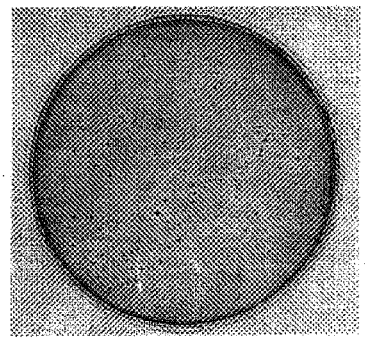
Neo
FIG. 21A
PHOR-1
FIG. 21B
Ras
FIG. 21C

FIG. 22

```
              9            18           27           36           45           54
5' GCT GTG GCC ATG TTT ATT GGA GTG TTG GAT CTA TTC TTT ATC ATC CTA TCT TAT
   --- --- --- --- --- --- --- --- --- --- --- --- --- --- --- --- --- ---
    A   V   A   M   F   I   G   V   L   D   L   F   F   I   I   L   S   Y 63           72           81           90           99          108
   ATC TTT ATC CTT CAG GCA GTT CTA CAA CTC TCC TCT CAG GAG GCC CGC TAC AAA
   --- --- --- --- --- --- --- --- --- --- --- --- --- --- --- --- --- ---
    I   F   I   L   Q   A   V   L   Q   L   S   S   Q   E   A   R   Y   K 117          126          135          144          153          162
   GCA TTT GGG ACA TGT GTC TCT CAC ATA GGT GCC ATC TTA GCC TTC TAC ACA CCT
   --- --- --- --- --- --- --- --- --- --- --- --- --- --- --- --- --- ---
    A   F   G   T   C   V   S   H   I   G   A   I   L   A   F   Y   T   P 171          180          189          198          207          216
   TCA GTC ATC TCT TCA GTC ATG CAC CGT GTG GCC CGC TGT GCT GTG CCA CAC GTC
   --- --- --- --- --- --- --- --- --- --- --- --- --- --- --- --- --- ---
    S   V   I   S   S   V   M   H   R   V   A   R   C   A   V   P   H   V 225          234          243          252          261          270
   CAC ATT CTC CTC GCC AAT TTC TAT CTG CTC TTC CCA CCC ATG GTC AAT CCC ATC
   --- --- --- --- --- --- --- --- --- --- --- --- --- --- --- --- --- ---
    H   I   L   L   A   N   F   Y   L   L   F   P   P   M   V   N   P   I 279          288          297          306          315          324
   ATC TAT GGC GTT AAG ACC AAG CAG ATC CGT GAC AGT CTT GGG AGT ATT CCT GAG
   --- --- --- --- --- --- --- --- --- --- --- --- --- --- --- --- --- ---
    I   Y   G   V   K   T   K   Q   I   R   D   S   L   G   S   I   P   E 333          342          351          360          369          378
   AAA GGA TGT GTG AAT AGA GAG TGA GGA ATA AGT GGA AAA AGA GTG GGG CCC AGT
   --- --- --- --- --- --- --- --- --- --- --- --- --- --- --- --- --- ---
    K   G   C   V   N   R   E   *

387          396          405          414          423          432
   GAA TGC TGT AGT GGG CCA GGG CTG TGC TGA GAG TAG ATG GGT CCT AGA CTC CAC
   --- --- --- --- --- --- --- --- --- --- --- --- --- --- --- --- --- ---

441          450          459          468          477          486
   GTT TAG TTC TTT TCT TGT ATT ATG AAA AGA ATA AAT GAT GTC CTG AAG CTC AGA
   --- --- --- --- --- --- --- --- --- --- --- --- --- --- --- --- --- ---

495
   AAA AAA AAA AAA AAA 3'
   --- --- --- --- ---
```

G PROTEIN-COUPLED RECEPTOR UP-REGULATED IN PROSTATE CANCER AND USES THEREOF

This application claims the benefit of United States provisional patent application No. 60/157,902, filed Oct. 5, 1999, the entire contents of which are incorporated herein by reference.

FIELD OF THE INVENTION

The invention described herein relates to a novel gene and its encoded protein, termed PHOR-1, and to diagnostic and therapeutic methods and compositions useful in the management of various cancers that express PHOR-1, particularly prostate cancers.

BACKGROUND OF THE INVENTION

Cancer is the second leading cause of human death next to coronary disease. Worldwide, millions of people die from cancer every year. In the United States alone, cancer causes the death of well over a half-million people annually, with some 1.4 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Many cancer patients experience a recurrence.

Worldwide, prostate cancer is the fourth most prevalent cancer in men. In North America and Northern Europe, it is by far the most common male cancer and is the second leading cause of cancer death in men. In the United States alone, well over 40,000 men die annually of this disease—second only to lung cancer. Despite the magnitude of these figures, there is still no effective treatment for metastatic prostate cancer. Surgical prostatectomy, radiation therapy, hormone ablation therapy, and: chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the management of this disease. Although the serum PSA assay has been a very useful tool, its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic disease progression, including the transition from androgen dependence to androgen independence and the development of metastatic lesions (Klein et al., 1997, Nat. Med.3:402). More recently identified prostate cancer markers include PCTA-1 (Su et al., 1996, Proc. Natl. Acad. Sci. USA 93: 7252), prostate stem cell antigen (PSCA) (Reiter et al., 1998, Proc. Natl. Acad. Sci. USA 95:1735), and STEAP (Hubert et al., 1999, Proc. Natl. Acad. Sci. USA 96: 14523).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

SUMMARY OF THE INVENTION

The present invention relates to a novel prostate-specific G protein-coupled receptor up-regulated in prostate cancer, termed PHOR-1. PHOR-1 expression is largely restricted to the prostate, and is markedly up-regulated in prostate tumors. Expression of PHOR-1 in matched normal prostate/tumor samples from advanced prostate cancer patients, using both mRNA and protein detection methods, shows a high degree of up-regulated expression in the tumor tissue, suggesting that PHOR-1 is a useful marker for prostate cancer detection. Analysis of normal/tumor samples from other human cancer patients demonstrates up-regulation of PHOR-1 expression in kidney, uterine, cervical, stomach and rectal cancers as well. In addition, expression of PHOR-1 induces colony growth and modulates cAMP and tyrosine phosphorylation in manners indicative of a functional role in tumorigenesis and transformation, providing a strategic target for cancer therapy.

The structure of PHOR-1 includes seven putative transmembrane domains spanning the 317 amino acid protein sequence. PHOR-1 is expressed at the cell surface, with the N-terminus exposed on the outside of the cell membrane. The PHOR-1 protein is homologous to a large family of olfactory receptors that are expressed in olfactory epithelium and neurons. PHOR-1 exhibits functional activity consistent with other G protein-coupled receptors, suggesting that PHOR-1 plays a critical role in the regulation of cell function, proliferation, and transformation.

A number of potential approaches to the treatment of prostate cancer and other cancers expressing PHOR-1 are described herein. The cell surface orientation and G protein-coupled nature of this receptor presents a number of therapeutic approaches using molecules that target PHOR-1 and its function, as well as molecules that target other proteins, factors and ligands that act through the PHOR-1 receptor. These therapeutic approaches include antibody therapy with anti-PHOR-1 antibodies, small molecule therapies, and vaccine therapies. In addition, given its up-regulated expression in prostate cancer, PHOR-1 is useful as a diagnostic, staging and/or prognostic marker for prostate cancer and, similarly, may be a marker for other cancers expressing this receptor.

The invention provides polynucleotides corresponding or complementary to all or part of the PHOR-1 genes, mRNAs, and/or coding sequences, preferably in isolated form, including polynucleotides encoding PHOR-1 proteins and fragments thereof, DNA, RNA, DNA/RNA hybrid, and related molecules, polynucleotides or oligonucleotides complementary to the PHOR-1 genes or mRNA sequences or parts thereof, and polynucleotides or oligonucleotides which hybridize to the PHOR-1 genes, mRNAs, or to PHOR-1-encoding polynucleotides. Also provided are means for isolating cDNAs and the genes encoding PHOR-1. Recombinant DNA molecules containing PHOR-1 polynucleotides, cells transformed or transduced with such molecules, and host vector systems for the expression of PHOR-1 gene products are also provided.

The invention further provides PHOR-1 proteins and polypeptide fragments thereof, as well as antibodies that bind to PHOR-1 proteins and polypeptide fragments thereof. The antibodies of the invention include polyclonal and monoclonal antibodies, murine and other mammalian antibodies, chimeric antibodies, humanized and fully human antibodies, antibodies labeled with a detectable marker, and antibodies conjugated to radionuclides, toxins or other therapeutic compositions.

The invention further provides methods for detecting the presence of PHOR-1 polynucleotides and proteins in various biological samples, as well as methods for identifying cells that express a PHOR-1. The invention further provides various therapeutic compositions and strategies, including particularly, antibody, vaccine and small molecule therapy, for treating cancers of the prostate, kidney, cervix, uterus, rectum and stomach.

The invention additionally provides a method of identifying a molecule that modulates a biological activity of PHOR-1. The method comprises contacting a molecule with a cell that expresses PHOR-1, assaying a biological activity of PHOR-1 in the presence and absence of the molecule, and determining whether the biological activity of PHOR-1 is altered by the presence of the molecule. An alteration in the biological activity of PHOR-1 is indicative of a molecule that modulates a biological activity of PHOR-1. Preferably, the biological activity of PHOR-1 assayed in the method comprises tyrosine phosphorylation, cytosolic cAMP accumulation, or stimulation of colony growth.

BRIEF DESCRIPTION OF THE FIGURES

FIGS. 1A–1D. Nucleotide (SEQ ID NO: 1) and deduced amino acid (SEQ ID NO: 2) sequences of human PHOR-1 cDNA (clone GTH10). The putative start methionine is shown in bold-face type. The sequence exhibits two adjacent methionines at the start, with the sequence surrounding the second methionine (ATG ATG G) exhibiting a Kozak sequence. The seven putative transmembrane domains are boxed.

FIG. 2. Amino acid sequence alignment of human PHOR-1 with HPRAJ70 (SEQ ID NO: 4) and RA1c (SEQ ID NO: 3) using the ClustalW 1.7 program (BCM Search Launcher). Putative transmembrane domains are indicated in bold or are boxed. The boxed domain was identified by homology to HPRAJ70 and RA1c. The bold domains were identified using the web tool SOSUI at http://www.tuat.ac.jp/~mitaku/adv sosui/submit.html.

FIG. 3. Nucleotide sequence (SEQ ID NO: 5) of SSH-derived fragment corresponding to the PHOR-1 gene.

FIG. 6A. Northern blot analysis of PHOR-1 in heart (lane 1), brain (lane 2), placenta (lane 3), lung (lane 4), liver (lane 5), skeletal muscle (lane 6), kidney (lane 7), and pancreas (lane 8).

FIG. 6B. Northern blot analysis of PHOR-1 in spleen (lane 1), thymus (lane 2), normal prostate (lane 3), testis (lane 4), ovary (lane 5), small intestine (lane 6), colon (lane 7), and leukocytes (lane 8).

FIG. 6C. Northern blot analysis of PHOR-1 in normal prostate (lane 1), LAPC-4 AD (lane 2), LAPC-4 AI (lane 3), LAPC-9 AD (lane 4), and LAPC-9 AI (lane 5).

FIG. 8A. Northern blot analysis of PHOR-1 expression in human prostate cancer xenografts, showing high level over-expression of PHOR-1 in prostate tumors. Normal prostate (lane 1); LAPC-4 AD (lane 2); LAPC-4 AI (lane 3); LAPC-9 AD (lane 4); LAPC 9 AI (lane 5).

FIG. 8B. Northern blot analysis of PHOR-1 expression in human patient biopsy samples, showing high level over-expression of PHOR-1 in prostate tumors. Normal prostate (lane 6); patient 1, normal adjacent tissue (lane 7); patient 1, Gleason 7 tumor (lane 8); patient 2, normal adjacent tissue (lane 9); patient 2, Gleason 9 tumor (lane 10); patient 3, normal adjacent tissue (lane 11); patient 3, Gleason 7 tumor (lane 12); patient 4, normal adjacent tissue (lane 13); patient 4, Gleason 7 tumor (lane 14).

FIG. 9A. PHOR-1 expression in prostate cancer, showing up-regulation by northern analysis in 5 of 7 (or 8 of 10, when combined with FIG. 9B) tumor specimens. Shown are matched tumor (T) and normal (N) patient samples for the following tumor types: Gleason 7 (lane pair 1); Gleason 9 (lane pair 2); Gleason 7 (lane pairs 3–5); Gleason 6 (lane pairs 6–7); B represents benign prostatic hyperplasia (BPH); N represents additional normal specimens.

FIG. 9B. PHOR-1 expression in prostate cancer, showing up-regulation by dot blot analysis in 3 of 3 (or 8 of 10, when combined with FIG. 9A) tumor specimens. Shown are matched tumor (T) and normal (N) patient samples for the following tumor types: Gleason 7 (dot pair 8); Gleason 8 (dot pair 9); Gleason 7 (dot pair 10).

FIG. 11A. Photomicrograph showing PHOR-1 expression in prostatic intraepithelial neoplasia (PIN) by in situ hybridization with an anti-sense PHOR-1 riboprobe.

FIG. 11B. Photomicrograph showing PHOR-1 expression in prostate cancer issue by in situ hybridization with an anti-sense PHOR-1 riboprobe.

FIG. 12A. Photomicrograph showing PHOR-1 expression in prostate cancer by in situ hybridization with an anti-sense PHOR-1 riboprobe. Note up-regulation of expression relative to normal prostate, FIG. 12B.

FIG. 12B. Photomicrograph showing PHOR-1 expression in normal prostate by in situ hybridization with an anti-sense PHOR-1 riboprobe.

FIG. 20A. Western analysis of alteration of tyrosine phosphorylation by PHOR-1. PC3 cells, stably expressing either neo or PHOR-1 in the pSRα retroviral vector were grown in 1% FBS overnight. The cells were then either left untreated or were treated with 10% FBS for 3 min. The cells were lysed and analyzed by western blotting with anti-phosphotyrosine (UBI, Lake Placid, N.Y.).

FIG. 20B. Western analysis of alteration of Erk phosphorylation by PHOR-1. PC3 cells, stably expressing either neo or PHOR-1 in the pSRα retroviral vector were processed as described for FIG. 19A. The cells were lysed and analyzed by western blotting with anti-phospho-ERK (Cell Signal, Beverly, Mass.) mAb.

FIG. 20C. PC3 cells prepared as described for FIGS. 19A–B were also probed for Grb2. Anti-Grb2 mAb (Transduction Laboratories, San Diego, Calif.) overlay shows equal protein loading.

FIG. 20D. Northern analysis of PC3-neo and PC3-PHOR-1 cells. PC3 cells described in FIGS. 19A–C above were evaluated for PHOR-1 expression by northern blotting. RNA was extracted from control PC3-neo cells and PC3 cells stably transduced with PHOR-1 and the RNA blots were hybridized using PHOR-1 probe (Xba-Ecor1 fragment of clone GTH10). RNA from LAPC4 xenografts was used as a positive control (see FIG. 20). The results show that the PHOR-1 mRNA is expressed in retroviral transduced PC3-PHOR-1 cells but not in control cells.

FIG. 20E. Northern blot showing PHOR-1 expression in LAPC4 xenografts. Strong expression is observed in the androgen dependent (AD) LAPC4, but not in the androgen independent (AI) LAPC4.

FIG. 21A. NIH-3T3 cells stably expressing PHOR-1 were analyzed for their ability to form colonies in soft agar. NIH-3T3 cells, stably expressing neo were used as negative controls. The experiment was performed in duplicate. The assay was evaluated 4 weeks after cell plating.

FIG. 21B. NIH-3T3 cells stably expressing PHOR-1 were analyzed for their ability to form colonies in soft agar. The experiment was performed in duplicate. The assay was evaluated 4 weeks after cell plating. The colony count shows that PHOR-1 induces a 3-fold increase in colony formation relative to neo control (FIG. 21A). This significant increase has been observed in 2 separate experiments. The results indicate that expression of PHOR-1 in NIH 3T3 cells induces a 3–4 fold increase in colony formation as compared to 5 fold increase by the strong oncogene Ras (see FIG. 21C), suggesting that PHOR-1 has significant transforming capabilities.

FIG. 21C. NIH-3T3 cells stably expressing PHOR1 were analyzed for their ability to form colonies in soft agar (FIG. 21B). NIH-3T3 cells, stably expressing activated-Ras were used as positive controls. The experiment was performed in duplicate. The assay was evaluated 4 weeks after cell plating.

FIG. 22. Nucleotide (SEQ ID NO: 6) and deduced ORF amino acid (SEQ ID NO: 7) sequences of AI138218, a PHOR-1 family member.

DETAILED DESCRIPTION OF THE INVENTION

Figure 4:
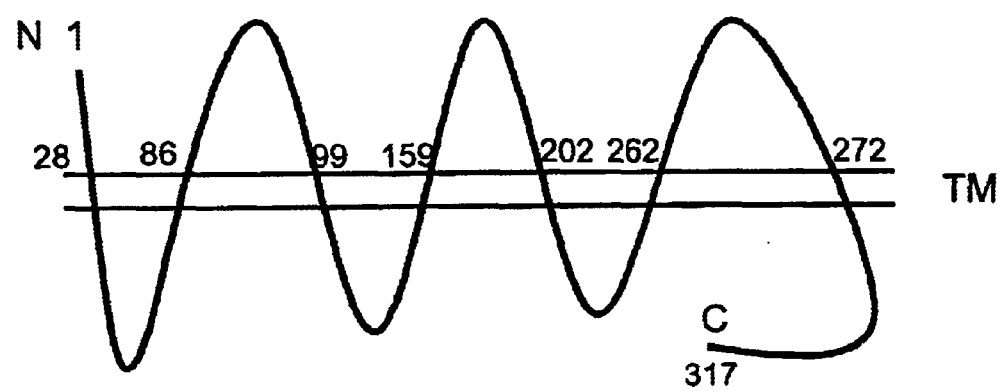
FIG. 4. Schematic representation of the gross topology of the transmembrane PHOR-1 protein.

The invention provides a novel prostate-specific G protein-coupled receptor up-regulated in prostate cancer, termed PHOR-1. PHOR-1 appears to be expressed exclusively in the prostate, and is markedly up-regulated in prostate tumors. Expression of PHOR-1 in matched normal prostate/tumor samples from advanced prostate cancer patients, using both mRNA and protein detection methods, shows a high degree of up-regulated expression in the tumor tissue, suggesting that PHOR-1 is a useful marker for prostate cancer detection. In addition, expression of PHOR-1 induces colony growth, tyrosine phosphorylation, and cAMP modulation in manners indicative of a functional role in tumorigenesis and transformation, providing a strategic target for cancer therapy.

The PHOR-1 protein is homologous to a large family of olfactory receptors that are expressed in olfactory epithelium and neurons. The cell surface orientation and G protein-coupled nature of this receptor presents a number of therapeutic approaches using molecules that target PHOR-1 and its function. These therapeutic approaches include antibody therapy with anti-PHOR-1 antibodies, small molecule therapies, and vaccine therapies. In addition, given its up-regulated expression in prostate cancer, PHOR-1 is useful as a diagnostic, staging and/or prognostic marker for prostate cancer and, similarly, can serve as a marker for other cancers expressing this receptor.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1–C2 disease under the Whitmore-Jewett system, and stage T3–T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

As used herein, the terms "metastatic prostate cancer" and "metastatic disease" mean prostate cancers that have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is the preferred treatment modality. Patients with metastatic prostate cancer eventually develop an androgen-refractory state within 12 to 18 months of treatment initiation, and approximately half of these patients die within 6 months thereafter. The most common site for prostate cancer metastasis is bone. Prostate cancer bone metastases are, on balance, characteristically osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA.

As used herein, the term "polypeptide" means a polymer of at least 10 amino acids. Throughout the specification, standard three letter or single letter designations for amino acids are used.

As used herein, the terms "hybridize", "hybridizing", "hybridizes" and the like, used in the context of polynucleotides, are meant to refer to conventional hybridization conditions, preferably such as hybridization in 50% formamide/6×SSC/0.1% SDS/100 µg/ml ssDNA, in which temperatures for hybridization are above 37° C. and temperatures for washing in 0.1×SSC/0.1% SDS are above 55° C., and most preferably to stringent hybridization conditions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and %SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

In the context of amino acid sequence comparisons, the term "identity" is used to express the percentage of amino acid residues at the same relative positions that are the same. Also in this context, the term "homology" is used to express the percentage of amino acid residues at the same relative positions that are either identical or are similar, using the conserved amino acid criteria of BLAST analysis, as is generally understood in the art. For example, % identity values may be generated by WU-BLAST-2 (Altschul et al., Methods in Enzymology, 266: 460–480 (1996): http://blast.wustl/edu/blast/README. html). Further details regarding amino acid substitutions, which are considered conservative under such criteria, are provided below.

Additional definitions are provided throughout the subsections that follow.

Phor-1 Polynucleotides

One aspect of the invention provides polynucleotides corresponding or complementary to all or part of a PHOR-1 gene, mRNA, and/or coding sequence, preferably in isolated form, including polynucleotides encoding a PHOR-1 protein and fragments thereof, DNA, RNA, DNA/RNA hybrid, and related molecules, polynucleotides or oligonucleotides complementary to a PHOR-1 gene or mRNA sequence or a part thereof, and polynucleotides or oligonucleotides that hybridize to a PHOR-1 gene, mRNA, or to a PHOR-1 encoding polynucleotide (collectively, "PHOR-1 polynucleotides"). As used herein, the PHOR-1 gene and protein is meant to include the PHOR-1 genes and proteins specifically described herein and the genes and proteins corresponding to other PHOR-1 proteins and structurally similar variants of the foregoing. Such other PHOR-1 proteins and variants will generally have coding sequences that are highly homologous to the PHOR-1 coding sequence, and preferably will share at least about 50% amino acid identity and at least about 60% amino acid homology (using BLAST criteria), more preferably sharing 70% or greater homology (using BLAST criteria).

One embodiment of a PHOR-1 polynucleotide is a PHOR-1 polynucleotide having the sequence shown in FIGS. 1A–D (SEQ ID NO: 1). A PHOR-1 polynucleotide may comprise a polynucleotide having the nucleotide sequence of human PHOR-1 as shown in FIGS. 1A–D (SEQ ID NO: 1), wherein T can also be U; a polynucleotide that encodes all or part of the PHOR-1 protein; a sequence complementary to the foregoing; or a polynucleotide fragment of any of the foregoing. Another embodiment comprises a polynucleotide having the sequence as shown in FIGS. 1A–D (SEQ ID NO: 1), from nucleotide residue number 133 through nucleotide residue number 1083, or from nucleotide residue number 388 through nucleotide residue number 1062, wherein T can also be U. Another embodiment comprises a polynucleotide encoding a PHOR-1 polypeptide whose sequence is encoded by the cDNA contained in the plasmid p101P3A11 as deposited with American Type Culture Collection on Jul. 2, 1999 as Accession No. PTA-312. Another embodiment comprises a polynucleotide that is capable of hybridizing under stringent hybridization conditions to the human PHOR-1 cDNA shown in FIGS. 1A–D (SEQ ID NO: 1) or to a polynucleotide fragment thereof.

Typical embodiments of the invention disclosed herein include PHOR-1 polynucleotides encoding specific portions of the PHOR-1 mRNA sequence such as those that encode the protein and fragments thereof. For example, representative embodiments of the invention disclosed herein include: polynucleotides encoding about amino acid 1 to about amino acid 10 of the PHOR-1 protein shown in FIGS. 1A–D (SEQ ID NO: 2), polynucleotides encoding about amino acid 20 to about amino acid 30 of the PHOR-1 protein shown in FIGS. 1A–D (SEQ ID NO: 2), polynucleotides encoding about amino acid 30 to about amino acid 40 of the PHOR-1 protein shown in FIGS. 1A–D (SEQ ID NO: 2), polynucleotides encoding about amino acid 40 to about amino acid 50 of the PHOR-1 protein shown in FIGS. 1A–D (SEQ ID NO: 2), polynucleotides encoding about amino acid 50 to about amino acid 60 of the PHOR-1 protein shown in FIGS. 1A–D (SEQ ID NO: 2), polynucleotides encoding about amino acid 60 to about amino acid 70 of the PHOR-1 protein shown in FIGS. 1A–D (SEQ ID NO: 2), polynucleotides encoding about amino acid 70 to about amino acid 80 of the PHOR-1 protein shown in FIGS. 1A–D (SEQ ID NO: 2), polynucleotides encoding about amino acid 80 to about amino acid 90 of the PHOR-1 protein shown in FIGS. 1A–D (SEQ ID NO: 2) and polynucleotides encoding about amino acid 90 to about amino acid 100 of the PHOR-1 protein shown in FIGS. 1A–D (SEQ ID NO: 2), etc. Following this scheme, polynucleotides (of at least 10 amino acids) encoding portions of the amino acid sequence of amino acids 100–317 of the PHOR-1 protein shown in FIGS. 1A–D (SEQ ID NO: 2) are typical embodiments of the invention. Polynucleotides encoding larger portions of the PHOR-1 protein are also contemplated. For example polynucleotides encoding from about amino acid 1 (or 20 or 30 or 40 etc.) to about amino acid 20, (or 30, or 40 or 50 etc.) of the PHOR-1 protein shown in FIGS. 1A–D (SEQ ID NO: 2) may be generated by a variety of techniques well known in the art.

Additional illustrative embodiments of the invention disclosed herein include PHOR-1 polynucleotide fragments encoding one or more of the biological motifs contained within the PHOR-1 protein sequence. In one embodiment, typical polynucleotide fragments of the invention can encode one or more of the regions of PHOR-1 that exhibit homology to HPRAJ70 or RA1c, as shown in FIG. 2. In another embodiment of the invention, typical polynucleotide fragments can encode one or more GPCR signature sequences or olfactory receptor signature sequences. In yet another embodiment of the invention, typical polynucleotide fragments can encode sequences that are unique to one or more PHOR-1 alternative splicing variants. In another embodiment of the invention, typical polynucleotide fragments can include a portion of the nucleotide sequence shown in SEQ ID NO: 1, for example, from nucleotide residue number 388 through nucleotide residue number 1062, from nucleotide residue number 159 through nucleotide residue number 733, from nucleotide residue number 854 through nucleotide residue number 3136, or from nucleotide residue number 133 through nucleotide residue number 1083.

The polynucleotides of the preceding paragraphs have a number of different specific uses. As PHOR-1 is shown to be overexpressed in prostate and other cancers, these polynucleotides may be used in methods assessing the status of PHOR-1 gene products in normal versus cancerous tissues. Typically, polynucleotides encoding specific regions of the PHOR-1 protein may be used to assess the presence of perturbations (such as deletions, insertions, point mutations etc.) in specific regions (such regions containing a transmembrane domain) of the PHOR-1 gene products. Exemplary assays include both RT-PCR assays as well as single-strand conformation polymorphism (SSCP) analysis (see e.g. Marrogi et al., J. Cutan. Pathol. 26(8): 369–378 (1999), both of which utilize polynucleotides encoding specific regions of a protein to examine these regions within the protein. Assays and methods for analyzing sequences to detect single nucleotide polymorphisms are also available (Irizarry, et al., 2000, Nature Genetics 26(2):223–236.

Other specifically contemplated embodiments of the invention disclosed herein are genomic DNA, cDNAs, ribozymes, and antisense molecules, including morpholino anti-sense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the PHOR-1 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., PHOR-1. See for example, Jack Cohen, OLIGODEOXYNUCLEOTIDES, Antisense Inhibitors of Gene Expression, CRC Press, 1989; and Synthesis 1:1–5 (1988). The PHOR-1 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1,1-dioxide, which is a sulfur transfer reagent. See Iyer, R. P. et al, J. Org. Chem. 55:4693–4698 (1990); and Iyer, R. P. et al., J. Am. Chem. Soc. 112:1253–1254 (1990), the disclosures of which are fully incorporated by reference herein. Additional PHOR-1 antisense oligonucleotides of the present invention include morpholino antisense oligonucleotides known in the art (see e.g. Partridge et al., 1996, Antisense & Nucleic Acid Drug Development 6: 169–175).

The PHOR-1 antisense oligonucleotides of the present invention typically may be RNA or DNA that is complementary to and stably hybridizes with the first 100 N-terminal codons or last 100 C-terminal codons, or overlapping with the ATG start site, of the PHOR-1 genome or the corresponding mRNA. While absolute complementarity is not required, high degrees of complementarity are preferred. Use of an oligonucleotide complementary to this region allows for the selective hybridization to PHOR-1 mRNA and not to mRNA specifying other regulatory subunits of protein kinase. Preferably, the PHOR-1 antisense oligonucleotides of the present invention are a 15 to 30-mer fragment of the antisense DNA molecule having a sequence that hybridizes to PHOR-1 mRNA. Optionally, PHOR-1 antisense oligonucleotide is a 30-mer oligonucleotide that is complementary to a region in the first 10 N-terminal codons and last 10 C-terminal codons of PHOR-1. Alternatively, the antisense molecules are modified to employ ribozymes in the inhibition of PHOR-1 expression. L. A. Couture & D. T. Stinchcomb; *Trends Genet* 12: 510–515 (1996).

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemi-luminescent compound, metal chelator or enzyme. Such probes and primers can be used to detect the presence of a PHOR-1 polynucleotide in a sample and as a means for detecting a cell expressing a PHOR-1 protein.

Examples of such probes include polypeptides comprising all or part of the human PHOR-1 cDNA sequence shown in FIGS. 1A–D (SEQ ID NO: 1). Examples of primer pairs capable of specifically amplifying PHOR-1 mRNAs are also described in the Examples that follow. As will be understood by the skilled artisan, a great many different primers and probes may be prepared based on the sequences provided herein and used effectively to amplify and/or detect a PHOR-1 mRNA.

As used herein, a polynucleotide is said to be "isolated" when it is substantially separated from contaminant polynucleotides that correspond or are complementary to genes other than the PHOR-1 gene or that encode polypeptides other than PHOR-1 gene product or fragments thereof A skilled artisan can readily employ nucleic acid isolation procedures to obtain an isolated PHOR-1 polynucleotide..

The PHOR-1 polynucleotides of the invention are useful for a variety of purposes, including but not limited to their use as probes and primers for the amplification and/or detection of the PHOR-1 gene(s), mRNA(s), or fragments thereof; as reagents for the diagnosis and/or prognosis of prostate cancer and other cancers; as tools for identifying molecules that inhibit calcium entry specifically into prostate cells; as coding sequences capable of directing the expression of PHOR-1 polypeptides; as tools for modulating or inhibiting the expression of the PHOR-1 gene(s) and/or translation of the PHOR-1 transcript(s); and as therapeutic agents.

Molecular and Biochemical Features of Phor-1

As is described further in the Examples that follow, the PHOR-1 gene and protein have been characterized in a variety of ways. For example, analyses of nucleotide coding and amino acid sequences were conducted in order to identify conserved structural elements within the PHOR-1 sequence, topological features, post-translational modifications, and potentially related molecules. RT-PCR, in situ hybridization, and northern blot analyses of PHOR-1 mRNA expression were conducted in order to establish the range of normal and cancerous tissues expressing the various PHOR-1 messages. Western blot and fluorescence-activated cell sorting (FACS) analyses of PHOR-1 protein expression in experimentally transfected cells were conducted to determine cell surface localization. PHOR-1 has a pI of 8.7 and a calculated molecular weight of 35.2 kD.

PHOR-1 is a prostate-specific G protein-coupled receptor (GPCR) expressed at high levels in advanced and localized prostate tumors. The PHOR-1 protein sequence reveals 7 potential transmembrane domains and has homology to GPCRs involved in olfaction (Raming et al., 1993, Nature 361: 353; Malnic et al., 1999, Cell 96:713). A rat olfactory receptor expressed in brain, known as RA1c (Raming et al., 1998, Receptor Channels 6: 141), has a sequence with the highest degree of homology to PHOR-1. PHOR-1 is 59.9% identical to RA1c in 299 residue overlap. The likely human homologue of RA1c, HPRAJ70, also shows a similar degree of homology to PHOR-1 (59.4% identical to HPRAJ70 across a 298 residue overlap). The HPRAJ70 protein is reported to be a prostate-specific GPCR (U.S. Pat. No. 5,756,309, PCT application WO 96/39435). Alignments of the amino acid sequences of PHOR-1, HPRAJ70, and RA1c are provided in FIG. 1B.

The homology of PHOR-1 with brain olfactory receptors led to the designation Prostate Homologue of Olfactory Receptor-1 (PHOR-1). Proteins that are members of this receptor family exhibit an extracellular amino-terminus, three additional extracellular loops, three intracellular loops and an intracellular carboxyl terminus. The second extracellular region of PHOR-1 exhibits a potential N-glycosylation site at residue 90 (NSTT) suggesting that the protein may be glycosylated. GPCRs are seven-transmembrane receptors that are stimulated by polypeptide hormones or small molecules. Their signals are transmitted via trimeric guanine-nucleotide binding proteins (G proteins) to effector enzymes or ion channels (Simon et al., 1991, Science 252: 802).

Recently, GPCRs have also been shown to link to mitogenic signaling pathways of tyrosine kinases (Luttrell et al., 1999, Science 283: 655; Luttrell et al., 1999 Curr Opin Cell Biol 11: 177). GPCRs are regulated by phosphorylation mediated by GPCR kinases (GRKs), which themselves are indirectly activated by the GPCRs (Pitcher et al., 1998, Ann. Rev. Biochem. 67: 653). Olfactory GPCRs transmit their signals by activating the cAMP pathway via adenylate cyclase and the phospholipase C pathway by generating inositol 1,4,5-trisphosphate (IP3) and diacyl-glycerol (DAG) (Breer, 1993, Ciba Found Symp 179: 97; Bruch, 1996, Comp Biochem Physiol B Biochem Mol Biol 113:451). Generation of cAMP leads to activation of protein kinase A. IP3 results in an increase in intracellular calcium, while DAG activates protein kinase C.

As discussed in more detail in the Examples that follow, PHOR-1 exhibits functional features of a GPCR, as evidenced by the behavior of cells transfected with a vector to express PHOR-1. Expression of PHOR-1 induces tyrosine phosphorylation of a 55 kDa protein and de-phosphorylation of a 130 kDa protein, and also induces phosphorylation of Erk, a mitogen-activated protein kinase. PHOR-1 expression modulates cytoplasmic cAMP concentration, as evidenced by accumulation of cAMP in response to fetal bovine serum (FBS) by PHOR-1-expressing cells. In addition, PHOR-1 expression stimulates colony growth in soft agar.

Figure 5A:
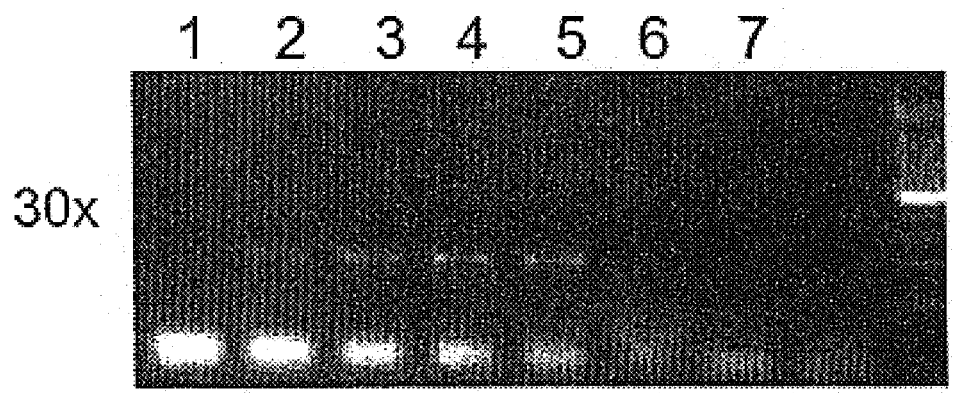
FIG. 5A. Semi-quantitative RT-PCR expression analysis showing human PHOR-1 expression restricted to prostate and prostate cancer xenografts. Shown are: brain (lane 1), normal prostate (lane 2), LAPC-4 AD lane 3), LAPC-4 AD 3 days post castration (lane 4), LAPC-4 AD 14 days post castration lane 5), LAPC-4 AI (lane 6), HeLa cells (lane 7) and negative control (lane 8).
Figure 5B:
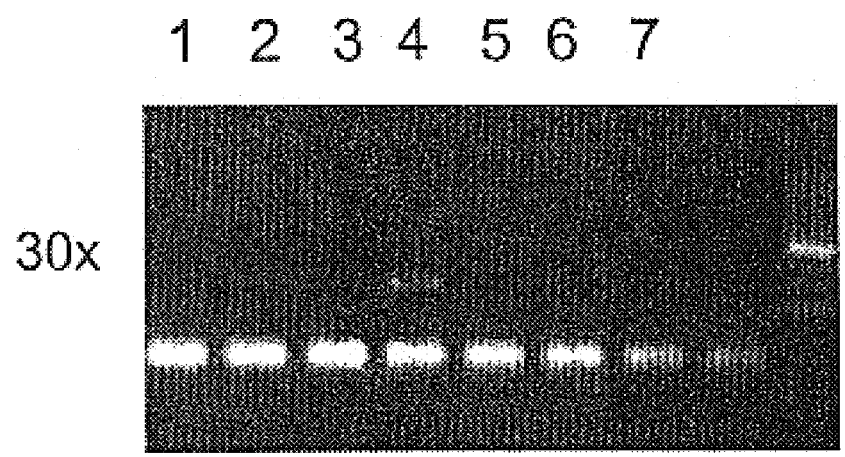
FIG. 5B. Semi-quantitative RT-PCR expression analysis showing human PHOR-1 expression restricted to prostate. Shown are: colon (lane 1), ovary (lane 2), leukocytes (lane 3), normal prostate (lane 4), small intestine (lane 5), spleen (lane 6), testis (lane 7) and thymus (lane 8).
Figure 6A:
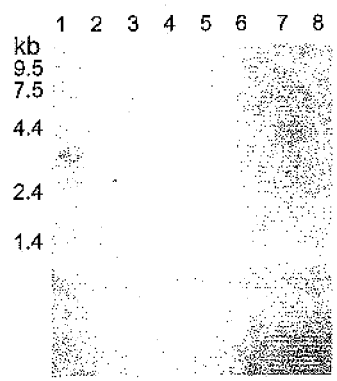
FIGS. 6A–6C show the results of northern blot analysis of PHOR-1 expression, demonstrating expression restricted to normal prostate and prostate cancer xenografts.
Figure 6B:
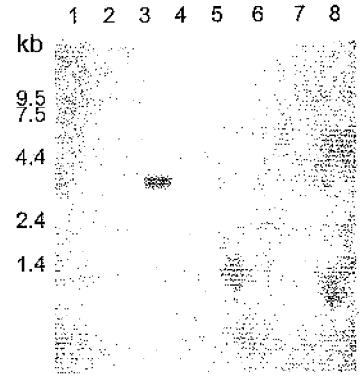
Figure 6C:
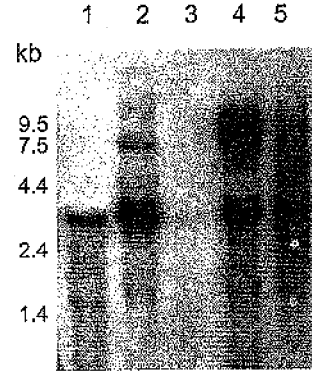
Figure 7:
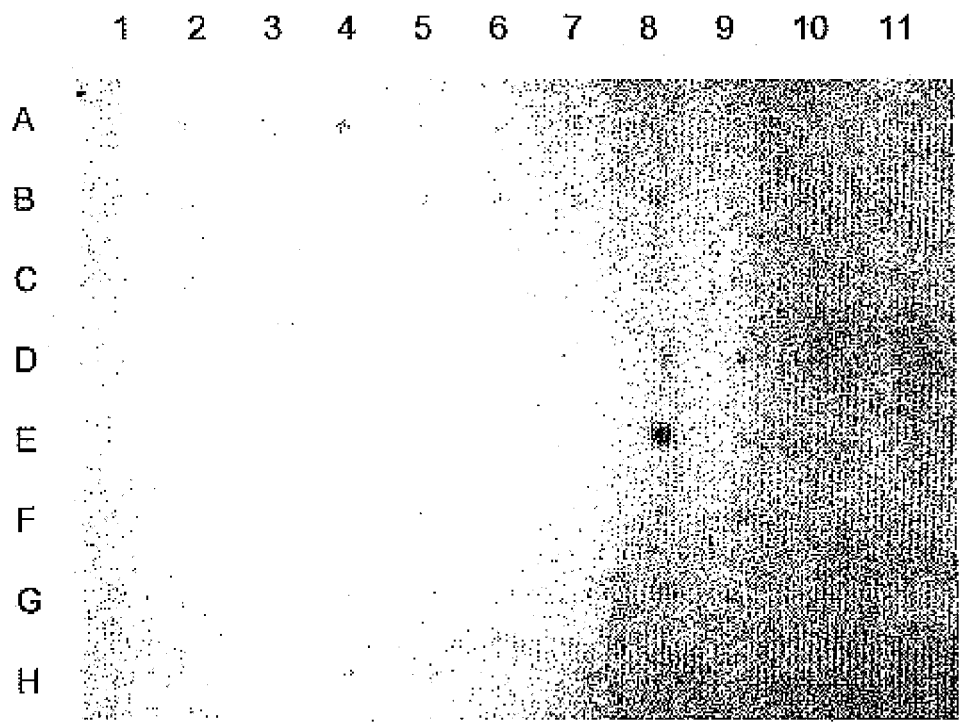
FIG. 7. An mRNA dot blot analysis of PHOR-1 expression in 76 different samples from human tissues showing expression exclusive to prostate. Positions represent the following tissues: A1 whole brain; A2 cerebellum, left; A3 substantia nigra; A4 heart; A5 esophagus; A6 colon, transverse; A7 kidney; A8 lung; A9 liver; A10 HL60, leukemia; A11 fetal brain; B1 cerebral cortex; B2 cerebellum, right; B3 accumbens nucleus; B4 aorta; B5 stomach; B6 colon, descending; B7 skeletal muscle; B8 placenta; B9 pancreas; B10 HeLa, S3; B11 fetal heart; C1 frontal lobe; C2 corpus callosum; C3 thalamus; C4 atrium, left; C5 duodenum; C6 rectum; C7 spleen; C8 bladder; C9 adrenal gland; C10 (562, leukemia; C11 fetal kidney; D1 parietal lobe; D2 amygdala; D3 pituitary gland; D4 atrium, right; D5 jejunum; D6--; D7 thymus; D8 uterus; D9 thyroid gland; D10 MOLT-4, leukemia; D11 fetal liver; E1 occipital lobe; E2 caudate nucleus; E3 spinal cord; E4 ventricle, left; E5 ileum; E6--; E7 leukocytes; E8 prostate; E9 salivary gland; E10 RAJI, lymphoma; E11 fetal spleen; F1 temporal lobe; F2 hippocampus; F3--; F4 ventricle, right; F5 ileocecum; F6--; F7 lymph node; F8 testis; F9 mammary gland; F10 DAUDI, lymphoma; F11 fetal thymus; G1 paracentral gyrus; G2 medulla oblongata; G3 --; G4 interventricular septum; G5 appendix; G6--; G7 bone marrow; G8 ovary; G9--; G10 SW480, colon cancer; G11 fetal lung; H1 pons; H2 putamen; H3--; H4 apex of the heart; H5 colon, ascending; H6--; H7 trachea; H8--; H9--; H10 A549, lung cancer; H11 --.

PHOR-1 expression is essentially prostate-specific in normal adult human tissues (FIGS. 5–7), with very low level expression detectable by RT-PCR in normal ovary as well as very low level expression detectable by RNA dot blot in heart tissue. In prostate cancer, PHOR-1 is expressed in tumor xenografts passaged in SCID mice as well as tumor samples biopsied from advanced prostate cancer patients (FIGS. 5–7). Comparisons of the expression of PHOR-1 in matched sets of tumor tissue versus adjacent normal tissues taken from advanced prostate cancer patients and patients with kidney, uterine, cervical, stomach and rectal cancer, showed very high level over-expression in the vast majority of patients (FIGS. 8–10), indicating high level upregulation in tumor tissues.

Isolation of Phor-1-Encoding Nucleic Acid Molecules

The PHOR-1 cDNA sequences described herein enable the isolation of other polynucleotides encoding PHOR-1 gene product(s), as well as the isolation of polynucleotides encoding PHOR-1 gene product homologues, alternatively spliced isoforms, allelic variants, and mutant forms of the PHOR-1 gene product. Various molecular cloning methods that can be employed to isolate full length cDNAs encoding a PHOR-1 gene are well known (See, for example, Sambrook, J. et al. Molecular Cloning: A Laboratory Manual, 2d edition., Cold Spring Harbor Press, New York, 1989; Current Protocols in Molecular Biology. Ausubel et al., Eds., Wiley and Sons, 995). For example, lambda phage cloning methodologies may be conveniently employed, using commercially available cloning systems (e.g., Lambda ZAP Express, Stratagene). Phage clones containing PHOR-1 gene cDNAs may be identified by probing with labeled PHOR-1 cDNA or a fragment thereof For example, in one embodiment, the PHOR-1 cDNA (FIGS. 1A–D; SEQ ID NO: 1) or a portion thereof can be synthesized and used as a probe to retrieve overlapping and full length cDNAs corresponding to a PHOR-1 gene. The PHOR-1 gene itself may be isolated by screening genomic DNA libraries, bacterial artificial chromosome libraries (BACs), yeast artificial chromosome libraries (YACs), and the like, with PHOR-1 DNA probes or primers.

Recombinant DNA Molecules and Host-Vector Systems

The invention also provides recombinant DNA or RNA molecules containing a PHOR-1 polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, for example, Sambrook et al, 1989, supra).

The invention further provides a host-vector system comprising a recombinant DNA molecule containing a PHOR-1 polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 cell). Examples of suitable mammalian cells include various prostate cancer cell lines such LNCaP, PC-3, DU145, LAPC-4, TsuPr1, other transfectable or transducible prostate cancer cell lines, as well as a number of mammalian cells routinely used for the expression of recombinant proteins (e.g., COS, CHO, 293, 293T cells). More particularly, a polynucleotide comprising the coding sequence of a PHOR-1 may be used to generate PHOR-1 proteins or fragments thereof using any number of host vector systems routinely used and widely known in the art.

A wide range of host vector systems suitable for the expression of PHOR-1 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, PHOR-1 may be preferably expressed in several prostate cancer and non-prostate cell lines, including for example 293, 293T, rat-1, 3T3, PC-3, LNCaP and TsuPr1. The host vector systems of the invention are useful for the production of a PHOR-1 protein or fragment thereof. Such host-vector systems may be employed to study the functional properties of PHOR-1 and PHOR-1 mutations.

Proteins encoded by the PHOR-1 genes, or by fragments thereof, will have a variety of uses, including but not limited to generating antibodies and in methods for identifying ligands and other agents and cellular constituents that bind to a PHOR-1 gene product. Antibodies raised against a PHOR-1 protein or fragment thereof may be useful in diagnostic and prognostic assays, imaging methodologies (including, particularly, cancer imaging), and therapeutic methods in the management of human cancers characterized by expression of a PHOR-1 protein, including but not limited to cancer of the prostate. Various immunological assays useful for the detection of PHOR-1 proteins are contemplated, including but not limited to various types of radioimmunoassays, enzyme-linked immunosorbent assays (ELISA), enzyme-linked immunofluorescent assays (ELIFA), immunocytochemical methods, and the like. Such antibodies may be labeled and used as immunological imaging reagents capable of detecting prostate cells (e.g., in radioscintigraphic imaging methods). PHOR-1 proteins may also be particularly useful in generating cancer vaccines, as further described below.

Phor-1 Proteins

Another aspect of the present invention provides PHOR-1 proteins and polypeptide fragments thereof. The PHOR-1 proteins of the invention include those specifically identified herein, as well as allelic variants, conservative substitution variants and homologs to the extent that such variants and homologs can be isolated/generated and characterized without undue experimentation following the methods outlined below. Fusion proteins that combine parts of different PHOR-1 proteins or fragments thereof, as well as fusion proteins of a PHOR-1 protein and a heterologous polypeptide, are also included. Such PHOR-1 proteins will be collectively referred to as the PHOR-1 proteins, the proteins of the invention, or PHOR-1. As used herein, the term "PHOR-1 polypeptide" refers to a polypeptide fragment or a PHOR-1 protein of at least 10 amino acids, preferably at least 15 amino acids.

A specific embodiment of a PHOR-1 protein comprises a polypeptide having the amino acid sequence of human PHOR-1 as shown in FIGS. 1A–D (SEQ ID NO: 2), from amino acid residue number 1 through about amino acid residue number 317 as shown therein. Another specific embodiment of a PHOR-1 protein comprises a polypeptide having the amino acid sequence of human PHOR-1 as shown in FIGS. 1A–D (SEQ ID NO: 2), from about amino acid residue number 86 through about amino acid residue number 310 as shown therein. A specific embodiment of a PHOR-1 fragment comprises a peptide selected from the group comprising amino acids 1–14 of the PHOR-1 protein sequence shown in FIGS. 1A–D (MVDPNGNESSATYF; SEQ ID NO: 8), amino acids 262–274 of the PHOR-1 protein sequence shown in FIGS. 1A–D (VHRFSKRRDSPLP; SEQ ID NO: 9), and the extracellular portions of PHOR-1 (amino acids 1–28, 86–99, 159–202 and 262–272 of SEQ ID NO: 2). Other specific embodiments include one or both of the transmembrane domains identified in FIGS. 1A–D (SEQ ID NO: 2).

In general, naturally occurring allelic variants of human PHOR-1 will share a high degree of structural identity and homology (e.g., 90% or more identity). Typically, allelic variants of the PHOR-1 proteins will contain conservative amino acid substitutions within the PHOR-1 sequences described herein or will contain a substitution of an amino acid from a corresponding position in a PHOR-1 homologue. One class of PHOR-1 allelic variants will be proteins that share a high degree of homology with at least a small region of a particular PHOR-1 amino acid sequence, but will further contain a radical departure from the sequence, such as a non-conservative substitution, truncation insertion or frame shift.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently b interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

PHOR-1 proteins, including variants, comprise at least one epitope in common with a PHOR-1 protein having the amino acid sequence of FIGS. 1A–D (SEQ ID NO: 2), such that an antibody that specifically binds to a PHOR-1 protein or variant will also specifically bind to the PHOR-1 protein having the amino acid sequence of FIGS. 1A–D (SEQ ID NO: 2). One class of PHOR-1 protein variants shares 90% or more identity with the amino acid sequence of FIGS. 1A–D (SEQ ID NO: 2). A more specific class of PHOR-1 protein variants comprises an extracellular domain as identified in FIG. 4. Preferred PHOR-1 protein variants are capable of exhibiting one or more of the GPCR functions described herein, including, for example, the ability to modulate cytosolic cAMP concentration and tyrosine phosphorylation, and the ability to stimulate colony growth.

PHOR-1 proteins may be embodied in many forms, preferably in isolated form. As used herein, a protein is said to be "isolated" when physical, mechanical or chemical methods are employed to remove the PHOR-1 protein from cellular constituents that are normally associated with the protein. A skilled artisan can readily employ standard purification methods to obtain an isolated PHOR-1 protein. A purified PHOR-1 protein molecule will be substantially free of other proteins or molecules that impair the binding of PHOR-1 to antibody or other ligand. The nature and degree of isolation and purification will depend on the intended use. Embodiments of a PHOR-1 protein include a purified PHOR-1 protein and a functional, soluble PHOR-1 protein. In one form, such functional, soluble PHOR-1 proteins or fragments thereof retain the ability to bind antibody or other ligand.

The invention also provides PHOR-1 polypeptides comprising biologically active fragments of the PHOR-1 amino acid sequence, such as a polypeptide corresponding to part of the amino acid sequences for PHOR-1 as shown in FIGS. 1A–D (SEQ ID NO: 2). Such polypeptides of the invention exhibit properties of the PHOR-1 protein, such as the ability to elicit the generation of antibodies that specifically bind an epitope associated with the PHOR-1 protein.

Embodiments of the invention disclosed herein include a wide variety of art accepted variants of PHOR-1 proteins such as polypeptides having amino acid insertions, deletions and substitutions. PHOR-1 variants can be made using methods known in the art such as site-directed mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., Gene, 34:315 (1985)], restriction selection mutagenesis [Wells et al., *Philos. Trans. R. Soc.*

London SerA, 317:415 (1986)] or other known techniques can be performed on the cloned DNA to produce the PHOR-1 variant DNA. Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W.H. Freeman & Co., N.Y.); Chothia, J. Mol. Biol., 150:1 (1976)]. If alanine substitution does not yield adequate amounts of variant, an isosteric amino acid can be used.

As discussed above, embodiments of the claimed invention include polypeptides containing less than the 317 amino acid sequence of the PHOR-1 protein shown in FIGS. 1A–D (SEQ ID NO: 2). For example, representative embodiments of the invention disclosed herein include polypeptides consisting of about amino acid 1 to about amino acid 10 of the PHOR-1 protein shown in FIGS. 1A–D (SEQ ID NO: 2), polypeptides consisting of about amino acid 20 to about amino acid 30 of the PHOR-1 protein shown in FIGS. 1A–D (SEQ ID NO: 2), polypeptides consisting of about amino acid 30 to about amino acid 40 of the PHOR-1 protein shown in FIGS. 1A–D (SEQ ID NO: 2), polypeptides consisting of about amino acid 40 to about amino acid 50 of the PHOR-1 protein shown in FIGS. 1A–D (SEQ ID NO: 2), polypeptides consisting of about amino acid 50 to about amino acid 60 of the PHOR-1 protein shown in FIGS. 1A–D (SEQ ID NO: 2), polypeptides consisting of about amino acid 60 to about amino acid 70 of the PHOR-1 protein shown in FIGS. 1A–D (SEQ ID NO: 2), polypeptides consisting of about amino acid 70 to about amino acid 80 of the PHOR-1 protein shown in FIGS. 1A–D (SEQ ID NO: 2), polypeptides consisting of about amino acid 80 to about amino acid 90 of the PHOR-1 protein shown in FIGS. 1A–D (SEQ ID NO: 2) and polypeptides consisting of about amino acid 90 to about amino acid 100 of the PHOR-1 protein shown in FIGS. 1A–D (SEQ ID NO: 2), etc. Following this scheme, polypeptides consisting of portions of the amino acid sequence of amino acids 100–317 of the PHOR-1 protein arc typical embodiments of the invention. Polypeptides consisting of larger portions of the PHOR-1 protein are also contemplated. For example polypeptides consisting of about amino acid 1 (or 20 or 30 or 40 etc.) to about amino acid 20, (or 30, or 40 or 50 etc.) of the PHOR-1 protein shown in FIGS. 1A–D (SEQ ID NO: 2) may be generated by a variety of techniques well known in the art.

Additional illustrative embodiments of the invention disclosed herein include PHOR-1 polypeptides containing the amino acid residues of one or more of the biological motifs contained within the PHOR-1 polypeptide sequence as shown in FIGS. 1A–D (SEQ ID NO: 2). In one embodiment, typical polypeptides of the invention can contain one or more of the regions of PHOR-1 that exhibit homology to HPRAJ70 and/or RA1c. In another embodiment, typical polypeptides of the invention can contain one or more of the PHOR-1 N-glycosylation sites such as NESS (SEQ ID NO: 10) at residues 7–10 (numbering from first amino acid residue shown in SEQ ID NO: 2), NLTI (SEQ ID NO: 11) at residues 44–47 and/or NSTT at residues 90–93 (SEQ ID NO: 12). In another embodiment, typical polypeptides of the invention can contain one or more of the PHOR-1 cAMP phosphorylation sites such as RRDS at residues 268–271 (SEQ ID NO: 13). In another embodiment, typical polypeptides of the invention can contain one or more of the PHOR-1 protein kinase C phosphorylation sites such as SKR at residues 266–268. In another embodiment, typical polypeptides of the invention can contain one or more of the PHOR-1 casein kinase II phosphorylation sites such as SLHE at residues 56–59 (SEQ ID NO: 14), SGID at residues 69–72 (SEQ ID NO: 15), and/or SGME at residues 110–113 (SEQ ID NO: 16). In another embodiment, typical polypeptides of the invention can contain one or more of the N-myristoylation sites such as GNESSA at residues 6–11 (SEQ ID NO: 17), GLEEAQ at residues 21–26 (SEQ ID NO: 18), GMESTV at residues 111–116 (SEQ ID NO: 19), and/or GTCVSH at residues 240–245 (SEQ ID NO: 20). In another embodiment, typical polypeptides of the invention can contain one or more of the GPCR signature sequences, such as amino acid residues 112–128 of SEQ ID NO: 2, and/or one or more of the olfactory receptor signature sequences, such as amino acid residues 61–82 and/or 239–254 of SEQ ID NO: 2. Related embodiments of these inventions include polypeptides containing combinations of the different motifs discussed above with preferable embodiments being those that contain no insertions, deletions or substitutions either within the motifs or the intervening sequences of these polypeptides.

PHOR-1 polypeptides can be generated using standard peptide synthesis technology or using chemical cleavage methods well known in the art based on the amino acid sequences of the human PHOR-1 proteins disclosed herein. Alternatively, recombinant methods can be used to generate nucleic acid molecules that encode a polypeptide fragment of a PHOR-1 protein. In this regard, the PHOR-1-encoding nucleic acid molecules described herein provide means for generating defined fragments of PHOR-1 proteins. PHOR-1 polypeptides are particularly useful in generating and characterizing domain specific antibodies (e.g., antibodies recognizing an extracellular or intracellular epitope of a PHOR-1 protein), in identifying agents or cellular factors that bind to PHOR-1 or a particular structural domain thereof, and in various therapeutic contexts, including but not limited to cancer vaccines. PHOR-1 polypeptides containing particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments containing such structures are particularly useful in generating subunit specific anti-PHOR-1 antibodies or in identifying cellular factors that bind to PHOR-1.

In a specific embodiment described in the examples that follow, a secreted form of PHOR-1 may be conveniently expressed in 293T cells transfected with a CMV-driven expression vector encoding PHOR-1 with a C-terminal 6XHis and MYC tag (pcDNA3.1/mycHIS, Invitrogen). The secreted HIS-tagged PHOR-1 in the culture media may be purified using a nickel column and standard techniques. Alternatively, an AP-tag system may be used. Various constructs for expression of PHOR-1 are described in the examples below.

Modifications of PHOR-1 such as covalent modifications are included within the scope of this invention. One type of covalent modification includes reacting targeted amino acid residues of an PHOR-1 polypeptide with an organic derivatizing agent that is capable of reacting with selected side chains or the N- or C- terminal residues of the PHOR-1.

Another type of covalent modification of the PHOR-1 polypeptide included within the scope of this invention comprises altering the native glycosylation pattern of the polypeptide. "Altering the native glycosylation pattern" is intended for purposes herein to mean deleting one or more carbohydrate moieties found in native sequence PHOR-1 (either by removing the underlying glycosylation site or by deleting the glycosylation by chemical and/or enzymatic means), and/or adding one or more glycosylation sites that are not present in the native sequence PHOR-1. In addition, the phrase includes qualitative changes in the glycosylation of the native proteins, involving a change in the nature and proportions of the various carbohydrate moieties present. Another type of covalent modification of PHOR-1 comprises linking the PHOR-1 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,49.6,689; 4,301,144; 4,670,417; 4,791,192 or 4,179,337.

The PHOR-1 of the present invention may also be modified in a way to form a chimeric molecule comprising PHOR-1 fused to another, heterologous polypeptide or amino acid sequence. In one embodiment, such a chimeric molecule comprises a fusion of the PHOR-1 with a polyhistidine epitope tag, which provides an epitope to which immobilized nickel can selectively bind. The epitope tag is generally placed at the amino- or carboxyl-terminus of the PHOR-1. In an alternative embodiment, the chimeric molecule may comprise a fusion of the PHOR-1 with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an PHOR-1 polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

Phor-1 Antibodies

Another aspect of the invention provides antibodies that bind to PHOR-1 proteins and polypeptides. The most preferred antibodies will selectively bind to a PHOR-1 protein and will not bind (or will bind weakly) to non-PHOR-1 proteins and polypeptides. Anti-PHOR-1 antibodies that are particularly contemplated include monoclonal and polyclonal antibodies as well as fragments containing the antigen-binding domain and/or one or more complementarity determining regions of these antibodies. As used herein, an antibody fragment is defined as at least a portion of the variable region of the immunoglobulin molecule that binds to its target, i.e., the antigen binding region.

For some applications, it may be desirable to generate antibodies that specifically react with a particular PHOR-1 protein and/or an epitope within a particular structural domain. For example, preferred antibodies useful for cancer therapy and diagnostic imaging purposes are those which react with an epitope in an extracellular region of the PHOR-1 protein as expressed in cancer cells. Such antibodies may be generated by using the PHOR-1 proteins described herein, or using peptides derived from predicted extracellular domains thereof, as an immunogen. In this regard, with reference to the PHOR-1 protein sequence shown in FIG. 1, regions in the sequence amino-terminal to the transmembrane domain may be selected and used to design appropriate immunogens and screening reagents for raising and selecting extracellular-specific PHOR-1 antibodies.

PHOR-1 antibodies of the invention may be particularly useful in prostate cancer therapeutic strategies, diagnostic and prognostic assays, and imaging methodologies. Similarly, such antibodies may be useful in the treatment, diagnosis, and/or prognosis of other cancers, to the extent PHOR-1 is also expressed or overexpressed in other types of cancer. The invention provides various immunological assays useful for the detection and quantification of PHOR-1 and mutant PHOR-1 proteins and polypeptides. Such assays generally comprise one or more PHOR-1 antibodies capable of recognizing and binding a PHOR-1 or mutant PHOR-1 protein, as appropriate, and may be performed within various immunological assay formats well known in the art, including but not limited to various types of radioimmunoassays, enzyme-linked immunosorbent assays (ELI SA), enzyme-linked immunofluorescent assays (ELIFA), and the like. In addition, immunological imaging methods capable of detecting prostate cancer are also provided by the invention, including but limited to radioscintigraphic imaging methods using labeled PHOR-1 antibodies. Such assays may be used clinically in the detection, monitoring, and prognosis of prostate cancer, particularly advanced prostate cancer.

PHOR-1 antibodies may also be used in methods for purifying PHOR-1 and mutant PHOR-1 proteins and polypeptides and for isolating PHOR-1 homologues and related molecules. For example, in one embodiment, the method of purifying a PHOR-1 protein comprises incubating a PHOR-1 antibody, which has been coupled to a solid matrix, with a lysate or other solution containing PHOR-1 under conditions which permit the PHOR-1 antibody to bind to PHOR-1; washing the solid matrix to eliminate impurities; and eluting the PHOR-1 from the coupled antibody. Other uses of the PHOR-1 antibodies of the invention include generating anti-idiotypic antibodies that mimic the PHOR-1 protein.

PHOR-1 antibodies may also be used therapeutically by, for example, modulating or inhibiting the biological activity of a PHOR-1 protein or targeting and destroying cancer cells expressing a PHOR-1 protein. Antibody therapy of prostate and other cancers is more specifically described in a separate subsection below.

Various methods for the preparation of antibodies are well known in the art. For example, antibodies may be prepared by immunizing a suitable mammalian host using a PHOR-1 protein, peptide, or fragment, in isolated or immunoconjugated form (Antibodies: A Laboratory Manual, CSH Press, Eds., Harlow, and Lane (1988); Harlow, Antibodies, Cold Spring Harbor Press, N.Y. (1989)). Examples of protein immunogens include recombinant PHOR-1 (expressed in a baculovirus system, mammalian system, etc.), PHOR-1 extracellular domain, AP-tagged PHOR-1, etc. In addition, fusion proteins of PHOR-1 may also be used, such as a fusion of PHOR-1 with GST, maltose-binding protein (MBP), green fluorescent protein (GFP), HisMax-TOPO or MycHis (see Examples below).

In a particular embodiment, a GST fusion protein comprising all or most of the open reading frame amino acid sequence of FIGS. 1A–D (SEQ ID NO: 2) may be produced and used as an immunogen to generate appropriate antibodies. Cells expressing or overexpressing PHOR-1 may also be used for immunizations. Similarly, any cell engineered to express PHOR-1 may be used. Such strategies may result in the production of monoclonal antibodies with enhanced capacities for recognizing endogenous PHOR-1. Another useful immunogen comprises PHOR-1 peptides linked to the plasma membrane of sheep red blood cells.

The amino acid sequence of PHOR-1 as shown in FIGS. 1A–D (SEQ ID NO: 2) may be used to select specific regions of the PHOR-1 protein for generating antibodies. For example, hydrophobicity and hydrophilicity analyses of the PHOR-1 amino acid sequence may be used to identify hydrophilic regions in the PHOR-1 structure. Regions of the PHOR-1 protein that show immunogenic structure, as well as other regions and domains, can readily be identified using various other methods known in the art, such as Chou-Fasman, Garnier Robson, Kyte-Doolittle, Eisenberg, Karplus-Schultz or Jameson-Wolf analysis. Peptides of PHOR-1 predicted to bind HLA-A2 may be selected for the generation of antibodies. As discussed in the examples below, immunogenicity has been demonstrated with amino acids 1–14 (MVDPNGNESSATYF; SEQ ID NO: 8), amino acids 262–274 (VHRFSKRRDSPLP; SEQ ID NO: 9) and amino acids 86–310 of the PHOR-1 protein sequence (SEQ ID NO: 2), which were used to generate polyclonal and monoclonal antibodies using rabbits and mice, respectively. This B cell response (antibody production) is the result of an initial T cell response elicited by the immunogenic portions of PHOR-1.

Methods for preparing a protein or polypeptide for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a PHOR-1 immunogen is conducted generally by injection over a suitable period and with use of a suitable adjuvant, as is generally understood in the art. During the immunization schedule, titers of antibodies can be taken to determine adequacy of antibody formation.

PHOR-1 monoclonal antibodies are preferred and may be produced by various means well known in the art. For example, immortalized cell lines which secrete a desired monoclonal antibody may be prepared using the standard hybridoma technology of Kohler and Milstein or modifications which immortalize producing B cells, a is generally known. The immortalized cell lines secreting the desired antibodies are screened by immunoassay in which the antigen is the PHOR-1 protein or PHOR-1 fragment. When the appropriate immortalized cell culture secreting the desired antibody is identified, the cells may be expanded and antibodies produced either from in vitro cultures or from ascites fluid.

The antibodies or fragments may also be produced, using current technology, by recombinant means. Regions that bind specifically to the desired regions of the PHOR-1 protein can also be produced in the context of chimeric or CDR grafted antibodies of multiple species origin. Humanized or human PHOR-1 antibodies may also be produced and are preferred for use in therapeutic contexts. Methods for humanizing murine and other non-human antibodies by substituting one or more of the non-human antibody CDRs for corresponding human antibody sequences are well known (see for example, Jones et al., 1986, Nature 321: 522–525; Riechmann et al., 1988, Nature 332: 323–327; Verhoeyen et al., 1988, Science 239:1534–1536). See also, Carter et al., 1993, Proc. Nat'l Acad. Sci. USA 89: 4285 and Sims et al., 1993,J. Immunol. 151: 2296. Methods for producing fully human monoclonal antibodies include phage display and transgenic animal technologies (for review, see Vaughan et al., 1998, Nature Biotechnology 16: 535–539).

Fully human PHOR-1 monoclonal antibodies may be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45–64 (1993); Burton and Barbas, Human Antibodies from combinatorial libraries. Id., pp 65–82). Fully human PHOR-1 monoclonal antibodies may also be produced using transgenic mice engineered to contain human immunoglobulin gene loci as described in PCT Patent Application W098/24893, Kucherlapati and Jakobovits et al., published Dec. 3, 1997 (see also, Jakobovits, 1998, Exp. Opin. Invest. Drugs 7(4): 607–614). This method avoids the in vitro manipulation required with phage display technology and efficiently produces high affinity authentic human antibodies.

Reactivity of PHOR-1 antibodies with a PHOR-1 protein may be established by a number of well known means, including western blot, immunoprecipitation, ELISA, and FACS analyses using, as appropriate, PHOR-1 proteins, peptides, PHOR-1 expressing cells or extracts thereof.

A PHOR-1 antibody or fragment thereof of the invention may be labeled with a detectable marker or conjugated to a second molecule, such as a cytotoxin or other therapeutic agent, and used for targeting the second molecule to a PHOR-1 positive cell (Vitetta, E. S. et al., 1993, Immunotoxin therapy, in DeVita, Jr., V. T. et al., eds., Cancer: Principles and Practice of Oncology, 4th ed., J.B. Lippincott Co., Philadelphia, 2624–2636). Examples of cytotoxic agents include, but are not limited to ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha-sarcin, gelonin, mitogellin, retstrictocin, phenomycin, enomycin, curicin, crotin, calicheamicin, sapaonaria officinalis inhibitor, and glucocorticoid and other chemotherapeutic agents, as well as radioisotopes such as $^{212}Bi$, $^{131}I$, $^{131}In$, 90Y, and $^{186}Re$. Suitable detectable markers include, but are not limited to, a radioisotope, a fluorescent compound, a bioluminescent compound, chemiluminescent compound, a metal chelator or an enzyme. Antibodies may also be conjugated to an anti-cancer pro-drug activating enzyme capable of converting the pro-drug to its active form. See, for example, U.S. Pat. No. 4,975,287.

Further, bi-specific antibodies specific for two or more PHOR-1 epitopes may be generated using methods generally known in the art. Further, antibody effector functions may be modified to enhance the therapeutic effect of PHOR-1 antibodies on cancer cells. For example, cysteine residues may be engineered into the Fc region, permitting the formation of interchain disulfide bonds and the generation of homodimers which may have enhanced capacities for internalization, ADCC and/or complement mediated cell killing (see, for example, Caron et al., 1992, J. Exp. Med. 176: 1191–1195; Shopes, 1992, J. Immunol. 148: 2918–2922). Homodimeric antibodies may also be generated by cross-linking techniques known in the art (e.g., Wolff et al., Cancer Res. 53: 2560–2565).

Phor-1 Transgenic Animals

Nucleic acids that encode PHOR-1 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA that is integrated into the genome of a cell from which a transgenic animal develops. In one embodiment, cDNA encoding PHOR-1 can be used to clone genomic DNA encoding PHOR-1 in accordance with established techniques and the genomic sequences used to generate transgenic animals that contain cells that express DNA encoding PHOR-1.

Methods for generating transgenic animals, particularly animals such as mice or rats, have become conventional in the art and are described, for example, in U.S. Pat. Nos. 4,736,866 and 4,870,009. Typically, particular cells would be targeted for PHOR-1 transgene incorporation with tissue-specific enhancers. Transgenic animals that include a copy of a transgene encoding PHOR-1 introduced into the germ line of the animal at an embryonic stage can be used to examine the effect of increased expression of DNA. encoding PHOR-1. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PHOR-1 can be used to construct a PHOR-1 "knock out" animal that has a defective or altered gene encoding PHOR-1 as a result of homologous recombination between the endogenous gene encoding PHOR-1 and altered genomic DNA encoding PHOR-1 introduced into an embryonic cell of the animal. For example, cDNA encoding PHOR-1 can be used to clone genomic DNA encoding PHOR-1 in accordance with established techniques. A portion of the genomic DNA encoding PHOR-1 can be deleted or replaced with another gene, such as a gene encoding a selectable marker that can be used to monitor integration.

Typically, several kilobases of unaltered flanking DNA (both at the 5' and 3' ends) are included in the vector (see e.g., Thomas and Capecchi, 1987, Cell 51:503 for a description of homologous recombination vectors). The vector is introduced into an embryonic stem cell line (e.g., by electroporation) and cells in which the introduced DNA has homologously recombined with the endogenous DNA are selected (see e.g., Li et al., 1992, Cell 69:915). The selected cells are then injected into a blastocyst of an animal (e.g., a mouse or rat) to form aggregation chimeras (see e.g., Bradley, in *Teratocarcinomas and Embryonic Stem Cells: A Practical Approach*, E. J. Robertson, ed., IRL, Oxford, 1987, pp. 113–152).

A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the PHOR-1 polypeptide.

Methods for the Detection of Phor-1

Another aspect of the present invention relates to methods for detecting PHOR-1 polynucleotides and PHOR-1 proteins and variants thereof, as well as methods for identifying a cell that expresses PHOR-1. The highly tissue-restricted expression pattern of PHOR-1 suggests that this molecule can serve as a diagnostic marker for metastasized disease. In this context, the status of PHOR-1 gene products may provide information useful for predicting a variety of factors including susceptibility to advanced stage disease, rate of progression, and/or tumor aggressiveness. As discussed in detail below, the status of PHOR-1 gene products in patient samples may be analyzed by a variety protocols that are well known in the art including immunohistochemical analysis, the variety of northern blotting techniques including in situ hybridization, RT-PCR analysis (for example on laser capture micro-dissected samples), western blot analysis and tissue array analysis.

More particularly, the invention provides assays for the detection of PHOR-1 polynucleotides in a biological sample, such as prostate tissue, kidney tissue, uterine tissue, cervical specimen, stomach tissue, rectal tissue, bone tissue, lymphatic tissue and other tissues, urine, semen, blood or serum, cell preparations, and the like. Detectable PHOR-1 polynucleotides include, for example, a PHOR-1 gene or fragments thereof, PHOR-1 mRNA, alternative splice variant PHOR-1 mRNAs, and recombinant DNA or RNA molecules containing a PHOR-1 polynucleotide. A number of methods for amplifying and/or detecting the presence of PHOR-1 polynucleotides are well known in the art and may be employed in the practice of this aspect of the invention.

In one embodiment, a method for detecting a PHOR-1 mRNA in a biological sample comprises producing cDNA from the sample by reverse transcription using at least one primer; amplifying the cDNA so produced using PHOR-1 polynucleotides as sense and antisense primers to amplify PHOR-1 cDNAs therein; and detecting the presence of the amplified PHOR-1 cDNA. Optionally, the sequence of the amplified PHOR-1 cDNA can be determined. In another embodiment, a method of detecting a PHOR-1 gene in a biological sample comprises first isolating genomic DNA from the sample; amplifying the isolated genomic DNA using PHOR-1 polynucleotides as sense and antisense primers to amplify the PHOR-1 gene therein; and detecting the presence of the amplified PHOR-1 gene. Any number of appropriate sense and antisense probe combinations may be designed from the nucleotide sequences provided for the PHOR-1 (FIGS. 1A–D; SEQ ID NO: 1) and used for this purpose.

The invention also provides assays for detecting the presence of a PHOR-1 protein in a tissue of other biological sample such as serum, bone, prostate, and other tissues, urine, cell preparations, and the like, as well as cytological assays for detection of cells expressing PHOR-1. Methods for detecting a PHOR-1 protein are also well known and include, for example, immunoprecipitation, immunohistochemical analysis, western blot analysis, molecular and cellular binding assays, ELISA, ELIFA and the like. For example, in one embodiment, a method of detecting the presence of a PHOR-1 protein in a biological sample comprises first contacting the sample with a PHOR-1 antibody, a PHOR-1-reactive fragment thereof, or a recombinant protein containing an antigen binding region of a PHOR-1 antibody; and then detecting the binding of PHOR-1 protein in the sample thereto.

Methods for identifying a cell that expresses PHOR-1 are also provided. In one embodiment, an assay for identifying a cell that expresses a PHOR-1 gene comprises detecting the presence of PHOR-1 mRNA in the cell. Methods for the detection of particular mRNAs in cells are well known and include, for example, hybridization assays using complementary DNA probes (such as in situ hybridization using labeled PHOR-1 riboprobes, northern blot and related techniques) and various nucleic acid amplification assays (such as RT-PCR using complementary primers specific for PHOR-1, and other amplification type detection methods, such as, for example, branched DNA, SISBA, TMA and the like). Alternatively, an assay for identifying a cell that expresses a PHOR-1 gene comprises detecting the presence of PHOR-1 protein in the cell or secreted by the cell. Various methods for the detection of proteins are well known in the art and may be employed for the detection of PHOR-1 proteins and PHOR-1 expressing cells.

PHOR-1 expression analysis may also be useful as a tool for identifying and evaluating agents that modulate PHOR-1 gene expression. For example, PHOR-1 expression is restricted to normal prostate, as well as to cancers of the prostate, kidney, uterus, cervix, stomach and rectum, and PHOR-1 may also be expressed in other cancers. Identification of a molecule or biological agent that could inhibit PHOR-1 expression or over-expression in cancer cells may be of therapeutic value. Such an agent may be identified by using a screen that quantifies PHOR-1 expression by RT-PCR, nucleic acid hybridization or antibody binding.

Monitoring the Status of Phor-1 and its Products

Assays that evaluate the status of the PHOR-1 gene and PHOR-1 gene products in an individual may provide information on the growth or oncogenic potential of a biological sample from this individual. For example, because PHOR-1 mRNA is so highly expressed in prostate, kidney, uterine, cervical, stomach and rectal cancers, and not in most normal tissue, assays that evaluate the relative levels of PHOR-1 mRNA transcripts or proteins in a biological sample may be used to diagnose a disease associated with PHOR-1 dysregulation, such as cancer, and may provide prognostic information useful in defining appropriate therapeutic options. Similarly, assays that evaluate the integrity PHOR-1 nucleotide and amino acid sequences in a biological sample, may also be used in this context.

The finding that PHOR-1 mRNA is so highly expressed in prostate cancers, and not in most normal tissue, provides evidence that this gene is associated with dysregulated cell growth and therefore identifies this gene and its products as targets that the skilled artisan can use to evaluate biological samples from individuals suspected of having a disease associated with PHOR-1 dysregulation. In another example, because the expression of PHOR-1 is normally restricted to prostate, one can also evaluate biological samples taken from other tissues to detect PHOR-1 expression as an indication of metastasis. In this context, the evaluation of the expression status of PHOR-1 gene and its products can be used to gain information on the disease potential of a tissue sample. The terms "expression status" in this context is used to broadly refer to the variety of factors involved in the expression, function and regulation of a gene and its products such as the level of mRNA expression, the integrity of the expressed gene products (such as the nucleic and amino acid sequences) and transcriptional and translational modifications to these molecules.

The expression status of PHOR-1 may provide information useful for predicting susceptibility to particular disease stages, progression, and/or tumor aggressiveness. The invention provides methods and assays for determining PHOR-1 expression status and diagnosing cancers that express PHOR-1, such as cancers of the prostate, breast, bladder, lung, bone, colon, pancreatic, testicular, cervical and ovarian cancers. PHOR-1 expression status in patient samples may be analyzed by a number of means well known in the art, including without limitation, immunohistochemical analysis, in situ hybridization, RT-PCR analysis on laser capture micro-dissected samples, western blot analysis of clinical samples and cell lines, and tissue array analysis. Typical protocols for evaluating the expression status of the PHOR-1 gene and gene products can be found, for example in *Current Protocols In Molecular Biology*, Units 2 [Northern Blotting], 4 [Southern Blotting], 15 [Immunoblotting] and 18 [PCR Analysis], Frederick M. Ausubul et al. eds., 1995.

In one aspect, the invention provides methods for monitoring PHOR-1 gene products by determining the status of PHOR-1 gene products expressed by cells in a test tissue sample from an individual suspected of having a disease associated with dysregulated cell growth (such as hyperplasia or cancer) and then comparing the status so determined to the status of PHOR-1 gene products in a corresponding normal sample, the presence of aberrant PHOR-1 gene products in the test sample relative to the normal sample providing an indication of the presence of dysregulated cell growth within the cells of the individual.

In another aspect, the invention provides assays useful in determining the presence of cancer in an individual, comprising detecting a significant increase in PHOR-1 mRNA or protein expression in a test cell or tissue sample relative to expression levels in the corresponding normal cell or tissue. The presence of PHOR-1 mRNA may, for example, be evaluated in tissue samples including but not limited to colon, lung, prostate, pancreas, bladder, breast, ovary, cervix, testis, head and neck, brain, stomach, bone, etc. The presence of significant PHOR-1 expression in any of these tissues may be useful to indicate the emergence, presence and/or severity of these cancers or a metastasis of cancer originating in another tissue, since the corresponding normal tissues do not express PHOR-1 mRNA or express it at lower levels.

In a related embodiment, PHOR-1 expression status may be determined at the protein level rather than at the nucleic acid level. For example, such a method or assay would comprise determining the level of PHOR1 protein expressed by cells in a test tissue sample and comparing the level so determined to the level of PHOR-1 expressed in a corresponding normal sample. In one embodiment, the presence of PHOR-1 protein is evaluated, for example, using immunohistochemical methods. PHOR-1 antibodies or binding partners capable of detecting PHOR-1 protein expression may be used in a variety of assay formats well known in the art for this purpose.

In other related embodiments, one can evaluate the integrity PHOR-1 nucleotide and amino acid sequences in a biological sample in order to identify perturbations in the structure of these molecules such as insertions, deletions, substitutions and the like. Such embodiments are useful because perturbations in the nucleotide and amino acid sequences are observed in a large number of proteins associated with a growth dysregulated phenotype (see e.g. Marrogi et al., J. Cutan. Pathol. 26(8): 369–378 (1999)). In this context, a wide variety of assays for observing perturbations in nucleotide and amino acid sequences are well known in the art. For example, the size and structure of nucleic acid or amino acid sequences of PHOR-1 gene products may be observed by the northern, Southern, western, PCR and DNA sequencing protocols discussed herein. In addition, other methods for observing perturbations in nucleotide and amino acid sequences such as single strand conformation polymorphism analysis are well known in the art (see e.g. U.S. Pat. Nos. 5,382,510 and 5,952,170).

In another embodiment, one can examine the methylation status of the PHOR-1 gene in a biological sample. Aberrant demethylation and/or hypermethylation of CpG islands in gene 5' regulatory regions frequently occurs in immortalized and transformed cells and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985–1992 (1999)). In addition, this alteration is present in at least 70% of cases of high-grade prostatic intraepithelial neoplasia (PIN) (Brooks et al, Cancer Epidemiol. Biomarkers Prev., 1998, 7:531–536).

In another example, expression of the LAGE-I tumor specific gene (which is not expressed in normal prostate but is expressed in 25–50% of prostate cancers) is induced by deoxy-azacytidine in lymphoblastoid cells, suggesting that tumoral expression is due to demethylation (Lethe et al., 1998, Int. J. Cancer 76(6): 903–908). In this context, a variety of assays for examining methylation status of a gene are well known in the art. For example, one can utilize in Southern hybridization approaches methylation-sensitive restriction enzymes which can not cleave sequences that contain methylated CpG sites in order to assess the overall methylation status of CpG islands.

In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in *Current Protocols In Molecular Biology*, Units 12, Frederick M. Ausubel et al. eds., 1995.

In another related embodiment, the invention provides assays useful in determining the presence of cancer in an individual, comprising detecting a significant change in the PHOR-1 alternative splice variants expressed in a test cell or tissue sample relative to expression levels in the corresponding normal cell or tissue. The monitoring of alternative splice variants of PHOR-1 is useful because changes in the alternative splicing of proteins is suggested as one of the steps in a series of events that lead to the progression of cancers (see e.g. Carstens et al., Oncogene 15(250: 3059–3065 (1997)).

Gene amplification provides an additional method of assessing the status of PHOR-1. Gene amplification may be measured in a sample directly, for example, by conventional Southern blotting, northern blotting to quantitate the transcription of mRNA [Thomas, *Proc. Natl. Acad. Sci. USA*, 77:5201–5205 (1980)], dot blotting (DNA analysis), or in silu hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

In addition to the tissues discussed above, peripheral blood may be conveniently assayed for the presence of cancer cells, including but not limited to prostate cancers, using RT-PCR to detect PHOR-1 expression. The presence of RT-PCR amplifiable PHOR-1 mRNA provides an indication of the presence of the cancer. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25: 373–384; Ghossein et al., 1995, J. Clin. Oncol. 13: 1195–2000; Heston et al., 1995, Clin. Chem. 41: 1687–1688). RT-PCR assays are well known in the art.

A related aspect of the invention is directed to predicting susceptibility to developing cancer in an individual. In one embodiment, a method for predicting susceptibility to cancer comprises detecting PHOR-1 mRNA or PHOR-1 protein in a tissue sample, its presence indicating susceptibility to cancer, wherein the degree of PHOR-1 mRNA expression present is proportional to the degree of susceptibility. In a specific embodiment, the presence of PHOR-1 in prostate tissue is examined, with the presence of PHOR-1 in the sample providing an indication of prostate cancer susceptibility (or the emergence or existence of a prostate tumor). In a closely related embodiment, one can evaluate the integrity PHOR-1 nucleotide and amino acid sequences in a biological sample in order to identify perturbations in the structure of these molecules such as insertions, deletions, substitutions and the like, with the presence of one or more perturbations in PHOR-1 gene products in the sample providing an indication of cancer susceptibility (or the emergence or existence of a tumor).

Yet another related aspect of the invention is directed to methods for gauging tumor aggressiveness. In one embodiment, a method for gauging aggressiveness of a tumor comprises determining the level of PHOR-1 mRNA or PHOR-1 protein expressed by cells in a sample of the tumor, comparing the level so determined to the level of PHOR-1 mRNA or PHOR-1 protein expressed in a corresponding normal tissue taken from the same individual or a normal tissue reference sample, wherein the degree of PHOR-1 mRNA or PHOR-1 protein expression in the tumor sample relative to the normal sample indicates the degree of aggressiveness. In a specific embodiment, aggressiveness of prostate tumors is evaluated by determining the extent to which PHOR-1 is expressed in the tumor cells, with higher expression levels indicating more aggressive tumors. In a closely related embodiment, one can evaluate the integrity PHOR-1 nucleotide and amino acid sequences in a biological sample in order to identify perturbations in the structure of these molecules such as insertions, deletions, substitutions and the like, with the presence of one or more perturbations indicating more aggressive tumors.

Yet another related aspect of the invention is directed to methods for observing the progression of a malignancy in an individual over time. In one embodiment, methods for observing the progression of a malignancy in an individual over time comprise determining the level of PHOR-1 mRNA or PHOR-1 protein expressed by cells in a sample of the tumor, comparing the level so determined to the level of PHOR-1 mRNA or PHOR-1 protein expressed in an equivalent tissue sample taken from the same individual at a different time, wherein the degree of PHOR-1 mRNA or PHOR-1 protein expression in the tumor sample over time provides information on the progression of the cancer. In a specific embodiment, the progression of a cancer is evaluated by determining the extent to which PHOR-1 expression in the tumor cells alters over time, with higher expression levels indicating a progression of the cancer. In a closely related embodiment, one can evaluate the integrity PHOR-1 nucleotide and amino acid sequences in a biological sample in order to identify perturbations in the structure of these molecules such as insertions, deletions, substitutions and the like, with the presence of one or more perturbations indicating a progression of the cancer.

The above diagnostic approaches may be combined with any one of a wide variety of prognostic and diagnostic protocols known in the art. For example, another embodiment of the invention disclosed herein is directed to methods for observing a coincidence between the expression of PHOR-1 gene and PHOR-1 gene products (or perturbations in PHOR-1 gene and PHOR-1 gene products) and a factor that is associated with malignancy as a means of diagnosing and prognosticating the status of a tissue sample. In this context, a wide variety of factors associated with malignancy may be utilized such as the expression of genes otherwise associated with malignancy (including PSA, PSCA and PSM expression) as well as gross cytological observations (see e.g. Bocking et al., 1984, Anal. Quant. Cytol. 6(2):74–88; Eptsein, 1995, Hum. Pathol. 1995 February;26(2):223–9; Thorson et al., 1998, Mod. Pathol. 11 (6):543–51; Baisden et al., 1999, Am. J. Surg. Pathol. 23(8):918–24). Methods for observing a coincidence between the expression of PHOR-1 gene and PHOR-1 gene products (or perturbations in PHOR-1 gene and PHOR-1 gene products) and an additional factor that is associated with malignancy are useful, for example, because the presence of a set or constellation of specific factors that coincide provides information crucial for diagnosing and prognosticating the status of a tissue sample.

In a typical embodiment, methods for observing a coincidence between the expression of PHOR-1 gene and PHOR-1 gene products (or perturbations in PHOR-1 gene and PHOR-1 gene products) and a factor that is associated with malignancy entails detecting the overexpression of PHOR-1 mRNA or protein in a tissue sample, detecting the overexpression of PSA mRNA or protein in a tissue sample, and observing a coincidence of PHOR-1 mRNA or protein and PSA mRNA or protein overexpression. In a specific embodiment, the expression of PHOR-1 and PSA mRNA in prostate tissue is examined. In a preferred embodiment, the coincidence of PHOR-1 and PSA mRNA overexpression in the sample provides an indication of prostate cancer, prostate cancer susceptibility or the emergence or existence of a prostate tumor.

Methods for detecting and quantifying the expression of PHOR-1 mRNA or protein are described herein and use standard nucleic acid and protein detection and quantification technologies well known in the art. Standard methods for the detection and quantification of PHOR-1 mRNA include in situ hybridization using labeled PHOR-1 riboprobes, northern blot and related techniques using PHOR-1 polynucleotide probes, RT-PCR analysis using primers specific for PHOR-1, and other amplification type detection methods, such as, for example, branched DNA, SISBA, TMA and the like. In a specific embodiment, semi-quantitative RT-PCR may be used to detect and quantify PHOR-1 mRNA expression as described in the Examples that follow. Any number of primers capable of amplifying PHOR-1 may be used for this purpose, including but not limited to the various primer sets specifically described herein. Standard methods for the detection and quantification of protein may be used for this purpose. In a specific embodiment, polyclonal or monoclonal antibodies specifically reactive with the wild-type PHOR-1 protein may be used in an immunohistochemical assay of biopsied tissue.

Identifying Molecules that Interact with Phor-1

The PHOR-1 protein sequences disclosed herein allow the skilled artisan to identify proteins, small molecules and other agents that interact with PHOR-1 and pathways activated by PHOR-1 via any one of a variety of art accepted protocols. For example one can utilize one of the variety of so-called interaction trap systems (also referred to as the "two-hybrid assay"). In such systems, molecules that interact reconstitute a transcription factor and direct expression of a reporter gene, the expression of which is then assayed. Typical systems identify protein-protein interactions in vivo through reconstitution of a eukaryotic transcriptional activator and are disclosed for example in U.S. Pat. Nos. 5,955,280, 5,925,523, 5,846,722 and 6,004,746.

Alternatively one can identify molecules that interact with PHOR-1 protein sequences by screening peptide libraries. In such methods, peptides that bind to selected receptor molecules such as PHOR-1 are identified by screening libraries that encode a random or controlled collection of amino acids. Peptides encoded by the libraries are expressed as fusion proteins of bacteriophage coat proteins, and bacteriophage particles are then screened against the receptors of interest. Peptides having a wide variety of uses, such as therapeutic or diagnostic reagents, may thus be identified without any prior information on the structure of the expected ligand or receptor molecule. Typical peptide libraries and screening methods that can be used to identify molecules that interact with PHOR-1 protein sequences are disclosed for example in U.S. Pat. Nos. 5,723,286 and 5,733,731. Exemplary assays for identifying molecules that interact with or alter the function of a GPCR are described in Moon et al., 1999, PNAS 96(25):14605–14610; Breer et al., 1998, Ann. N.Y. Acad. Sci. 855:175–181; and Sinnett-Smith et al., 2000, J. Biol. Chem. 275(39):30644–30652.

Alternatively, cell lines expressing PHOR-1 can be used to identify protein-protein interactions mediated by PHOR-1. This possibility can be examined using immunoprecipitation techniques as shown by others (Hamilton B. J, et al. Biochem. Biophys. Res. Commun. 1999, 261:646–51). Typically PHOR-1 protein can be immunoprecipitated from PHOR-1 expressing prostate cancer cell lines using anti-PHOR-1 antibodies. Alternatively, antibodies against His-tag can be used in a cell line engineered to express PHOR-1 (vectors mentioned above). The immunoprecipitated complex can be examined for protein association by procedures such as western blotting, $^{35}$S-methionine labeling of proteins, protein microsequencing, silver staining and two dimensional gel electrophoresis.

Small molecules that interact with PHOR-1 can be identified through related embodiments of such screening assays. For example, small molecules can be identified that interfere with GPCR function, including molecules that interfere with PHOR-1's ability to mediate phosphorylation and de-phosphorylation, second messenger signaling and tumorigenesis. Typical methods are discussed for example in U.S. Pat. No. 5,928,868 and include methods for forming hybrid ligands in which at least one ligand is a small molecule. In an illustrative embodiment, the hybrid ligand is introduced into cells that in turn contain a first and a second expression vector. Each expression vector includes DNA for expressing a hybrid protein that encodes a target protein linked to a coding sequence for a transcriptional module. The cells further contains a reporter gene, the expression of which is conditioned on the proximity of the first and second hybrid proteins to each other, an event that occurs only if the hybrid ligand binds to target sites on both hybrid proteins. Those cells that express the reporter gene are selected and the unknown small molecule or the unknown hybrid protein is identified.

A typical embodiment of this invention consists of a method of screening for a molecule that interacts with a PHOR-1 amino acid sequence shown in FIGS. 1A–D (SEQ ID NO: 2), comprising the steps of contacting a population of molecules with the PHOR-1 amino acid sequence, allowing the population of molecules and the PHOR-1 amino acid sequence to interact under conditions that facilitate an interaction, determining the presence of a molecule that interacts with the PHOR-1 amino acid sequence and then separating molecules that do not interact with the PHOR-1 amino acid sequence from molecules that do interact with the PHOR-1 amino acid sequence. In a specific embodiment, the method further includes purifying a molecule that interacts with the PHOR-1 amino acid sequence. In a preferred embodiment, the PHOR-1 amino acid sequence is contacted with a library of peptides.

Therapeutic Methods and Compositions

The identification of PHOR-1 as a prostate cancer protein, opens a number of therapeutic approaches to the treatment of prostate cancers. As discussed above, PHOR-1 is a G protein-coupled receptor (GPCR), and its expression induces colony growth and modulates cAMP and tyrosine phosphorylation. In addition, PHOR-1 presents epitopes at the cell surface that can be targeted for therapy.

The expression profile of PHOR-1 is reminiscent of the MAGEs, PSA and PMSA, which are tissue-specific genes that are up-regulated in melanomas and other cancers (Van den Eynde and Boon, Int J Clin Lab Res. 27:81–86, 1997). Due to their tissue-specific expression and high expression levels in cancer, these molecules are currently being investigated as targets for cancer vaccines (Durrant, Anticancer Drugs 8:727–733, 1997; Reynolds et al., Int J Cancer 72:972–976, 1997). The expression pattern of PHOR-1 provides evidence that it is likewise an ideal target for a cancer vaccine approach to prostate cancer, as its expression is not detected in most normal tissues. Its structural features as a GPCR also provides evidence that PHOR-1 may be a small molecule target, as well as a target for antibody-based therapeutic strategies. The therapeutic strategy can be designed to inhibit the GPCR function of the molecule or to target the PHOR-1 molecule itself.

Accordingly, therapeutic approaches targeting extracellular portions of PHOR-1, or aimed at inhibiting the activity of the PHOR-1 protein, are expected to be useful for patients suffering from prostate cancer and other cancers expressing PHOR-1. The therapeutic approaches aimed at inhibiting the activity of the PHOR-1 protein generally fall into two classes. One class comprises various methods for inhibiting the binding or association of the PHOR-1 protein with its binding partner or with other proteins. Another class comprises a variety of methods for inhibiting the transcription of the PHOR-1 gene or translation of PHOR-1 mRNA.

PHOR-1 as a Cell Surface Target for Antibody-Based Therapy

The cell surface expression of PHOR-1 indicates that this molecule is an attractive target for antibody-based therapeutic strategies. Because PHOR-1 is expressed on cancer cells and not on most normal cells, systemic administration of PHOR-1-immunoreactive compositions would be expected to exhibit excellent sensitivity without toxic, non-specific and/or non-target effects caused by binding of the immunotherapeutic molecule to non-target organs and tissues. Antibodies specifically reactive with extracellular domains of PHOR-1 can be useful to treat PHOR-1-expressing cancers systemically, either as conjugates with a toxin or therapeutic agent, or as naked antibodies capable of inhibiting cell proliferation or function.

PHOR-1 antibodies can be introduced into a patient such that the antibody binds to PHOR-1 on the cancer cells and mediates the destruction of the cells and the tumor and/or inhibits the growth of the cells or the tumor. Mechanisms by which such antibodies exert a therapeutic effect may include complement-mediated cytolysis, antibody-dependent cellular cytotoxicity, modulating the physiological function of PHOR-1, inhibiting ligand binding or signal transduction pathways, modulating tumor cell differentiation, altering tumor angiogenesis factor profiles, and/or by inducing apoptosis. PHOR-1 antibodies can be conjugated to toxic or therapeutic agents and used to deliver the toxic or therapeutic agent directly to PHOR-1-bearing tumor cells. Examples of toxic agents include, but are not limited to, calchemicin, maytansinoids, radioisotopes such as $^{131}$I, ytrium, and bismuth.

Cancer immunotherapy using anti-PHOR-1 antibodies may follow the teachings generated from various approaches that have been successfully employed in the treatment of other types of cancer, including but not limited to colon cancer (Arlen et al., 1998, Crit. Rev. Immunol. 18:133–138), multiple myeloma (Ozaki et al., 1997, Blood 90:3179–3186; Tsunenari et al., 1997, Blood 90:2437–2444), gastric cancer (Kasprzyk et al., 1992, Cancer Res. 52:2771–2776), B-cell lymphoma (Funakoshi et al., 1996, J. Immunother. Emphasis Tumor Immunol. 19:93–101), leukemia (Zhong et al., 1996, Leuk. Res. 20:581–589), colorectal cancer (Moun et al., 1994, Cancer Res. 54:6160–6166); Velders et al., 1995, Cancer Res. 55:4398–4403), and breast cancer (Shepard et al., 1991, J. Clin. Immunol. 11:117–127). Some therapeutic approaches involve conjugation of naked antibody to a toxin, such as the conjugation of $^{131}$I to anti-CD20 antibodies (e.g., Bexxar, Coulter Pharmaceutical), while others involve co-administration of antibodies and other therapeutic agents, such as Herceptin™ (trastuzumab) with paclitaxel (Genentech, Inc.). For treatment of prostate cancer, for example, PHOR-1 antibodies can be administered in conjunction with radiation, chemotherapy or hormone ablation.

Although PHOR-1 antibody therapy may be useful for all stages of cancer, antibody therapy may be particularly appropriate in advanced or metastatic cancers. Treatment with the antibody therapy of the invention may be indicated for patients who have received previously one or more chemotherapy, while combining the antibody therapy of the invention with a chemotherapeutic or radiation regimen may be preferred for patients who have not received chemotherapeutic treatment. Additionally, antibody therapy may enable the use of reduced dosages of concomitant chemotherapy, particularly for patients who do not tolerate the toxicity of the chemotherapeutic agent very well.

It may be desirable for some cancer patients to be evaluated for the presence and level of PHOR-1 expression, preferably using immunohistochemical assessments of tumor tissue, quantitative PHOR-1 imaging, or other techniques capable of reliably indicating the presence and degree of PHOR-1 expression. Immunohistochemical analysis of tumor biopsies or surgical specimens may be preferred for this purpose. Methods for immunohistochemical analysis of tumor tissues are well known in the art.

Anti-PHOR-1 monoclonal antibodies useful in treating prostate and other cancers include those that are capable of initiating a potent immune response against the tumor and those that are capable of direct cytotoxicity. In this regard, anti-PHOR-1 monoclonal antibodies (mAbs) may elicit tumor cell lysis by either complement-mediated or antibody-dependent cell cytotoxicity (ADCC) mechanisms, both of which require an intact Fc portion of the immunoglobulin molecule for interaction with effector cell Fc receptor sites or complement proteins. In addition, anti-PHOR-1 mAbs that exert a direct biological effect on tumor growth are useful in the practice of the invention. Potential mechanisms by which such directly cytotoxic mAbs may act include inhibition of cell growth, modulation of cellular differentiation, modulation of tumor angiogenesis factor profiles, and the induction of apoptosis. The mechanism by which a particular anti-PHOR-1 mAb exerts an anti-tumor effect may be evaluated using any number of in vitro assays designed to determine ADCC, ADMMC, complement-mediated cell lysis, and so forth, as is generally known in the art.

The use of murine or other non-human monoclonal antibodies, or human/mouse chimeric mAbs may induce moderate to strong immune responses in some patients. In some cases, this will result in clearance of the antibody from circulation and reduced efficacy. In the most severe cases, such an immune response may lead to the extensive formation of immune complexes that, potentially, can cause renal failure. Accordingly, preferred monoclonal antibodies used in the practice of the therapeutic methods of the invention are those that are either fully human or humanized and that bind specifically to the target PHOR-1 antigen with high affinity but exhibit low or no antigenicity in the patient.

Therapeutic methods of the invention contemplate the administration of single anti-PHOR-1 mAbs as well as combinations, or cocktails, of different mAbs. Such mAb cocktails may have certain advantages inasmuch as they contain mAbs that target different epitopes, exploit different effector mechanisms or combine directly cytotoxic mAbs with mAbs that rely on immune effector functionality. Such mAbs in combination may exhibit synergistic therapeutic effects. In addition, the administration of anti-PHOR-1 mAbs may be combined with other therapeutic agents, including but not limited to various chemotherapeutic agents, androgen-blockers, and immune modulators (e.g., IL-2, GM-CSF). The anti-PHOR-1 mAbs may be administered in their "naked" or unconjugated form, or may have therapeutic agents conjugated to them.

The anti-PHOR-1 antibody formulations may be administered via any route capable of delivering the antibodies to the tumor site. Potentially effective routes of administration include, but are not limited to, intravenous, intraperitoneal, intramuscular, intratumor, intradermal, and the like. Treatment will generally involve the repeated administration of the anti-PHOR-1 antibody preparation via an acceptable route of administration such as intravenous injection (IV), typically at a dose in the range of about 0.1 to about 10 mg/kg body weight. Doses in the range of 10–500 mg mAb per week may be effective and well tolerated.

Based on clinical experience with the Herceptin mAb in the treatment of metastatic breast cancer, an initial loading dose of approximately 4 mg/kg patient body weight IV followed by weekly doses of about 2 mg/kg IV of the anti-PHOR-1 mAb preparation may represent an acceptable dosing regimen. Preferably, the initial loading dose is administered as a 90 minute or longer infusion. The periodic maintenance dose may be administered as a 30 minute or longer infusion, provided the initial dose was well tolerated. However, as one of skill in the art will understand, various factors will influence the ideal dose regimen in a particular case. Such factors may include, for example, the binding affinity and half life of the Ab or mAbs used, the degree of PHOR-1 expression in the patient, the extent of circulating shed PHOR-1 antigen, the desired steady-state antibody concentration level, frequency of treatment, and the influence of chemotherapeutic agents used in combination with the treatment method of the invention.

Optimally, patients should be evaluated for the level of circulating shed PHOR-1 antigen in serum in order to assist in the determination of the most effective dosing regimen and related factors. Such evaluations may also be used for monitoring purposes throughout therapy, and may be useful to gauge therapeutic success in combination with evaluating other parameters (such as serum PSA levels in prostate cancer therapy).

Inhibition of PHOR-1 Protein Function

The invention includes various methods and compositions for inhibiting the binding of PHOR-1 to its binding partner or ligand, or its association with other protein(s) as well as methods for inhibiting PHOR-1 function. Molecules that target the N-terminus of PHOR-1, such as the antibody described in the examples that follow, are particularly attractive for inhibiting protein function because they are likely to target a ligand-binding site on PHOR-1.

Inhibition of PHOR-1 With Recombinant Proteins

In one approach, recombinant molecules that are capable of binding to PHOR-1 thereby preventing PHOR-1 from accessing/binding to its binding partner(s) or associating with other protein(s) are used to inhibit PHOR-1 function. Such recombinant molecules may, for example, contain the reactive part(s) of a PHOR-1 specific antibody molecule. In a particular embodiment, the PHOR-1 binding domain of a PHOR-1 binding partner may be engineered into a dimeric fusion protein comprising two PHOR-1 ligand binding domains linked to the Fc portion of a human IgG, such as human IgG1. Such IgG portion may contain, for example, the $C_H2$ and $C_H3$ domains and the hinge region, but not the $C_H1$ domain. Such dimeric fusion proteins may be administered in soluble form to patients suffering from a cancer associated with the expression of PHOR-1, including but not limited to prostate, breast, bladder, lung, bone, colon, pancreatic, testicular, cervical and ovarian cancers, where the dimeric fusion protein specifically binds to PHOR-1 thereby blocking PHOR-1 interaction with a binding partner. Such dimeric fusion proteins may be further combined into multimeric proteins using known antibody linking technologies.

Inhibition of PHOR-1 With Intracellular Antibodies

In another approach, recombinant vectors encoding single chain antibodies that specifically bind to PHOR-1 may be introduced into PHOR-1 expressing cells via gene transfer technologies, wherein the encoded single chain anti-PHOR-1 antibody is expressed intracellularly, binds to PHOR-1 protein, and thereby inhibits its function. Methods for engineering such intracellular single chain antibodies are well known. Such intracellular antibodies, also known as "intrabodies",may be specifically targeted to a particular compartment within the cell, providing control over where the inhibitory activity of the treatment will be focused. This technology has been successfully applied in the art (for review, see Richardson and Marasco, 1995, TIBTECH vol. 13). Intrabodies have been shown to virtually eliminate the expression of otherwise abundant cell surface receptors. See, for example, Richardson et al., 1995, Proc. Natl. Acad. Sci. USA 92: 3137–3141; Beerli et al., 1994, J. Biol. Chem. 289: 23931–23936; Deshane et al., 1994, Gene Ther. 1: 332–337.

Single chain antibodies comprise the variable domains of the heavy and light chain joined by a flexible linker polypeptide, and are expressed as a single polypeptide. Optionally, single chain antibodies may be expressed as a single chain variable region fragment joined to the light chain constant region. Well known intracellular trafficking signals may be engineered into recombinant polynucleotide vectors encoding such single chain antibodies in order to precisely target the expressed intrabody to the desired intracellular compartment. For example, intrabodies targeted to the endoplasmic reticulum (ER) may be engineered to incorporate a leader peptide and, optionally, a C-terminal ER retention signal, such as the KDEL amino acid motif. Intrabodies intended to exert activity in the nucleus may be engineered to include a nuclear localization signal. Lipid moieties may be joined to intrabodies in order to tether the intrabody to the cytosolic side of the plasma membrane. Intrabodies may also be targeted to exert function in the cytosol. For example, cytosolic intrabodies may be used to sequester factors within the cytosol, thereby preventing them from being transported to their natural cellular destination.

In one embodiment, PHOR-1 intrabodies are designed to bind specifically to a particular PHOR-1 domain. For example, cytosolic intrabodies that specifically bind to the PHOR-1 protein may be used to prevent PHOR-1 related molecules from gaining access to the nucleus, thereby preventing it from exerting any biological activity within the nucleus.

In order to direct the expression of such intrabodies specifically to particular tumor cells, the transcription of the intrabody may be placed under the regulatory control of an appropriate tumor-specific promoter and/or enhancer. In order to target intrabody expression specifically to prostate, for example, the PSA promoter and/or promoter/enhancer may be utilized (See, for example, U.S. Pat. No. 5,919,652).

Inhibition of PHOR-1 Transcription or Translation

Within another class of therapeutic approaches, the invention provides various methods and compositions for inhibiting the transcription of the PHOR-1 gene. Similarly, the invention also provides methods and compositions for inhibiting the translation of PHOR-1 mRNA into protein.

In one approach, a method of inhibiting the transcription of the PHOR-1 gene comprises contacting the PHOR-1 gene with a PHOR-1 antisense polynucleotide. In another approach, a method of inhibiting PHOR-1 mRNA translation comprises contacting the PHOR-1 mRNA with an antisense polynucleotide. In another approach, a PHOR-1 specific ribozyme may be used to cleave the PHOR-1 message, thereby inhibiting translation. Such antisense and ribozyme based methods may also be directed to the regulatory regions of the PHOR-1 gene, such as the PHOR-1 promoter and/or enhancer elements. Similarly, proteins capable of inhibiting a PHOR-1 gene transcription factor may be used to inhibit PHOR-1 mRNA transcription. The various polynucleotides and compositions useful in the aforementioned methods have been described above. The use of antisense and ribozyme molecules to inhibit transcription and translation is well known in the art.

Other factors that inhibit the transcription of PHOR-1 through interfering with PHOR-1 transcriptional activation may also be useful for the treatment of cancers expressing PHOR-1. Similarly, factors that are capable of interfering with PHOR-1 processing may be useful for the treatment of cancers expressing PHOR-1. Cancer treatment methods utilizing such factors are also within the scope of the invention.

General Considerations for Therapeutic Strategies

Gene transfer and gene therapy technologies may be used for delivering therapeutic polynucleotide molecules to tumor cells synthesizing PHOR-1 (i.e., antisense, ribozyme, polynucleotides encoding intrabodies and other PHOR-1 inhibitory molecules). A number of gene therapy approaches are known in the art. Recombinant vectors encoding PHOR-1 antisense polynucleotides, ribozymes, factors capable of interfering with PHOR-1 transcription, and so forth, may be delivered to target tumor cells using such gene therapy approaches.

The above therapeutic approaches may be combined with any one of a wide variety of chemotherapy or radiation therapy regimens. These therapeutic approaches may also enable the use of reduced dosages of chemotherapy and/or less frequent administration, particularly in patients that do not tolerate the toxicity of the chemotherapeutic agent well.

The anti-tumor activity of a particular composition (e.g., antisense, ribozyme, intrabody), or a combination of such compositions, may be evaluated using various in vitro and in vivo assay systems. In vitro assays for evaluating therapeutic potential include cell growth assays, soft agar assays and other assays indicative of tumor promoting activity, binding assays capable of determining the extent to which a therapeutic composition will inhibit the binding of PHOR-1 to a binding partner, etc.

In vivo, the effect of a PHOR-1 therapeutic composition may be evaluated in a suitable animal model. For example, xenogeneic prostate cancer models wherein human prostate cancer explants or passaged xenograft tissues are introduced into immune compromised animals, such as nude or SCID mice, are appropriate in relation to prostate cancer and have been described (Klein et al., 1997, Nature Medicine 3: 402–408). For example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastases characteristic of late stage disease. Efficacy may be predicted using assays that measure inhibition of tumor formation, tumor regression or metastasis, and the like. See, also, the Examples below.

In vivo assays that qualify the promotion of apoptosis may also be useful in evaluating potential therapeutic compositions. In one embodiment, xenografts from bearing mice treated with the therapeutic composition may be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods may be formulated into pharmaceutical compositions comprising a carrier suitable for the desired delivery method. Suitable carriers include any material that when combined with the therapeutic composition retains the anti-tumor function of the therapeutic composition and is non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences $16^{th}$ Edition, A. Osal., Ed., 1980).

Therapeutic formulations may be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations may be lyophilized and stored as sterile powders, preferably under vacuum, and then reconstituted in bacteriostatic water containing, for example, benzyl alcohol preservative, or in sterile water prior to injection.

Dosages and administration protocols for the treatment of cancers using the foregoing methods will vary with the method and the target cancer and will generally depend on a number of other factors appreciated in the art.

Cancer Vaccines

The invention further provides cancer vaccines comprising a PHOR-1 protein or fragment thereof, as well as DNA based vaccines. In view of the prostate- and tumor-restricted expression of PHOR-1, PHOR-1 cancer vaccines are expected to be effective at specifically preventing and/or treating PHOR-1 expressing cancers without creating non-specific effects on non-target tissues. The use of a tumor antigen in a vaccine for generating humoral and cell-mediated immunity for use in anti-cancer therapy is well known in the art and has been employed in prostate cancer using human PSMA and rodent PAP immunogens (Hodge et al., 1995, Int. J. Cancer 63: 231–237; Fong et al., 1997, J. Immunol. 159: 3113–3117). Such methods can be readily practiced by employing a PHOR-1 protein, or fragment thereof, or a PHOR-1-encoding nucleic acid molecule and recombinant vectors capable of expressing and appropriately presenting the PHOR-1 immunogen.

For example, viral gene delivery systems may be used to deliver a PHOR-1-encoding nucleic acid molecule. Various viral gene delivery systems that can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8: 658–663). Non-viral delivery systems may also be employed by using naked DNA encoding a PHOR-1 protein or fragment thereof introduced into the patient (e.g., intramuscularly) to induce an anti-tumor response. In one embodiment, the full-length human PHOR-1 cDNA may be employed.

In one embodiment, a PHOR-1 cancer vaccine is based on the identification of immunogenic peptides within the PHOR-1 amino acid sequence shown in FIGS. 1A–D (SEQ ID NO: 2). As discussed further in the examples below, specific portions of PHOR-1 have been shown to induce T and B cell responses. A GST fusion protein encompassing amino acids 86–310 of PHOR-1 (FIGS. 1A–D; SEQ ID NO: 2) has been used to generate an immune response in mice for the production of monoclonal antibodies. This same GST-PHOR-1 fusion protein, as well as two peptides corresponding to amino acids 1–14 (MVDPNGNESSATYF; SEQ ID NO: 8) and 262–274 (VHRFSKRRDSPLP; SEQ ID NO: 9) of PHOR-1, have been used to generate an immune response in rabbits for the production of polyclonal antibodies. Thus, these specific portions of PHOR-1, and polynucleotides encoding these portions, may be selected for the production of a cancer vaccine.

In another embodiment, PHOR-1 nucleic acid molecules encoding specific cytotoxic T lymphocyte (CTL) epitopes may be employed. CTL epitopes can be determined using specific algorithms (e.g., Epimer, Brown University) to identify peptides within a PHOR-1 protein that are capable of optimally binding to specified HLA alleles. One suitable algorithm is the HLA Peptide Motif Search algorithm available at the Bioinformatics and Molecular Analysis Section (BIMAS) web site (http://bimas.dcrt.nih.gov/). This algorithm is based on binding of specific peptide sequences in the groove of HLA Class I molecules and specifically HLA-A2 (Falk et al., 1991, Nature 351:290–6; Hunt et al., 1992, Science 255:1261–3; Parker et al., 1992, J. Immunol. 149:3580–7; Parker et al., 1994, J. Immunol. 152:163–75). The HLA Peptide Motif Search algorithm allows location and ranking of 8-mer, 9-mer, and 10-mer peptides from a complete protein sequence for predicted binding to HLA-A2 as well as other Class I molecules. Most HLA-A2 binding peptides are 9-mers, favorably containing a leucine at position 2 and a valine or leucine at position 9 (Parker et al., 1992, J. Immunol. 149:3580–7). Actual binding of peptides to HLA-A2 can be evaluated by stabilization of HLA-A2 expression on the antigen processing defective cell line T2 (Xue et al., 1997, Prostate 30:73–8; Peshwa et al., 1998, Prostate 36:129–38). Immunogenicity of specific peptides can be evaluated in vitro by stimulation of CD8+ CTL in the presence of dendritic cells (Xue et al.; Peshwa et al., supra).

Various ex vivo strategies may also be employed. One approach involves the use of dendritic cells to present PHOR-1 antigen to a patient's immune system. Dendritic cells express MHC class I and II, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28: 65–69; Murphy et al., 1996, Prostate 29: 371–380). Dendritic cells can be used to present PHOR-1 peptides to T cells in the context of MHC class I and II molecules. In one embodiment, autologous dendritic cells are pulsed with PHOR-1 peptides capable of binding to MHC molecules. In another embodiment, dendritic cells are pulsed with the complete PHOR-1 protein. Yet another embodiment involves engineering the overexpression of the PHOR-1 gene in dendritic cells using various implementing vectors known in the art, such as adenovirus (Arthur et al., 1997, Cancer Gene Ther. 4: 17–25), retrovirus (Henderson et al., 1996, Cancer Res. 56: 3763–3770), lentivirus, adeno-associated virus, DNA transfection (Ribas et al., 1997, Cancer Res. 57: 2865–2869), and tumor-derived RNA transfection (Ashley et al., 1997, J. Exp. Med. 186: 1177–1182). Cells expressing PHOR-1 may also be engineered to express immune modulators, such as GM-CSF, and used as immunizing agents.

Anti-idiotypic anti-PHOR-1 antibodies can also be used in anti-cancer therapy as a vaccine for inducing an immune response to cells expressing a PHOR-1 protein. Specifically, the generation of anti-idiotypic antibodies is well known in the art and can readily be adapted to generate anti-idiotypic anti-PHOR-1 antibodies that mimic an epitope on a PHOR-1 protein (see, for example, Wagner et al., 1997, Hybridoma 16: 33–40; Foon et. al., 1995, J Clin Invest 96: 334–342; Herlyn et al., 1996, Cancer Immunol Immunother 43: 65–76). Such an anti-idiotypic antibody can be used in cancer vaccine strategies.

Genetic immunization methods may be employed to generate prophylactic or therapeutic humoral and cellular immune responses directed against cancer cells expressing PHOR-1. Constructs comprising DNA encoding a PHOR-1 protein/immunogen and appropriate regulatory sequences may be injected directly into muscle or skin of an individual, such that the cells of the muscle or skin take up the construct and express the encoded PHOR-1 protein/immunogen. Expression of the PHOR-1 protein immunogen results in the generation of prophylactic or therapeutic humoral and cellular immunity against prostate and other PHOR-1-expressing cancers. Various prophylactic and therapeutic genetic immunization techniques known in the art may be used (for review, see information and references published at Internet address www.genweb.com).

Kits

For use in the diagnostic and therapeutic applications described or suggested above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for a PHOR-1 protein or a PHOR-1 gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the on the container to indicate that the composition is used for a specific therapy or non-therapeutic application, and may also indicate directions for either in vivo or in vitro use, such as those described above.

The PHOR-1 cDNA was deposited under the terms of the Budapest Treaty on Jul. 2,1999, with the American Type Culture Collection (ATCC; 10801 University Blvd., Manassas, Va. 20110-2209 USA) as plasmid p101P3A11, and has been assigned Accession No. PTA-312.

EXAMPLES

Various aspects of the invention are further described and illustrated by way of the several examples that follow, none of which are intended to limit the scope of the invention.

Example 1

SSH-Genera ted Isolation of cDNA Fragment of the PHOR-1 Gene

Materials and Methods

LAPC Xenografts

LAPC xenografts were obtained from Dr. Charles Sawyers (UCLA) and generated as described (Klein et al, 1997, Nature Med. 3: 402–408; Craft et al., 1999, Cancer Res. 59: 5030–5036). Androgen dependent and independent LAPC-4 xenografts (LAPC-4 AD and AI, respectively) and LAPC-9 xenografts (LAPC-9 AD and AI, respectively) were grown in intact male SCID mice or in castrated males, respectively, and were passaged as small tissue chunks in recipient males. LAPC-4 AI xenografts were derived from LAPC-4 AD tumors and LAPC-9 AI xenografts were derived from LAPC-9 AD tumors. To generate the AI xenografts, male mice bearing LAPC AD tumors were castrated and maintained for 2–3 months. After the LAPC tumors re-grew, the tumors were harvested and passaged in castrated males or in female SCID mice.

Cell Lines

Human cell lines (e.g., HeLa) were obtained from the ATCC and were maintained in DMEM with 10% fetal calf serum.

RNA Isolation

Tumor tissue and cell lines were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides

The following HPLC purified oligonucleotides were used.
DPNCDN (cDNA synthesis primer) (SEQ ID NO: 21):

5'TTTTGATCAAGCTT$_{30}$3'

Adaptor 1 (SEQ ID NO: 22 and 23, respectively):

5'CTAATACGACTCACTATAGGGCTC-
GAGCGGCCGCCCGGGCAG3'

3'GGCCCGTCCTAG5'

Adaptor 2 (SEQ ID NO: 24 and 25, respectively):

5'GTAATACGACTCACTATAGGGCAGCGTG-
GTCGCGGCCGAG3'

3' CGGCTCCTAG5'

PCR primer 1 (SEQ ID NO: 26):

5'CTAATACGACTCACTATAGGGC3'

Nested primer (NP)1 (SEQ ID NO: 27):

5'TCGAGCGGCCGCCCGGGCAGGA3'

Nested primer (NP)2 (SEQ ID NO: 28):

5'AGCGTGGTCGCGGCCGAGGA3'

Suppression Subtractive Hybridization

Suppression subtractive hybridization (SSH) was used to identify cDNAs corresponding to genes that may be up-regulated in androgen dependent prostate cancer compared to androgen independent cancer.

Double stranded cDNAs corresponding to the LAPC-4 AD xenograft 14 days post castration (tester) and the LAPC-4 AD xenograft (driver) were synthesized from 2 µg of poly(A)$^+$ RNA isolated from xenograft tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs. at 37° C. Digested cDNA was extracted with phenol/chloroform (1:1) and ethanol precipitated.

Driver cDNA (LAPC-4 AD) was generated by combining in a 1:1 ratio Dpn II digested LAPC-4 AD cDNA with a mix of digested cDNAs derived from human benign prostatic hyperplasia (BPH), the human cell lines HeLa, 293, A431, Colo205, and mouse liver.

Tester cDNA (LAPC-4 AD, 14 days post castration) was generated by diluting 1 µl of Dpn II digested LAPC-4 AD 14 day post castration cDNA (400 ng) in 5 µl of water. The diluted cDNA (2 µl, 160 ng) was then ligated to 2 µl of Adaptor 1 and Adaptor 2 (10 µM), in separate ligation reactions, in a total volume of 10 µl at 16° C. overnight, using 400 u of T4 DNA ligase (CLONTECH). Ligation was terminated with 1 µl of 0.2 M EDTA and heating at 72° C. for 5 min.

The first hybridization was performed by adding 1.5 µl (600 ng) of driver cDNA to each of two tubes containing 1.5 µl (20 ng) Adaptor 1- and Adaptor 2- ligated tester cDNA. In a final volume of 4 µl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 µl of fresh denatured driver cDNA and were allowed to hybridize overnight at 68° C. The second hybridization was then diluted in 200 µl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH

To amplify gene fragments resulting from SSH reactions, two PCR amplifications were performed. In the primary PCR reaction 1 µl of the diluted final hybridization mix was added to 1 µl of PCR primer 1 (10 µM), 0.5 µl dNTP mix (10 µM), 2.5 µl 10×reaction buffer (CLONTECH) and 0.5 µl 50×Advantage cDNA polymerase Mix (CLONTECH) in a final volume of 25 µl. PCR 1 was conducted using the following conditions: 75° C. for 5 min., 94° C. for 25 sec., then 27 cycles of 94° C. for 10 sec 30 sec, 72° C. for 1.5 min. Five separate primary PCR reactions were performed for each experiment. The products were pooled and diluted 1:10 with water. For the secondary PCR reaction, 1 µl from the pooled and diluted primary PCR reaction was added to the same reaction mix as used for PCR 1, except that primers NP1 and NP2 (10 µM) were used instead of PCR primer 1. PCR 2 was performed using 10–12 cycles of 94° C. for 10 sec, 68° C. for 30 sec, 72° C. for 1.5 minutes. The PCR products were analyzed using 2% agarose gel electrophoresis.

The PCR products were inserted into pCR2.1 using the T/A vector cloning kit (Invitrogen). Transformed *E. coli* were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis

First strand cDNAs were generated from 1 µg of mRNA with oligo (dT)12–18 priming using the Gibco-BRL Superscript Preamplification system. The manufacturers protocol was used and included an incubation for 50 min at 42° C. with reverse transcriptase followed by RNase H treatment at 37° C. for 20 min. After completing the reaction, the volume was increased to 200 µl with water prior to normalization. First strand cDNAs from 16 different normal human tissues were obtained from Clontech.

Normalization of the first strand cDNAs from multiple tissues was performed by using the primers 5'atatcgc-cgcgctcgtcgtcgacaa3' (SEQ ID NO: 29) and 5'agccacacg-cagct cattgtagaagg 3' (SEQ ID NO: 30) to amplify β-actin. First strand cDNA (5 µl) was amplified in a total volume of 50 µl containing 0.4 µM primers, 0.2 µM each dNTPs, 1XPCR buffer (Clontech, 10 mM Tris-HCL, 1.5 mM MgCl$_2$, 50 mM KCl, pH8.3) and 1X Klentaq DNA polymerase (Clontech). Five µl of the PCR reaction was removed at 18, 20, and 22 cycles and used for aOarose gel electrophoresis. PCR was performed using an MJ Research thermal cycler under the following conditions: initial denaturation was at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization were required to achieve equal band intensities in all tissues after 22 cycles of PCR.

To determine expression levels of the PHOR-1 gene, 5 µl of normalized first strand cDNA was analyzed by PCR using 25, 30, and 35 cycles of amplification using the following primer pairs, which were designed with the assistance of (MIT; for details, see, www.genome.wi.mit.edu) (SEQ ID NO: 31 and 32, respectively):

101P3A11.1 ATCCTGACTAGGTTGTGGTTGGAG

101P3A11.2 TGTGGTTGGGAGTTCTAAAGAGGA

Semi quantitative expression analysis was achieved by comparing the PCR products at cycle numbers that give light band intensities.

Results

Several SSH experiments were conduced as described in the Materials and Methods, supra, and led to the isolation of numerous candidate gene fragment clones. All candidate clones were sequenced and subjected to homology analysis against all sequences in the major public gene and EST databases in order to provide information on the identity of the corresponding gene and to help guide the derision to analyze a particular gene for differential expression. In general, gene fragments which had no homology to any known sequence in any of the searched databases, and thus considered to represent novel genes, as well as gene fragments showing homology to previously sequenced expressed sequence tags (FSTs), were subjected to differential expression analysis by RT-PCR and/or northern analysis.

One of the SSH clones, comprising about 427 bp, showed no homology to any known gene, and was designated 101P3A11. This clone represents a fragment of the full length cDNA encoding PHOR-1 as shown in FIG. 1A (see also Example 2). The sequence of the 101P3A11 SSH fragment is shown in FIG. 3.

Initial RT-PCR analysis (FIGS. 5A–B) showed expression of 101P3A11 only in prostate, LAPC-4 AD, LAPC-4 AD 3 day and LAPC-4 AD 14 day post-castration, but Example 2

Isolation of Full Length PHOR-1 Encoding cDNA

A full length cDNA (GTH10) of 3136 bp was isolated from a prostate library, revealing an ORF of 317 amino acids (FIGS. 1A–D). The protein sequence reveals 7 transmembrane domains and has homology to G protein-coupled receptors (GPCRs) involved in olfaction (Raming et al., 1993, Nature 361: 353; Malnic et al., 1999, Cell 96:713). The most homologous sequence to 101P3A11 is a rat olfactory receptor expressed in brain known as RA1c (Raming et al., 1998, Receptor Channels 6: 141). It is 59.9% identical to RA1c in 299 residue overlap. The human homologue of RA1c is likely to be HPRAJ70, a prostate-specific GPCR identified by Human Genome Sciences (U.S. Pat. No. 5,756,309, WO 96/39435). Alignments to both genes with 101P3A11 is shown in FIG. 2. The full length 101P3A11 cDNA encodes an amino acid sequence that is 59.4% identical to HPRAJ70 in a 298 residue overlap. The homology of 101P3A11 with brain olfactory receptors led us to name the gene Prostate Homologue of Olfactory Receptor-1 (PHOR-1). Proteins that are members of this receptor family exhibit an extracellular amino-terminus, three additional extracellular loops, three intracellular loops and an intracellular carboxyl terminus. The second extracellular region of PHOR-1 exhibits one potential N-glycosylation site at residue 90 (NST) suggesting that the protein may be glycosylated.

The full length PHOR-1 cDNA (p101P3A11, clone GTH10) was deposited with the American Type Culture Collection on Jul. 2, 1999, and assigned accession number PTA-312.

Example 3
PHOR-1 Gene Expression Analysis

PHOR-1 mRNA expression in normal human tissues was first analyzed by northern blotting of two multiple tissue blots (Clontech; Palo Alto, Calif.), comprising a total of 16 different normal human tissues, using labeled 101P3A11 SSH fragment (Example 1) as a probe. RNA samples were quantitatively normalized with a β-actin probe. The results of this analysis are shown in FIGS. 6A–C. Expression of a 3.5 kb transcript was only detected in normal prostate.

PHOR-1 expression in normal tissues was further analyzed using a multi-tissue RNA dot blot containing 76 different samples (representing mainly normal tissues as well as a few cancer cell lines) demonstrated strong expression of PHOR-1 only in prostate (FIG. 7). Significantly lower expression is detected in heart tissues.

In addition, RT-PCR can be used to analyze expression of PHOR-1 in various tissues, including patient-derived cancers. First strand cDNAs are generated from 1 μg of mRNA with oligo (dT) 12–18 priming using the Gibco-BRL Superscript Preamplification system. The manufacturers protocol can be used and includes an incubation for 50 min at 42° C. with reverse transcriptase followed by RNase H treatment at 37° C. for 20 min. After completing the reaction, the volume is increased to 200 μl with water prior to normalization. First strand cDNAs are prepared from various tissues of interest. Normalization can be performed by PCR using primers to actin and GAPDH. Semi-quantitative PCR is performed using primers to PHOR-1.

Figure 10:
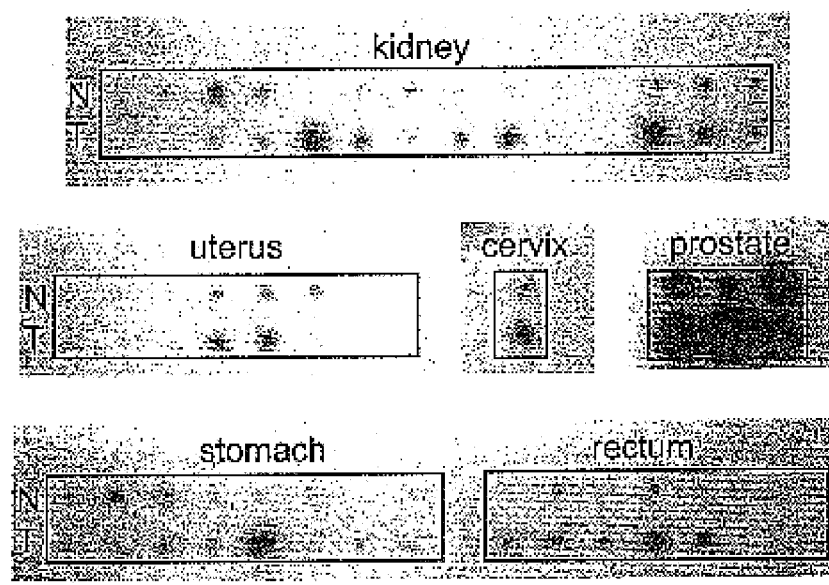
FIG. 10. Expression of PHOR-1 in human cancers demonstrated by dot blot analysis of tumor RNA (T) and normal RNA (N) matched samples using patient-derived amplified cDNAs. Up-regulation of PHOR-1 expression was found in 3 of 3 prostate cancer patients, 6 of 14 kidney cancer patients, 2 of 8 uterine cancer patients, 3 of 8 stomach cancer patients and 7 of 7 rectal cancer patients.

Example 4
PHOR-1 Expression in Prostate Cancer Xenografts and Patient Samples
Northern Analysis of Prostate Cancer Xenografts and Clinical Specimens To analyze PHOR-1 expression in prostate cancer tissues, northern blotting was performed on RNA derived from the LAPC xenografts and a panel of prostate cancer samples with their matched normal adjacent prostate tissue. The results show high levels of PHOR-1 expression in LAPC-4 AD, LAPC-9 AD, and LAPC-9 AI. Lower expression is detected in normal prostate and no expression is seen in LAPC-4 AI (FIG. 8). Analysis of 4 normal/tumor matched pairs of clinical specimens derived from prostate cancer patients showed expression of PHOR-1 in all patient samples (FIG. 8). Interestingly, in 3 out of 4 matched pairs, PHOR-1 expression was 5–20 fold higher in the tumor samples compared to the matched normal adjacent tissue. These results suggest that the prostate-specific PHOR-1 is up-regulated in cancer and may have a functional role in prostate cancer pathology.
Northern and Dot Blot Analysis of Matched Tumor/Normal Patient Samples Northern and dot blot analysis showed up-regulation of PHOR-1 in 8 out of 10 prostate cancer tumors (Gleason scores 6 to 9) when compared to their normal adjacent tissues (FIGS. 9A–B). Dot blots using patient-derived amplified cDNAs (Clontech, CA) show upregulation of PHOR-1 in 3/3 prostate cancer patients, 6/14 kidney cancer patients, 2/8 uterine cancer, 1/1 cervical cancer, 3/8 stomach cancer, and in 7/7 rectal cancer patients (FIG. 10).
RNA in situ RNA in situ analysis using anti-sense PHOR-1 riboprobe showed significant glandular epithelial and basal cell expression in normal prostate (4/4), PIN (1/1), and prostate cancer (6/6) patients. PHOR-1 sense riboprobe had little to no staining. The RNA in situ staining in PIN and prostate cancer is shown in FIGS. 11A–B. The staining intensity in the cancer cells was generally higher than that observed in normal glands (FIGS. 12A–B). The RNA in situ results also demonstrate that the expression observed in the prostate tissues is in the glandular epithelia, basal cells, and cancer cells.

Example 5
Expression of Recombinant PHOR-1 Protein in Bacterial Cells
pGEX Constructs To express PHOR-1 in bacterial cells, portions of PHOR-1 were fused to the glutathione S-transferase (GST) gene by cloning into pGEX-2T or pGEX-6P-1 (Amersham Pharmacia Biotech, NJ). All constructs were made to generate recombinant PHOR-1 protein sequences with GST fused at the N-terminus with or without a six histidine epitope at the C-terminus. The six histidine epitope tag was generated by adding the histidine codons to the cloning primer at the 3' end of the ORF. A Thrombin or PreScission™ recognition site permits cleavage of the GST tag from PHOR-1 or pGEX-2T and pGEX-6P-1 constructs, respectively. The ampicillin resistance gene and pBR322 origin permits selection and maintenance of the plasmid in E. coli. The following fragments of PHOR-1 were cloned into pGEX-6P-1:

Amino acids 128 to 238
Amino acids 188 to 317
Amino acids 100 to 295

The following fragment of PHOR-1 was cloned into pGEX-2T: Amino acids 86 to 310.

Additional constructs can be made in pGEX-6P-1 spanning the following regions of the PHOR-1 protein:

Amino acids 1 to 128
Amino acids 1 to 188
Amino acids 1 to 317
Amino acids 52 to 238.

pMAL Constructs

To express PHOR-1 in bacterial cells, portions of PHOR-1 were fused to the maltose-binding protein (MBP) gene by cloning into pMAL-c2X and pMAL-p2X (New England Biolabs, MA). All constructs were made to generate recombinant PHOR-1 protein sequences with MBP fused at the N-terminus and a six histidine epitope at the C-terminus. The six histidine epitope tag was generated by adding the histidine codons to the 3' cloning primer. A Factor Xa recognition site permits cleavage of the GST tag from PHOR-1. The pMAL-c2X and pMAL-p2X vectors are optimized to express the recombinant protein in the cytoplasm or periplasm respectively. Periplasm expression enhances folding of proteins with disulfide bonds. The PHOR-1 amino acids 86 to 310 were cloned into both pMAL-c2X and pMAL-p2X.

Additional constructs can be made in pMAL-c2X and pMAL-p2X spanning the following regions of the PHOR-1 protein:

Amino acids 1 to 128
Amino acids 1 to 188
Amino acids 1 to 317
Amino acids 52 to 238
Amino acids 100 to 295
Amino acids 128 to 238
Amino acids 188 to 317.

Example 6
Expression of Recombinant PHOR-1 Protein in Mammalian Systems
pcDNA4/HisMax-TOPO Construct To express PHOR-1 in mammalian cells, the 951 bp PHOR-1 ORF was cloned into pcDNA4/HisMax-TOPO Version A (cat# K864–20, Invitrogen, Carlsbad, Calif.). Protein expression is driven from the cytomegalovirus (CMV) promoter and the SP163 translational enhancer. The recombinant protein has Xpress™ and six histidine epitopes fused to the N-terminus. The C-terminus of the recombinant protein has a 28 amino acid fusion resulting from vector sequences prior to the termination codon. The pcDNA4/HisMax-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in E. coli.

pcDNA3.1/MycHis Construct

To express PHOR-1 in mammalian cells, the 951 bp PHOR-1 ORF was cloned into pcDNA3.1 /MycHis Version A (Invitrogen, Carlsbad, Calif.). Protein expression is driven from the cytomegalovirus (CMV) promoter. The recombinant protein has the myc and six histidines fused to the C-terminus. The pcDNA3.1/MycHis vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells expressing the protein and the ampicillin resistance gene and ColE1 origin permits selection and maintenance of the plasmid in E. coli.

pcDNA3.1CT-GFP-TOPO Construct

To express PHOR-1 in mammalian cells and to allow detection of the recombinant protein using fluorescence, the 951 bp ORF was cloned into pcDNA3.1CT-GFP-TOPO (Invitrogen, Calif.). Protein expression is driven from the cytomegalovirus (CMV) promoter. The recombinant protein has the green fluorescent protein (GFP) fused to the C-terminus facilitating non-invasive, in vivo detection and cell biology studies. The pcDNA3.1/MycHis vector also contains the bovine growth hormone (BGH) polyadenylation signal and transcription termination sequence to enhance mRNA stability along with the SV40 origin for episomal replication and simple vector rescue in cell lines expressing the large T antigen. The neomycin resistance gene allows for selection of mammalian cells expressing the protein and the ampicillin resistance gene and ColE1 origin permits selection and maintenance of the plasmid in E. coli.

An additional construct with a N-terminal GFP fusion can be made in pcDNA3.1NT-GFP-TOPO spanning the entire length of the PHOR-1 protein.

pSRa Constructs

To generate mammalian cell lines expressing PHOR-1 constitutively, the 951 bp ORF was cloned into pSRa constructs and stable cell lines were generated. Amphotropic and ecotropic retroviruses are generated by transfection of pSRa constructs into the 293T-10A1 packaging line or co-transfection of pSRa and a helper plasmid (φ-) in 293 cells, respectively. The retrovirus can be used to infect a variety of mammalian cell lines, resulting in the integration of the cloned gene, PHOR-1, into the host cell-lines. Protein expression is driven from a long terminal repeat (LTR). The Neomycin resistance gene allows for selection of mammalian cells expressing the protein and the ampicillin resistance gene and ColE1 origin permits selection and maintenance of the plasmid in E. coli. An additional pSRa construct was made that fused the FLAG tag to the C-terminus to allow detection using anti-FLAG antibodies. The FLAG sequence 5' gat tac aag gat gac gac gat aag 3' (SEQ ID NO: 33) were added to cloning primer at the 3' end of the ORF.

Additional pSRa constructs can be made to produce both N-terminal and C-terminal GFP and myc/6 HIS fusion proteins of the full length PHOR-1 protein.

Example 7
Production of Recombinant PHOR-1 in a Baculovirus System

To generate a recombinant PHOR-1 protein in a baculovirus expression system, the PHOR-1 cDNA is cloned into the baculovirus transfer vector pBlueBac 4.5 (Invitrogen), which provides a His-tag at the N-terminus Specifically, pBlueBac--PHOR-1 is co-transfected with helper plasmid pBac-N-Blue (Invitrogen) into SF9 (Spodoptera frugiperda) insect cells to generate recombinant baculovirus (see Invitrogen instruction manual for details). Baculovirus is then collected from cell supernatant and purified by plaque assay.

Recombinant PHOR-1 protein is then generated by infection of HighFive insect cells (Invitrogen) with the purified baculovirus. Recombinant PHOR-1 protein may be detected using anti-PHOR-1 antibody. PHOR-1 protein may be purified and used in various cell based assays or as immunogen to generate polyclonal and monoclonal antibodies specific for PHOR-1.

Example 8
Polyclonal and Monoclonal Antibodies to PHOR-1

Three immunogens were derived in order to generate antibody reagents that specifically bind to PHOR1. Two antigens were peptides encoding amino acids 1–14 (MVDPNGNESSATYF; SEQ ID NO: 8) and amino acids 262–274 (VHRFSKRRDSPLP; SEQ ID NO: 9) of the PHOR-1 protein sequence. These peptides are predicted to encode the extracellular N-terminus and the extracellular loop between the putative $6^{th}$ and $7^{th}$ transmembrane domains, respectively, of the PHOR1 protein, which is the expected ligand binding site. The third immunogen was a glutathione-S-transferase (GST) fusion protein encompassing amino acids 86–310 of the PHOR-1 protein sequence. This fusion protein was generated by PCR-mediated amplification of nucleotides 388–1062 of the cDNA clone of PHOR-1 with the following primers (SEQ ID NO: 34,35, respectively):

5' PRIMER CCGAATTCCATTCCATCTTCTGGTTCAATTTC EcoRI

3' PRIMER CCTCTCGAGTTCACATGGAAAAGTCGAAG XhoI

The resultant product was cloned into the EcoRI and XhoI restriction sites of the pGEX-2T GST-fusion vector (Pharmacia). Recombinant GST-PHOR-1 fusion protein was purified from induced bacteria by glutathione-sepharose affinity chromatography.

In addition to the above antigens, other peptides and bacterial and baculovirus virus produced proteins encoding other regions of the PHOR-1 protein sequence may be used to generate PHOR-1 specific antibody reagents. Such reagents may be directed to regions of the PHOR-1 protein that may modulate PHOR-1 function, such as an antibody that blocks ligand binding. Such reagents can be used to elucidate the function and signal transduction pathways of the PHOR-1 protein.

Generation of Polyclonal Antibodies

To generate polyclonal sera to PHOR-1, the purified GST-fusion protein and the peptides coupled to Keyhole limpet hemacyanin (KLH) were used to immunize individual rabbits as follows. The rabbits were immunized with 200 μg of fusion protein or KLH-peptide antigen mixed in complete Freund's adjuvant. The rabbits were then injected every two weeks with 200 μg of immunogen in incomplete Freund's adjuvant. Test bleeds were taken approximately 7–10 days following each immunization. The titer of each peptide antisera was at least $1 \times 10^5$ as determined by ELISA to the respective immunogens. The titer of the GST-fusion serum was at least $1 \times 10^6$.

Figure 13A:
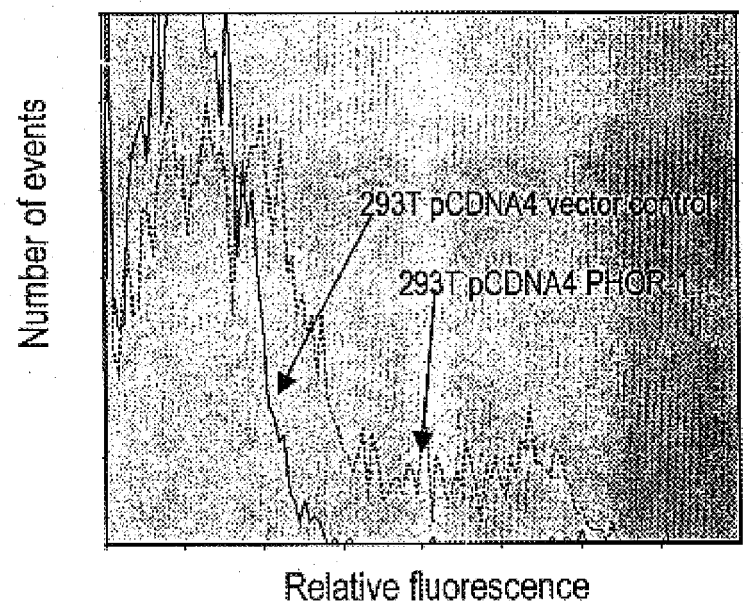
FIG. 13A. Expression and detection of PHOR-1 protein in PHOR-1-293T cells. 293T cells were transiently transfected with 10 μg of either pCDNA4 HIS MAX PHOR-1 plasmid, which contains an Express epitope and HIS tag fused to the N-terminus of the PHOR-1 sequence, or vector control and assayed for PHOR-1 protein expression by flow cytometry. For flow cytometric detection of PHOR-1 protein, PHOR-1 and vector control transfected 293T cells were harvested 2 days following transfection and stained with 10 μg/ml of anti-Express tmAb (Invitrogen) followed by anti-mouse FITC conjugate and then analyzed on a Coulter EPICS XL flow cytometer. Indicated with arrows are the respective fluorescent profiles of control (solid line) and PHOR-1 transfected (dotted line) cell populations. These results demonstrate cell surface expression and recognition of PHOR-1 protein in transfected cells.

Peptide antisera was affinity purified by passage of the serum over an affinity column composed of the respective peptide covalently coupled to Affigel matrix (BioRad). Serum raised to the GST-fusion is semi-purified first by removal of GST-reactive antibody by passage over a GST affinity column. PHOR-1 specific antibody is then isolated by passage over a GST-PHOR-1 affinity column. Alternatively, PHOR-1 specific antisera may be isolated by affinity chromatography using a maltose binding protein (MBP)-PHOR-1 fusion protein encoding the same amino acids. Affinity purified serum from rabbits immunized with the N-terminal peptide of the PHOR-1 sequence immunoprecipitates PHOR-1 protein from PHOR-1 cDNA transfected cell lysates (FIGS. 13A–B) and detects cell surface expression of PHOR-1 protein by flow cytometric analysis of transfected cells (FIGS. 14A–B).

Generation of Murine Monoclonal Antibodies

Figure 15:
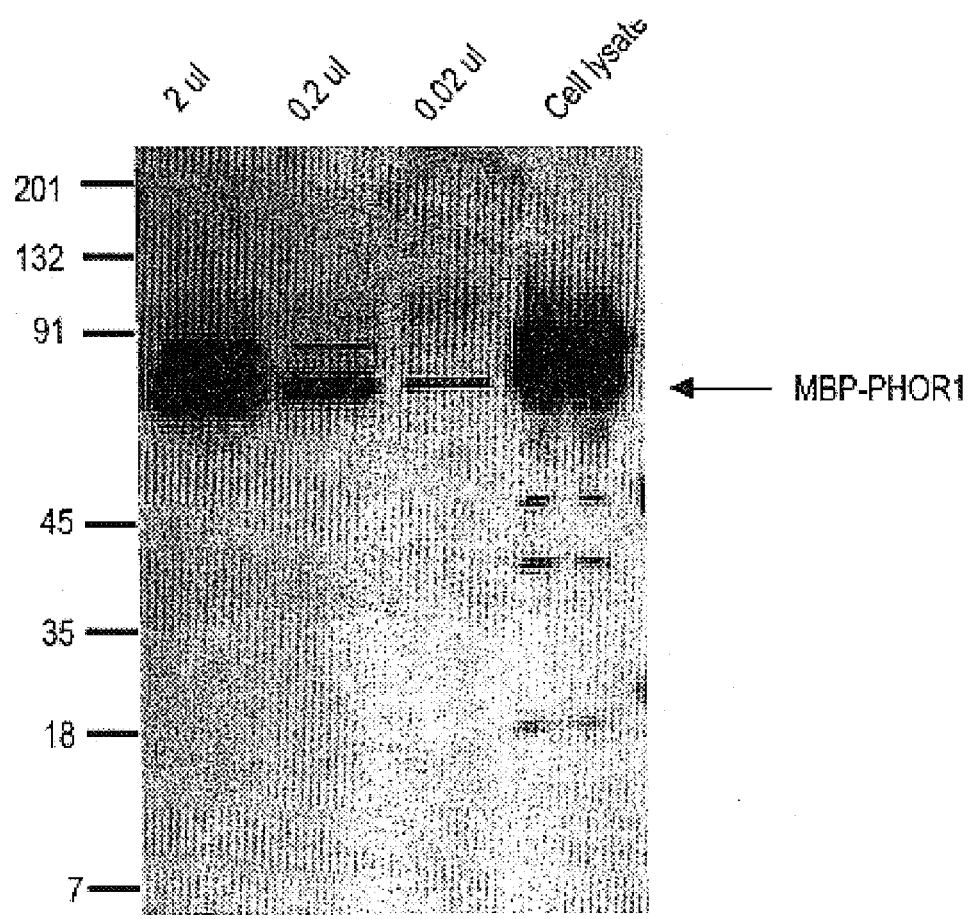
FIG. 15. PHOR-1 specific reactivity of serum derived from mice immunized with GST-PHOR-1 antigen. Balb C mice were immunized with a glutathione-S-transferase (GST)-PHOR-1 fusion protein encoding amino acids 86–310 of the PHOR-1 protein sequence. Specific reactivity of immunized mouse serum to the PHOR-1 protein sequence was determined by western blotting using a maltose binding protein (MBP)-PHOR-1 fusion protein encoding the same amino acids as target antigen. A 1:500 dilution of a representative test bleed was used to probe a blot of various amounts of purified MBP-PHOR-1 protein (2 μl=~100 ng of fusion protein) and induced bacterial lysates. Shown is specific recognition of the MBP-PHOR-1 protein demonstrating PHOR-1-specific antibodies in the immunized mouse serum.
Figure 16A:
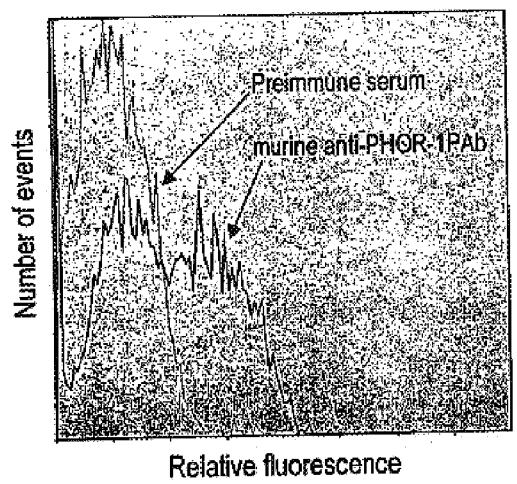
FIG. 16A. Detection of PHOR-1 cell surface expression on LNCaP tumor cells. LNCaP cells were stained with a 1:200 dilution of either a combination of sera derived from nice immunized with GST-PHOR-1 or with mouse preimmune sera followed by anti-mouse FITC conjugated anti-mouse secondary antibody. Stained cells were then analyzed on a Coulter EPICS XL flow cytometer. Indicated with arrows are the respective fluorescent profiles of cells populations stained with either preimmune sera (solid line) or GST-PHOR-1 immunized sera (dotted line). These results demonstrate recognition of endogenous cell surface PHOR-1 expression in LNCaP prostate cancer cells.
Figure 16B:
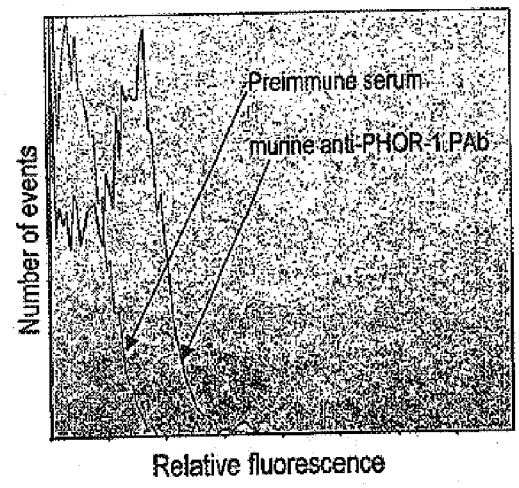
FIG. 16B. Detection of PHOR-1 cell surface expression on LAPC9 tumor cells. LAPC9 tumor cells prepared from an LAPC9 SCID mouse xenograft were stained with a 1:200 dilution of either a combination of sera derived from mice immunized with GST-PHOR-1 or with mouse preimmune sera followed by anti-mouse FITC conjugated anti-mouse secondary antibody. Stained cells were then analyzed on a Coulter EPICS XL flow cytometer. Indicated with arrows are the respective fluorescent profiles of cells populations stained with either preimmune sera (solid line) or GST-PHOR-1 immunized sera (dotted line). These results demonstrate recognition of endogenous cell surface PHOR-1 expression in LAPC9 prostate cancer cells.

To generate mAbs to PHOR-1, Balb C mice were immunized intraperitoneally with 200 μg of GST-PHOR-1 fusion protein mixed in complete Freund's adjuvant. Mice were then subsequently immunized every 2–4 weeks with 200 μg of antigen mixed in Freund's incomplete adjuvant. After 3 immunizations the titers of test bleeds from these mice were at least $1.2 \times 10^6$ determined by ELISA and specifically recognized the PHOR-1 amino acid sequence as shown by western blotting using a MBP-fusion protein encoding the same amino acids present in the GST-fusion (FIG. 15). Flow cytometric analysis of LNCaP cells and LAPC9 xenograft cells show a fluorescence shift when stained with a combination of immunized mouse bleeds compared to their cognate preimmune sera demonstrating cell surface detection of PHOR-1 protein (FIGS. 16A–B).

Once appropriate reactivity and specificity are obtained as determined by ELISA, western blotting and flow cytometry analyses, fusion and hybridoma generation is then carried out with established procedures well known in the art (Harlow and Lane, 1988).

Alternative antigens and immunization strategies may also be used to generate mAbs with specific reactivity and specificity to various regions of the PHOR-1 protein. Such antigens may include additional peptides and bacterial or baculovirus produced recombinant proteins encoding various regions of the PHOR-1 protein sequence. A cell based immunization strategy may also be used in which the PHOR-1 cDNA is overexpressed in cells such as NIH3T3 mouse fibroblasts or 300.19 murine B cells and whole cells or membrane preparations from these cells are used as immunogen.

Example 9

Characterization of PHOR-1 Protein Expression 293T cells were transiently transfected with the expression plasmid pCDNA4 HIS/MAX (Invitrogen) in which the PHOR-1 cDNA is fused at the amino terminus to two epitope tags, Express and His G. Empty vector control and PHOR-1 transfected cells were stained with a mAb that specifically recognizes the N-terminal Express epitope or with a rabbit pAb directed to the N-terminal 14 amino acids of the PHOR-1 sequence. As shown in FIG. 13A and FIGS. 14A–B, PHOR-1 transfected cells demonstrate a specific fluorescent shift compared to control cells with both the anti-Express mAb and the pAb. This shift indicates that PHOR-1 is expressed at the cell surface with the N-terminus exposed on the outside of the plasma membrane, which is consistent with the topology of known G protein coupled receptors. The expression of PHOR-1 by these cells was further confirmed by immunohistochemistry (see next example).

Figure 13B:
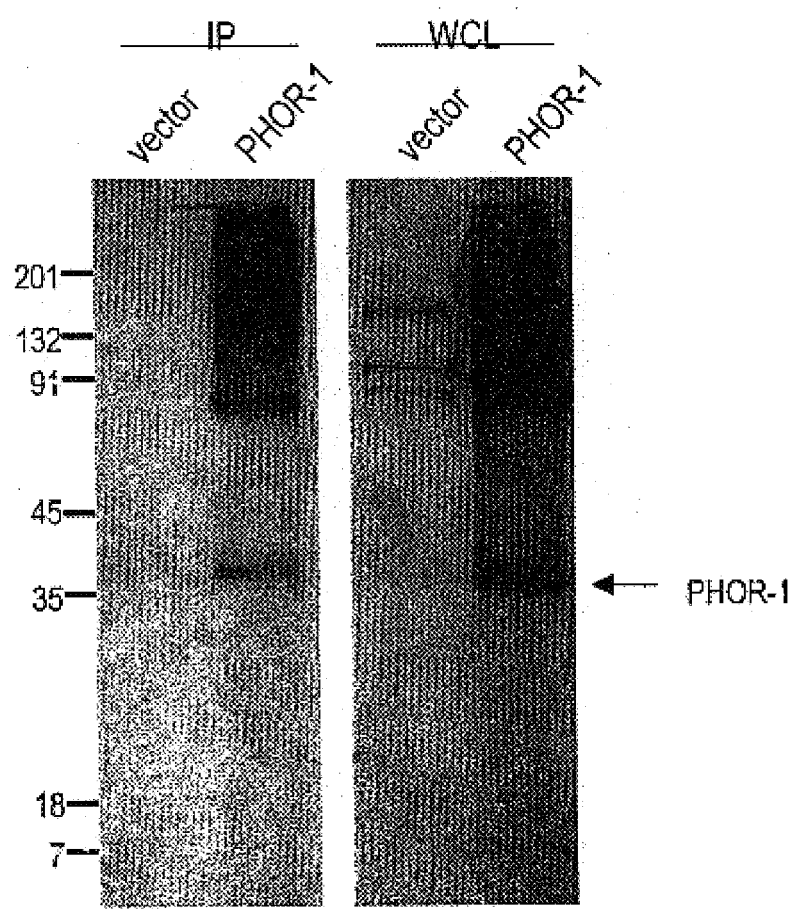
FIG. 13B. Expression and detection of PHOR-1 protein in PHOR-1-293T cells. 293T cells were transfected as described for FIG. 13A, and assayed for PHOR-1 protein expression by immunoprecipitation (IP) and western blotting. For immunoprecipitation and western analyses, PHOR-1 and vector control cells were harvested and lysed in either RIPA buffer (25 mM Tris pH 7.5, 150 mM NaCl, 1% Triton-X 100, 0.5% sodium deoxycholate, 1% SDS, 2 mM EDTA, 100 μg/ml PMSF, 2 μg/ml leupeptin, and 2 mM sodium orthovanadate) for immunoprecipitation or in 2X SDS-PAGE sample buffer for whole cell lysate (WCL) western analysis. RIPA lysates were pre-cleared with protein G agarose beads and then immununoprecipitated with 4 μg of affinity purified PHOR-1 anti-peptide rabbit pAb and protein G agarose beads. Immnunoprecipitated PHOR-1 protein (IP) and PHOR-1 protein present in whole cell lysates (WCL) was detected by western analysis with anti-express mAb followed by goat anti-mouse-HRP secondary antibody and visualized by enhanced chemiluminescence and exposure to autoradiographic film. Arrow indicates the predicted 37 kD PHOR-1 epitope-tagged protein detected by the anti-Express mAb. A high molecular weight smear was also detected in PHOR-1 transfected cells but not control cells, which may represent aggregates of the PHOR-1 protein induced by association of hydrophobic transmembrane regions. These results demonstrate cell surface expression and recognition of PHOR-1 protein in transfected cells.
Figure 14A:
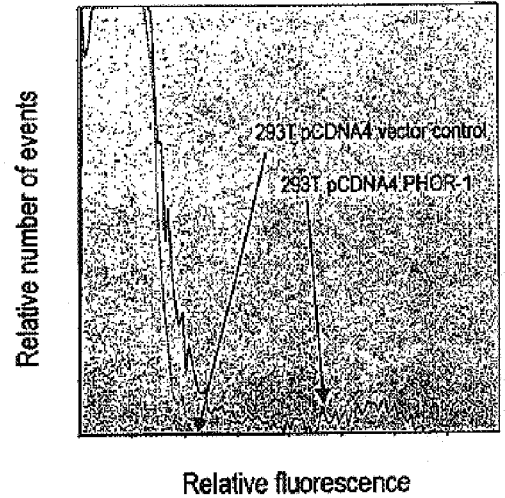
FIG. 14A. Flow cytometric detection of cell surface expression of PHOR-1 protein by a PHOR-1-specific polyclonal antibody. Affinity purified anti-PHOR-1 peptide pAb raised to amino acids 1-14 of the PHOR-1 sequence was used to detect epitope-tagged PHOR-1 protein expressed in transiently transfected 293T cells. 293T cells were transfected with either vector control or pCDNA4 HIS-MAX PHOR-1 plasmid (10 μg) and harvested 2 days later. Cells were then stained with 10 μg/ml of anti-Express mAb followed by anti-mouse FITC conjugated secondary Ab and analyzed on a Coulter EPICS XL flow cytometer. Indicated with arrows are the respective fluorescent profiles of control (dotted line) and PHOR-1 transfected (solid line) cell populations.
Figure 14B:
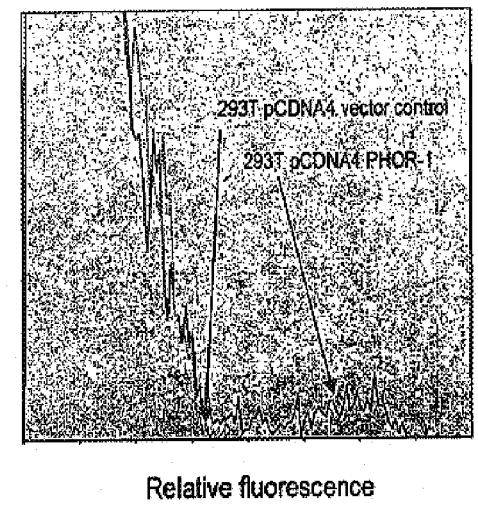
FIG. 14B. Flow cytometric detection of cell surface expression of PHOR-1 protein by a PHOR-1-specific polyclonal antibody. Affinity purified anti-PHOR-1 peptide pAb raised to amino acids 1–14 of the PHOR-1 sequence was used to detect epitope-tagged PHOR-1 protein expressed in transiently transfected 293T cells. 293T cells were transfected with either vector control or pCDNA4 HIS-MAX PHOR-1 plasmid (10 μg) and harvested 2 days later. Cells were then stained with 10 μg/ml of affinity purified rabbit anti-PHOR-1 pAb followed by anti-rabbit-FITC conjugated secondary Ab and analyzed on a Coulter EPICS XL flow cytometer. Indicated with arrows are the respective fluorescent profiles of control (dotted line) and PHOR-1 transfected (solid line) cell populations.

Immunoprecipitation and western analysis of epitope-tagged PHOR-1 protein from transfected cells shows an immunoreactive band of 37 kD that matches the predicted molecular weight of the PHOR-1 protein deduced from the amino acid sequence (FIG. 13B). In addition, a high molecular weight immunoreactive smear is seen in PHOR-1 transfected cells that may represent SDS and heat insoluble aggregates of the protein mediated by hydrophobic interaction of the 7 transmembrane domains.

Serum from mice immunized with GST-PHOR-1 protein was used to examine endogenous PHOR-1 protein expression. LNCaP and LAPC9 prostate cancer cells, both of which express PHOR-1 mRNA, exhibit a fluorescence shift when stained with immune sera compared to preimmune serum demonstrating cell surface expression of PHOR-1 protein in these cell populations (FIG. 16). In addition, the next example demonstrates use of this serum to detect endogenous expression of PHOR-1 in normal prostate, prostate cancer and prostate cancer cell lines.

Figure 17:
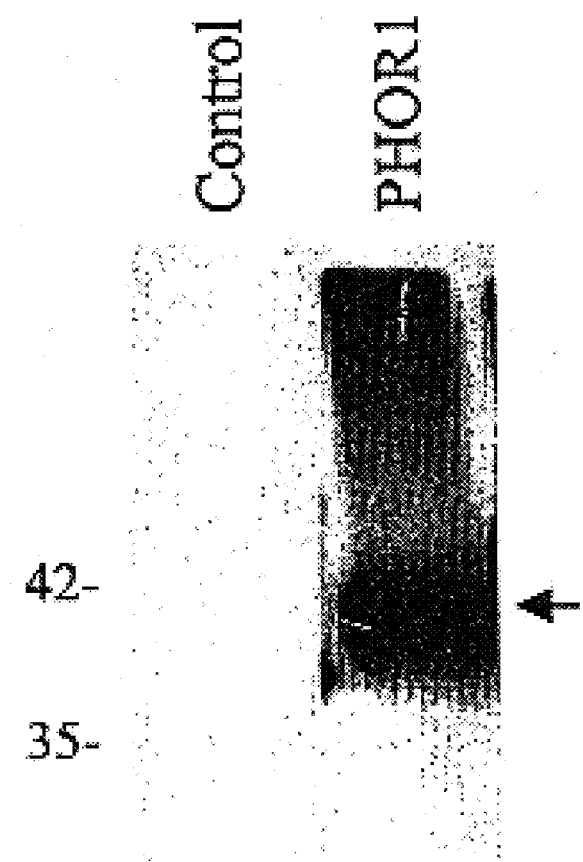
FIG. 17. PHOR-1 expression evaluated by cell free in vitro translation. Control cDNA and PHOR-1 cDNA were translated in vitro using rabbit reticulocyte lysates. The cell free in vitro translation assay demonstrates that the PHOR-1 cDNA is translated into a 38–42 kDa protein, which corresponds to the calculated molecular weight of PHOR-1.

PHOR-1 expression was evaluated by cell free in vitro translation. Control cDNA and PHOR-1 cDNA were translated in vitro using rabbit reticulocyte lysates in accordance with the manufacturer's recommendations (Promega, Madison, Wis.). The cell free in vitro assay results are shown in FIG. 17, and demonstrate that the PHOR-1 cDNA is translated into a 38–42 kDa protein, which corresponds to the calculated molecular weight of PHOR-1.

Example 10

Immunohistochemical Detection of PHOR-1 in Normal Prostate, Prostate Cancer and Prostate Cancer Cell Lines Methods Formalin-fixed, paraffin-embedded tissue blocks were sectioned at 4 microns and placed onto positively charged Capillary Gap microscope slides (Ventana Medical Systems, Inc., Tucson, Ariz.). After dewaxing in xylene, followed by hydration through alcohol series, tissue sections were pretreated in a steamer for 20 minutes in the presence of sodium citrate (10 mM, pH 6.0) followed by a 10 minute, proteinase K (1:40) incubation in order to optimize antibody reactivity. After cooling for. 5 minutes, the slides were immunostained using a biotin-streptavidin-peroxidase technique. Briefly, slides were incubated in blocking serum (normal goat) for 5 minutes, followed by 2 μg/ml anti-PHOR-1 rabbit polyclonal primary antibody (25 minutes), biotinylated secondary antibody-goat-anti-rabbit IgG (25 min), endogenous peroxidase blocking (3×1.5 minutes), and streptavidin complex conjugated to peroxidase enzyme, Vector Labs, Burlingame, Calif. (10 minutes). Between each incubation, sections were rinsed in buffer. DAB-Diaminobenzidine chromogen (QualTek Molecular Labs) was used to develop the reaction—yielding a brown precipitate. Slides were subsequently counterstained with hematoxylin and cover-slipped.

Results

Figure 18:
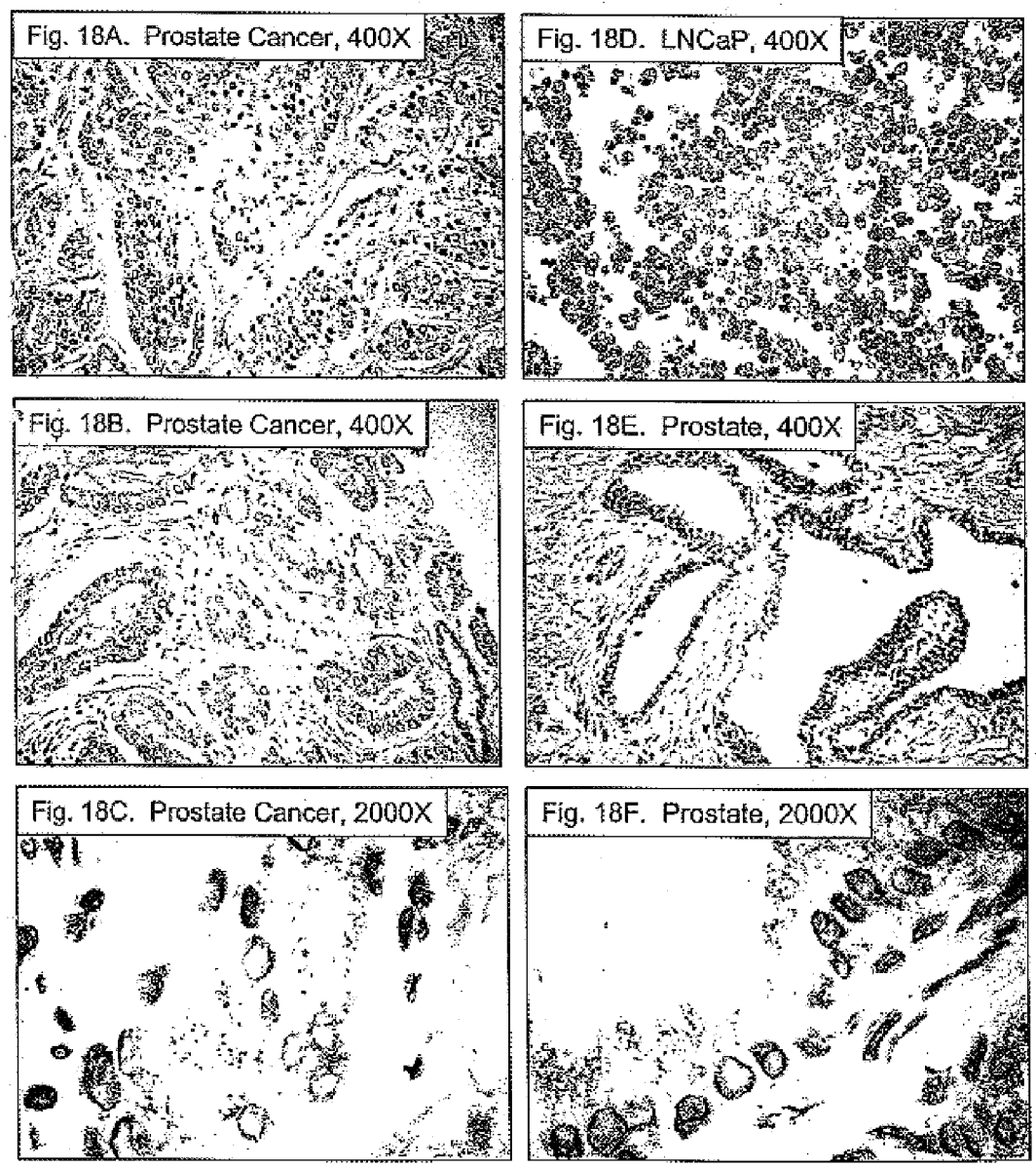
FIG. 18A. Photomicrograph showing immunohistochemical analysis using anti-PHOR-1 (peptide 1; amino acids 1–14) rabbit polyclonal antibody on formalin fixed and paraffin embedded prostate cancer tissues.
FIG. 18B. Photomicrograph showing immunohistochemical analysis using anti-PHOR-1 (peptide 1; amino acids 1–14) rabbit polyclonal antibody on formalin fixed and paraffin embedded prostate cancer cell line, LNCaP.
FIG. 18C. Photomicrograph showing immunohistochemical analysis using anti-PHOR-1 (peptide 1; amino acids 1–14) rabbit polyclonal antibody on formalin fixed and paraffin embedded prostate cancer tissues.
FIG. 18D. Photomicrograph showing immunohistochemical analysis using anti-PHOR-1 (peptide 1; amino acids 1–14) rabbit polyclonal antibody on formalin fixed and paraffin embedded normal prostate.
FIG. 18E. Photomicrograph showing immunohistochemical analysis using anti-PHOR-1 (peptide 1; amino acids 1–14) rabbit polyclonal antibody on formalin fixed and paraffin embedded prostate cancer tissues.
FIG. 18F. Photomicrograph showing immunohistochemical analysis using anti-PHOR-1 (peptide 1; amino acids 1–14) rabbit polyclonal antibody on formalin fixed and paraffin embedded normal prostate.

Endogenous expression of the PHOR-1 protein is demonstrated in the immunohistochemistry analysis of the anti-PHOR-1 (PEPTIDE 1: amino acids 1–14) rabbit polyclonal antibody (FIGS. 18A–F). Staining in prostate cancer is greater than the staining observed in normal prostate. The staining is localized apically within the luminal epithelia of the normal prostate (FIGS. 18E and 18F). The staining observed in prostate cancer is also localized apically in low to intermediate grade cancer (FIGS. 18B and 18C) and throughout all cells of more advanced prostate cancer (FIG. 18A). The prostate cancer cell line, LNCaP also shows similar staining (FIGS. 18D and 19F) in almost all cells.

Figure 19:
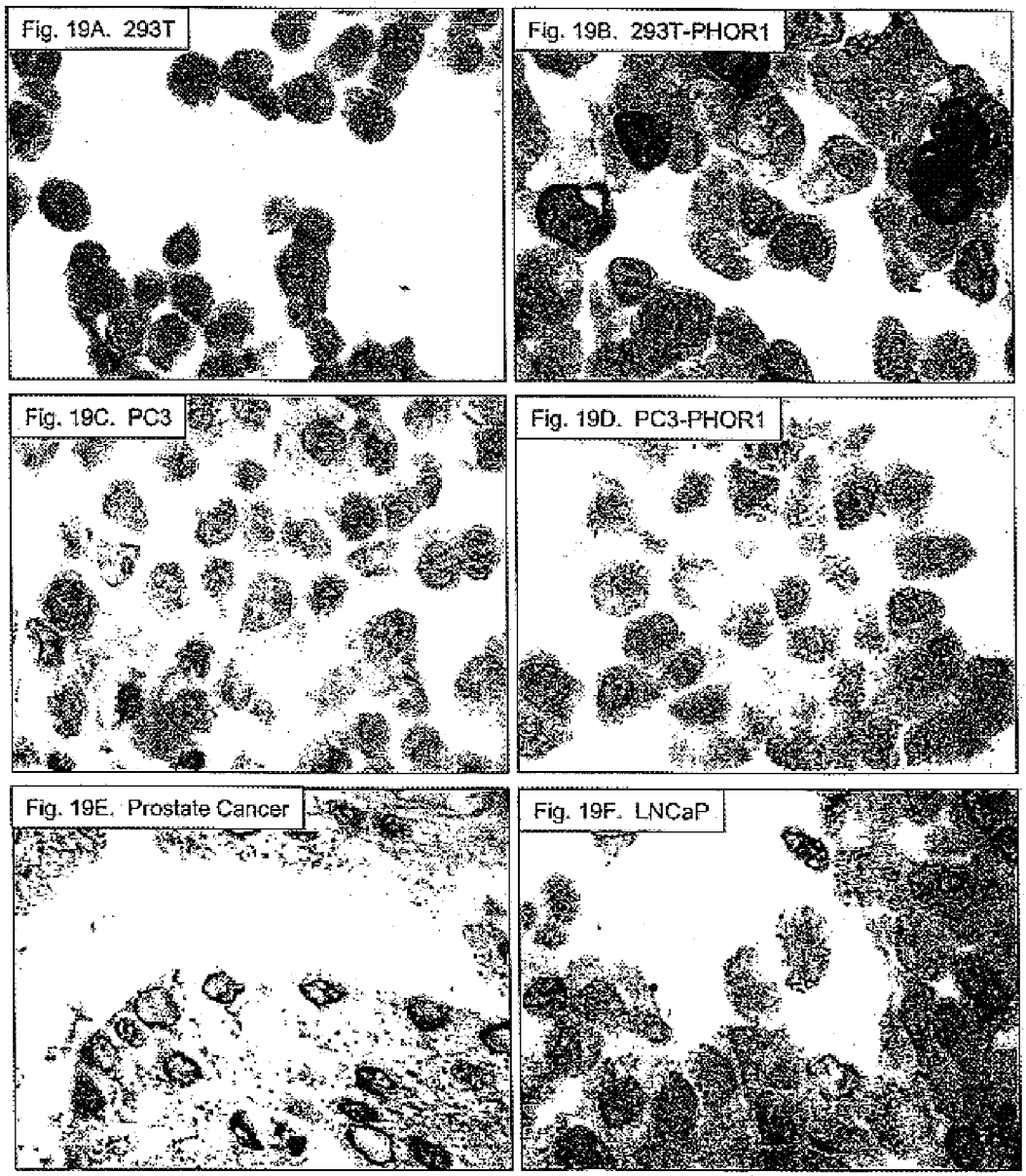
FIG. 19A. Photomicrograph showing immunohistochemical analysis using anti-PHOR-1 (peptide 1; amino acids 1–14) rabbit polyclonal antibody on formalin fixed and paraffin embedded 293T cells.
FIG. 19B. Photomicrograph showing immunohistochemical analysis using anti-PHOR-1 (peptide 1; amino acids 1–14) rabbit polyclonal antibody on formalin fixed and paraffin embedded 293T cells engineered to express PHOR-1.
FIG. 19C. Photomicrograph showing immunohistochemical analysis using anti-PHOR-1 (peptide 1; amino acids 1–14) rabbit polyclonal antibody on formalin fixed and paraffin embedded PC3 cells.
FIG. 19D. Photomicrograph showing immunohistochemical analysis using anti-PHOR-1 (peptide 1; amino acids 1–14) rabbit polyclonal antibody on formalin fixed and paraffin embedded PC3 cells engineered to express PHOR-1.
FIG. 19E. Photomicrograph showing immunohistochemical analysis using anti-PHOR-1 (peptide 1; amino acids 1–14) rabbit polyclonal antibody on formalin fixed and paraffin embedded prostate cancer tissue.
FIG. 19F. Photomicrograph showing immunohistochemical analysis using anti-PHOR-1 (peptide 1; amino acids 1–14) rabbit polyclonal antibody on formalin fixed and paraffin embedded LNCaP cells.

The specificity of the anti-PHOR-1 (PEPTIDE 1) rabbit polyclonal antibody is demonstrated in FIGS. 19A–F. The engineered cell line 293T-PHOR-1 (FIG. 19B), which expresses PHOR-1 protein from the episomal pcDNA4 HIS/MAX construct, and the PC3-PHOR-1 cell line (FIG. 19D), which expresses PHOR-1 stably from a integrated pSRα construct, both show specific brown staining that is not present in the parental, non-engineered cell lines (FIGS. 19A and 19C, respectively). The staining in the 293T-PHOR-1 cell line (FIG. 19B) is very strong in a subset of cells, as is expected from a transient transfection with a pcDNA4 HIS/MAX construct which drives expression of PHOR-1 from a CMV promoter. However, the staining in the cell line PC3-PHOR-1 (FIG. 19D) is present in all cells observed, as is expected in a stable cell line.

These data demonstrate that the anti-PHOR-1 (PEPTIDE 1) rabbit polyclonal antibody specifically recognizes the PHOR-1 protein. In addition, the staining observed in PC3-PHOR-1 (FIG. 19D) closely resembles the staining pattern and intensity seen in the prostate cancer cell line LNCaP (FIG. 19F) and in prostate cancer (FIG. 19E).

Example 11

Alteration of Tyrosine and Erk Phosphorylation by PHOR-1

PC3 cells, stably expressing either neo or PHOR-1 in the pSRα retroviral vector, were grown in 1% FBS overnight. The cells were then either left untreated or were treated with 10% FBS for 3 min. The cells were lysed and analyzed by western blotting with anti-phosphotyrosine (UBI, Lake Placid, N.Y.) (FIG. 20A), or anti-phospho-Erk (Cell Signal, Beverly, Mass.) mAb (FIG. 20B). Anti-Grb2 mAb (Transduction Laboratories, San Diego, Calif.) overlay shows equal protein loading (FIG. 20C). In FIG. 20D, PHOR-1 expression was evaluated by northern blotting. (See also FIG. 19D for immunohistochemical demonstration of PHOR-1 expression by PC3-PHOR-1 cells.) RNA was extracted from control PC3-neo cells and PC3 cells stably transduced with PHOR-1 and the RNA blots were hybridized using PHOR-1 probe (Xba-Ecor1 fragment of clone GTH10). RNA from LAPC4 xenografts was used as a positive control (FIG. 20E). The results show that the PHOR-1 mRNA is expressed in retroviral transduced PC3-PHOR-1 cells, but not in control cells, and that, once expressed, PHOR-1 alters the phosphorylation pattern of PC3 cells.

Tyrosine phosphorylation plays an important role in transmitting signaling events from the cell surface to the nucleus. Moreover, tyrosine phosphorylation has been shown to occur via GPCR (Liebmann C, Bohmer F D. Curr Med. Chem. 2000,7:911 and Maudsley S, Pierce K L, Zamah A M, Miller W E, Ahn S, Daaka Y, Lefkowitz R J, Luttrell L M. J. Biol. Chem. 2000, 275:9572), and results in the activation of signaling cascades that contribute to the effect of the GPCR. These results (shown in FIGS. 20A–B) indicate that, when PHOR-1 is expressed in PC3 cells, it induces the tyrosine phosphorylation of a protein of 55 kDa and the de-phosphorylation of a 130 kDA protein. In addition, expression of PHOR-1 induces a 2–3 fold increase in the phosphorylation of Erk, a protein associated with mitogenesis and transformation (Greulich H, Erikson R L, J Biol Chem. 1998;273:13280), indicating that PHOR-1 activates the Erk cascade.

Example 12

PHOR-1 Modulates the Cytoplasmic Concentration of cAMP

Parental cells and cells expressing PHOR-1 were compared for their ability to induce cytoplasmic accumulation of CAMP. 293T cells were transfected with empty pcDNA4 HIS MAX vector or with pcDNA4 HIS MAX PHOR-1. Cells were starved in 1% fetal bovine serum (FBS) overnight and incubated with media alone or in the presence of 10% FBS. The cells were lysed and analyzed for CAMP content by enzyme linked immunoassay (EIA) according to the manufacturer's recommendations (Linco Research, St Charles, Mich.). The results are shown in Table 1, and indicate that expression of PHOR-1 alters the CAMP concentration in response to FBS.

TABLE 1

| Sample | cAMP, nM |
|---|---|
| 293T + FBS | 20.59 |
| 293T-PHOR-1 + FBS | 43.08 |
| LAPC4 AD | 46.12 |
| LAPC4 AI | 63.12 |

All characterized GPCRs, including the olfactory receptors, function by activating the CAMP pathway. In the absence of ligand, GPCRs are normally in an inactive state. Upon ligand binding or overexpression, GPCRs acquire an active conformation and complex with G proteins. This interaction results in the dissociation of G protein subunits and the activation of adenylate cyclase, resulting in CAMP accumulation (Birnbaumer L, Cell 1992, 71:1069). Enhanced production of CAMP results in the activation of several downstream signaling pathways that mediate the effect of GPCRs. The demonstration in this example that expression of PHOR-1 in 293T cells allows the accumulation of CAMP in response to FBS indicates that PHOR-1 functions as a GPCR under these conditions.

In addition, CAMP content was determined for two prostate cancer xenografts that differ in their androgen dependence and PHOR-1 expression. LAPC4AD is an androgen dependent prostate cancer xenograft that exhibits strong PHOR-1 expression, as evidenced by the northern blot shown in FIG. 20E. The CAMP content of these cells, also shown in the Table above, was significantly lower than that of LAPC4AI cells, which are androgen independent and do not express PHOR-1.

Example 13
PHOR-1 Induces Colony Growth in Soft Agar

NIH-3T3 cells stably expressing PHOR-1 were analyzed for their ability to form colonies in soft agar. NIH-3T3 cells, stably expressing neo or activated-Ras were used as negative and positive controls, respectively. The experiment was performed in duplicate. The assay was evaluated 4 weeks after cell plating. The results are shown in FIG. 21 and in Table 2.

TABLE 2

| Cells | Number of Colonies | |
|---|---|---|
| | Average | S.D. |
| 3T3-Neo | 39 | 12.7 |
| 3T3-PHOR | 131 | 15.6 |
| 3T3-Ras | 246 | 8.5 |

The colony count shows that PHOR-1 induces a 3-fold increase in colony formation relative to neo control. This significant increase has been observed in 2 separate experiments. These results indicate that expression of PHOR-1 in NIH 3T3 cells induces a 3–4 fold increase in colony formation as compared to a 5-fold increase by the strong oncogene Ras, suggesting that PHOR-1 has significant transforming capabilities.

Example 14
Chromosomal Mapping of the PHOR-1 Gene

The chromosomal localization of PHOR-1 was determined using the GeneBridge4 radiation hybrid panel (Walter et al., 1994, Nat. Genetics 7:22) (Research Genetics, Huntsville Ala.). The following PCR primers were used to localize PHOR-1 SEQ ID NO: 31, 32, respectively):

101P3A11.1 ATCCTGACTAGGTTGTGGTTGGAG

101P3A11.2 TGTGGTTGGGAGTTCTAAAGAGGA

The resulting mapping vector for the 93 radiation hybrid panel DNAs was: 1000000001001000011010000 111101000 1000020101010000110000000100001110000100 00000111101100001111

This vector and the mapping program at http://www-genome.wi.mit.edu/cgi-bin/contig/rhmapper. placed PHOR-1 to the telomere of chromosome 11 at 11p15.5.

Because the human PHOR-1 gene maps to chromosome 11 at 11p15.5, polynucleotides encoding different regions of the PHOR-1 protein can be used to characterize cytogenetic abnormalities on chromosome 11, band p15.5 that have been identified as being associated with various cancers. In particular, a variety of chromosomal abnormalities in 11p15.5 have been identified as frequent cytogenetic abnormalities in a number of different cancers (see, e.g., Lai et al., 2000, Clin. Cancer Res. 6(8):3172–6; Oya and Schulz, 2000, Br. J. Cancer 83(5):626–31; Svaren et al., Sept. 12 2000, J. Biol. Chem.). Consequently, polynucleotides encoding specific regions of the PHOR-1 protein provide new tools that can be used to delineate with a greater precision than previously possible, the specific nature of the cytogenetic abnormalities in this region of chromosome 11 that may contribute to the malignant phenotype. In this context, these polynucleotides satisfy a need in the art for expanding the sensitivity of chromosomal screening in order to identify more subtle and less common chromosomal abnormalities (see, e.g., Evans et al., 1994, Am. J. Obstet. Gynecol. 171(4):1055–1057).

Example 15
Identification of Potential Signal Transduction Pathways

To determine whether PHOR-1 directly or indirectly activates known signal transduction pathways in cells, luciferase (luc) based transcriptional reporter assays are carried out in cells expressing PHOR-1. These transcriptional reporters contain consensus binding sites for known transcription factors that lie downstream of well characterized signal transduction pathways. The reporters and examples of their associated transcription factors, signal transduction pathways, and activation stimuli are listed below.

1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, $p^{53}$; SAPK; growth/differentation/apoptosis
6. CRE-luc, CREB/ATF2; PKA/p38; growth/apoptosis/stress PHOR-1-mediated effects may be assayed in cells showing mRNA expression. Luciferase reporter plasmids may be introduced by lipid mediated transfection (TFX-50, Promega). Luciferase activity, an indicator of relative transcriptional activity, is measured by incubation of cell extracts with luciferin substrate and luminescence of the reaction is monitored in a luminometer.

Example 16
In Vitro Assays of PHOR-1 Function

The expression of PHOR-1 in prostate cancer provides evidence that this gene has a functional role in tumor progression and/or tumor initiation. It is possible that PHOR-1 functions as a receptor involved in activating proliferation signals. PHOR-1 function can be assessed in mammalian cells using in vitro approaches. For mammalian expression, PHOR-1 can be cloned into a number of appropriate vectors, including pcDNA 3.1 myc-His-tag and the retroviral vector pSRcttkneo (Muller et al., 1991, MCB 11:1785). Using such expression vectors, PHOR-1 can be expressed in several cell lines, including PC-3, NIH 3T3, LNCaP and 293T. Expression of PHOR-1 can be monitored using anti-PHOR-1 antibodies and northern blot analysis.

Mammalian cell lines expressing PHOR-1 can be tested in several in vitro and in vivo assays, including cell proliferation in tissue culture, activation of apoptotic signals, tumor formation in SCID mice, and in vitro invasion using a membrane invasion culture system (MICS; Welch et al.,Int. J. Cancer 43: 449–457). PHOR-1 cell phenotype is compared to the phenotype of cells that lack expression of PHOR-1.

Cell lines expressing PHOR-1 can also be assayed for alteration of invasive and migratory properties by measuring passage of cells through a matrigel coated porous membrane chamber (Becton Dickinson). Passage of cells through the membrane to the opposite side is monitored using a fluorescent assay (Becton Dickinson Technical Bulletin #428) using calcein-Am (Molecular Probes) loaded indicator cells. Cell lines analyzed include parental and PHOR-1 overexpressing PC3, NIH 3T3 and LNCaP cells. To determine whether PHOR-1-expressing cells have chemoattractant properties, indicator cells are monitored for passage through the porous membrane toward a gradient of PHOR-1 conditioned media compared to control media. This assay may also be used to qualify and quantify specific neutralization of the PHOR-1 induced effect by candidate cancer therapeutic compositions.

The function of PHOR-1 can be evaluated using anti-sense RNA technology coupled to the various functional assays described above, e.g. growth, invasion and migration. Anti-sense RNA oligonucleotides can be introduced into PHOR-1 expressing cells, thereby preventing the expression of PHOR-1. Control and anti-sense containing cells can be analyzed for proliferation, invasion, migration, apoptotic and transcriptional potential. The local as well as systemic effect of the loss of PHOR-1 expression can be evaluated.

Example 17
In Vivo Assay for PHOR-1 Tumor Growth Promotion

The effect of the PHOR-1 protein on tumor cell growth may be evaluated in vivo by gene overexpression in tumor-bearing mice. For example, SCID mice can be injected subcutaneously on each flank with $1 \times 10^6$ of either PC3, TSUPR1, or DU145 cells containing tkneo empty vector or PHOR-1. At least two strategies may be used: (1) Constitutive PHOR-1 expression under regulation of a promoter such as a constitutive promoter obtained from the genomes of viruses such as polyoma virus, fowlpox virus (UK 2,211, 504 published 5Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems, and (2) Regulated expression under control of an inducible vector system, such as ecdysone, tet, etc., provided such promoters are compatible with the host cell systems. Tumor volume is then monitored at the appearance of palpable tumors and followed over time to determine if PHOR-1 expressing cells grow at a faster rate and whether tumors produced by PHOR-1-expressing cells demonstrate characteristics of altered aggressiveness (e.g. enhanced metastasis, vascularization, reduced responsiveness to chemotherapeutic drugs). Additionally, mice may be implanted with $1 \times 10^5$ of the same cells orthotopically to determine if PHOR-1 has an effect on local growth in the prostate or on the ability of the cells to metastasize, specifically to lungs, lymph nodes, and bone marrow.

The assay is also useful to determine the PHOR-1 inhibitory effect of candidate therapeutic compositions, such as for example, PHOR-1 intrabodies, PHOR-1 antisense molecules and ribozymes.

Example 18
Cloning PHOR-1 Family Member Genes

PHOR-1 is homologous to a large family of olfactory receptors that are expressed in olfactory epithelium and neurons. In an attempt to identify additional genes that are homologous to PHOR-1, the protein sequence of PHOR-1 was used as an electronic probe to identify family members in the public EST (expression sequence tag) database (dBest). Using the "tblastn" function in NCBI (National Center for Biotechnology Information) the dBest database was queried with the PHOR-1 protein sequence. This analysis revealed one new family member (FIG. 22). The EST, AI138213, was isolated from a human placental library and is homologous to the carboxyl-terminal region of PHOR-1. It exhibits 49.5% identity with PHOR-1 over a 95 amino acid overlap. This novel family member is being analyzed for expression in prostate and prostate cancer samples and will be cloned from a human cDNA library.

An alternative approach to finding novel family members is to design degenerate oligonucleotides in conserved regions of the gene (Raming et al., 1993, Nature 361:353). These can then be used in RT-PCR reactions on first strand cDNA derived from prostate or prostate cancer to isolate novel GPCR family members. To isolate family members of PHOR-1 using RT-PCR, the following conserved regions were chosen for oligonucleotide design: SLHEPMY (a.a. 56–62; SEQ ID NO: 36), AMAFDRY (a.a. 119–125; SEQ ID NO: 37), YVAICHP (a.a. 125–131; SEQ ID NO: 38), KAFGTCV (a.a. 237–243; SEQ ID NO: 39), and GVIKT-KEI (a.a. 294–300; SEQ ID NO: 40). The degenerate oligonucleotides used are as follows:

(1) for SLHEPMY:

| | |
|---|---|
| 1A-5'AGYCTNCAYSMNCCNATGTAY3' | (SEQ ID NO: 41), |
| 1B-5'TCNCTNCAYSMNCCNATGTAY3' | (SEQ ID NO: 42), |
| 1C-5'AGYTTRCAYSMNCCNATGTAY3' | (SEQ ID NO: 43), |
| 1D-5'TCNTTRCAYSMNCCNATGTAY3' | (SEQ ID NO: 44); |

(2) for AMAFDRY:

| | |
|---|---|
| 2A-5'GCNATGGCNTTYGAYCGNTAY3' | (SEQ ID NO: 45), |
| 2B-5'GCNATGGCNTTYGAYAGRTAY3' | (SEQ ID NO: 46); |

(3) for YVAICHP:

| | |
|---|---|
| 3A-5'TAYGTNGCNATHTGYCAYCCN3' (sense) | (SEQ ID NO: 47), |
| 3B-5'NGGRTGRCADATNGCNACRTA3' (anti-sense) | (SEQ ID NO: 48); |

(4) for KAFGTCV:

| | |
|---|---|
| 4A-5'NACRCANGTNCCRAANGCYTT3' (anti-sense) | (SEQ ID NO: 49); |

(5) for GVKTEI:

| | |
|---|---|
| 5A-5'DATYTSYTTNGTYTTNRCNCC3' (anti-sense) | (SEQ ID NO: 50); | where (A) represents adenine, (C) cytosine, (G) guanine, (T) thymine, (R) adenine or guanine, (Y) cytosine or thymine, (S) cytosine or guanine, (D) adenine or guanine or thymine, (H) adenine or cytosine or thymine, (N) adenine or guanine or cytosine or thymine.

The following combination of primers are used to amplify family members from first strand cDNA: pool of 1A–1D & 3B; pool of 1A–1D & 4A; pool of 1A–1D & 5A; pool of 2A+2B & 4A; pool of 2A+2B & 5A; 3A & 4A; 3A & 5A. The resultant PCR products are then ligated into the PCR2.1 vector (Invitrogen) and subsequently transformed into DH5 E. coli. After blue/white selection and ampicillin selection on agar, white ampicillin resistant colonies are expanded in liquid culture for plasmid purification and sequencing of cDNA inserts. Sequences from these clones are compared to the PHOR-1 sequence and queried against available public and private databases. Sequences that represent novel PHOR-1 family members are singled out for further analysis and full length cloning.

Throughout this application, various publications are referenced. The disclosures of these publications are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

What is claimed is:

1. A method to screen the presence of cancer in a test prostate tissue of a subject, which method comprises (a) determining the level of PHOR-1 protein of SEQ. ID. NO: 2 in a sample of said test prostate tissue;

(b) providing the value of the level of PHOR-1 protein in a corresponding prostate tissue without cancer; and (c) comparing the level of PHOR-1 protein determined in (a) to the level provided in (b)

whereby a greater level in (a) as compared to (b) indicates the presence of cancer in said test tissue.

2. The method of claim 1 wherein said level of PHOR-1 protein is determined by a method which comprises contacting the sample with an agent which binds said PHOR-1 protein specifically; and detecting the level of binding of said agent to the sample; wherein said agent is an antibody or fragment thereof.

3. The method of claim 1, wherein the level of PHOR-1 protein is determined qualitatively.

* * * * *

SEQUENCE LISTING

<160> NUMBER OF SEQ ID NOS: 50

<210> SEQ ID NO 1
<211> LENGTH: 3136
<212> TYPE: DNA
<213> ORGANISM: Homo Sapiens
<220> FEATURE:
<221> NAME/KEY: CDS
<222> LOCATION: (133)...(1083)

<400> SEQUENCE: 1

```
cagagaggct gtatttcagt gcagcctgcc agacctcttc tggaggaaga ctggacaaag      60
ggggtcacac attccttcca tacggttgag cctctacctg cctggtgctg gtcacagttc     120
agcttcttca tg atg gtg gat ccc aat ggc aat gaa tcc agt gct aca tac     171
             Met Val Asp Pro Asn Gly Asn Glu Ser Ser Ala Thr Tyr
                 1               5                  10 ttc atc cta ata ggc ctc cct ggt tta gaa gag gct cag ttc tgg ttg        219
Phe Ile Leu Ile Gly Leu Pro Gly Leu Glu Glu Ala Gln Phe Trp Leu
         15                  20                  25 gcc ttc cca ttg tgc tcc ctc tac ctt att gct gtg cta ggt aac ttg        267
Ala Phe Pro Leu Cys Ser Leu Tyr Leu Ile Ala Val Leu Gly Asn Leu
 30                  35                  40                  45 aca atc atc tac att gtg cgg act gag cac agc ctg cat gag ccc atg        315
Thr Ile Ile Tyr Ile Val Arg Thr Glu His Ser Leu His Glu Pro Met
                 50                  55                  60 tat ata ttt ctt tgc atg ctt tca ggc att gac atc ctc atc tcc acc        363
Tyr Ile Phe Leu Cys Met Leu Ser Gly Ile Asp Ile Leu Ile Ser Thr
             65                  70                  75 tca tcc atg ccc aaa atg ctg gcc atc ttc tgg ttc aat tcc act acc        411
Ser Ser Met Pro Lys Met Leu Ala Ile Phe Trp Phe Asn Ser Thr Thr
         80                  85                  90 atc cag ttt gat gct tgt ctg cta cag att ttt gcc atc cac tcc tta        459
Ile Gln Phe Asp Ala Cys Leu Leu Gln Ile Phe Ala Ile His Ser Leu
     95                 100                 105 tct ggc atg gaa tcc aca gtg ctg ctg gcc atg gct ttt gac cgc tat        507
Ser Gly Met Glu Ser Thr Val Leu Leu Ala Met Ala Phe Asp Arg Tyr
110                 115                 120                 125 gtg gcc atc tgt cac cca ctg cgc cat gcc aca gta ctt acg ttg cct        555
Val Ala Ile Cys His Pro Leu Arg His Ala Thr Val Leu Thr Leu Pro
                130                 135                 140 cgt gtc acc aaa att ggt gtg gct gct gtg gtg cgg ggg gct gca ctg        603
Arg Val Thr Lys Ile Gly Val Ala Ala Val Val Arg Gly Ala Ala Leu
            145                 150                 155 atg gca ccc ctt cct gtc ttc atc aag cag ctg ccc ttc tgc cgc tcc        651
Met Ala Pro Leu Pro Val Phe Ile Lys Gln Leu Pro Phe Cys Arg Ser
        160                 165                 170 aat atc ctt tcc cat tcc tac tgc cta cac caa gat gtc atg aag ctg        699
Asn Ile Leu Ser His Ser Tyr Cys Leu His Gln Asp Val Met Lys Leu
    175                 180                 185 gcc tgt gat gat atc cgg gtc aat gtc gtc tat ggc ctt atc gtc atc        747
Ala Cys Asp Asp Ile Arg Val Asn Val Val Tyr Gly Leu Ile Val Ile
190                 195                 200                 205 atc tcc gcc att ggc ctg gac tca ctt ctc atc tcc ttc tca tat ctg        795
Ile Ser Ala Ile Gly Leu Asp Ser Leu Leu Ile Ser Phe Ser Tyr Leu
                210                 215                 220 ctt att ctt aag act gtg ttg ggc ttg aca cgt gaa gcc cag gcc aag        843
Leu Ile Leu Lys Thr Val Leu Gly Leu Thr Arg Glu Ala Gln Ala Lys
            225                 230                 235
```

-continued

| | | |
|---|---|---|
| gca ttt ggc act tgc gtc tct cat gtg tgt gct gtg ttc ata ttc tat<br>Ala Phe Gly Thr Cys Val Ser His Val Cys Ala Val Phe Ile Phe Tyr<br>240                               245                           250 | 891 |
| gta cct ttc att gga ttg tcc atg gtg cat cgc ttt agc aag cgg cgt<br>Val Pro Phe Ile Gly Leu Ser Met Val His Arg Phe Ser Lys Arg Arg<br>255                             260                        265 | 939 |
| gac tct ccg ctg ccc gtc atc ttg gcc aat atc tat ctg ctg gtt cct<br>Asp Ser Pro Leu Pro Val Ile Leu Ala Asn Ile Tyr Leu Leu Val Pro<br>270                        275                       280                      285 | 987 |
| cct gtg ctc aac cca att gtc tat gga gtg aag aca aag gag att cga<br>Pro Val Leu Asn Pro Ile Val Tyr Gly Val Lys Thr Lys Glu Ile Arg<br>                   290                       295                       300 | 1035 |
| cag cgc atc ctt cga ctt ttc cat gtg gcc aca cac gct tca gag ccc<br>Gln Arg Ile Leu Arg Leu Phe His Val Ala Thr His Ala Ser Glu Pro<br>                   305                       310                       315 | 1083 |
| taggtgtcag tgatcaaact tcttttccat tcagagtcct ctgattcaga ttttaatgtt | 1143 |
| aacattttgg aagacagtat tcagaaaaaa aatttcctta ataaaaaata caactcagat | 1203 |
| ccttcaaata tgaaactggt tggggaatct ccatttttc aatattattt tcttctttgt | 1263 |
| tttcttgcta catataatta ttaatacccct gactaggttg tggttggagg gttattactt | 1323 |
| ttcattttac catgcagtcc aaatctaaac tgcttctact gatggtttac agcattctga | 1383 |
| gataagaatg gtacatctag agaacatttg ccaaaggcct aagcacggca aaggaaaata | 1443 |
| aacacagaat ataataaaat gagataatct agcttaaaac tataacttcc tcttcagaac | 1503 |
| tcccaaccac attggatctc agaaaaatgc tgtcttcaaa atgacttcta cagagaagaa | 1563 |
| ataattttc ctctggacac tagcacttaa ggggaagatt ggaagtaaag ccttgaaaag | 1623 |
| agtacattta cctacgttaa tgaaagttga cacactgttc tgagagttttt cacagcatat | 1683 |
| ggaccctgtt tttcctattt aatttctta tcaacccttt aattaggcaa agatattatt | 1743 |
| agtaccctca ttgtagccat gggaaaattg atgttcagtg gggatcagtg aattaaatgg | 1803 |
| ggtcatacaa gtataaaaat taaaaaaaaaa aaagacttca tgcccaatct catatgatgt | 1863 |
| ggaagaactg ttagagagac caacagggta gtgggttaga gatttccaga gtcttacatt | 1923 |
| ttctagagga ggtatttaat ttcttctcac tcatccagtg ttgtatttag gaatttcctg | 1983 |
| gcaacagaac tcatggcttt aatcccacta gctattgctt attgtcctgg tccaattgcc | 2043 |
| aattacctgt gtcttggaag aagtgatttc taggttcacc attatggaag attcttattc | 2103 |
| agaaagtctg catagggctt atagcaagtt atttatttt aaaagttcca taggtgattc | 2163 |
| tgataggcag tgaggttagg gagccaccag ttatgatggg aagtatggaa tggcaggtct | 2223 |
| tgaagataac attggccttt tgagtgtgac tcgtagctgg aaagtgaggg aatcttcagg | 2283 |
| accatgcttt atttggggct tgtgcagta tggaacaggg actttgagac caggaaagca | 2343 |
| atctgactta ggcatgggaa tcaggcattt tgcttctga ggggctatta ccaagggtta | 2403 |
| ataggtttca tcttcaacag gatatgacaa cagtgttaac caagaaactc aaattacaaa | 2463 |
| tactaaaaca tgtgatcata tatgtggtaa gtttcattt cttttcaat cctcaggttc | 2523 |
| cctgatatgg attcctataa catgctttca tccccttttg taatggatat catatttgga | 2583 |
| aatgcctatt taatacttgt atttgctgct ggactgtaag cccatgaggg cactgtttat | 2643 |
| tattgaatgt catctctgtt catcattgac tgctctttgc tcatcattga atcccccagc | 2703 |
| aaagtgccta gaacataata gtgcttatgc ttgacaccgg ttatttttca tcaaacctga | 2763 |
| ttccttctgt cctgaacaca tagccaggca attttccagc cttctttgag ttgggtatta | 2823 |
| ttaaattctg gccattactt ccaatgtgag tggaagtgac atgtgcaatt tctatacctg | 2883 |

```
gctcataaaa ccctcccatg tgcagccttt catgttgaca ttaaatgtga cttgggaagc    2943
tatgtgttac acagagtaaa tcaccagaag cctggatttc tgaaaaaact gtgcagagcc    3003
aaacctctgt catttgcaac tcccacttgt atttgtacga ggcagttgga taagtgaaaa    3063
ataaagtact attgtgtcaa gaaaaaaaaa aaaaaaaaaa aaaaaaaaaa aaaaaaaaaa    3123
aaaaaaaaaa aaa                                                      3136
```

<210> SEQ ID NO 2
<211> LENGTH: 317
<212> TYPE: PRT
<213> ORGANISM: Homo Sapiens

<400> SEQUENCE: 2

```
Met Val Asp Pro Asn Gly Asn Glu Ser Ser Ala Thr Tyr Phe Ile Leu
  1               5                  10                  15

Ile Gly Leu Pro Gly Leu Glu Glu Ala Gln Phe Trp Leu Ala Phe Pro
             20                  25                  30

Leu Cys Ser Leu Tyr Leu Ile Ala Val Leu Gly Asn Leu Thr Ile Ile
         35                  40                  45

Tyr Ile Val Arg Thr Glu His Ser Leu His Glu Pro Met Tyr Ile Phe
     50                  55                  60

Leu Cys Met Leu Ser Gly Ile Asp Ile Leu Ile Ser Thr Ser Ser Met
 65                  70                  75                  80

Pro Lys Met Leu Ala Ile Phe Trp Phe Asn Ser Thr Thr Ile Gln Phe
                 85                  90                  95

Asp Ala Cys Leu Leu Gln Ile Phe Ala Ile His Ser Leu Ser Gly Met
            100                 105                 110

Glu Ser Thr Val Leu Leu Ala Met Ala Phe Asp Arg Tyr Val Ala Ile
        115                 120                 125

Cys His Pro Leu Arg His Ala Thr Val Leu Thr Leu Pro Arg Val Thr
    130                 135                 140

Lys Ile Gly Val Ala Ala Val Val Arg Gly Ala Ala Leu Met Ala Pro
145                 150                 155                 160

Leu Pro Val Phe Ile Lys Gln Leu Pro Phe Cys Arg Ser Asn Ile Leu
                165                 170                 175

Ser His Ser Tyr Cys Leu His Gln Asp Val Met Lys Leu Ala Cys Asp
            180                 185                 190

Asp Ile Arg Val Asn Val Val Tyr Gly Leu Ile Val Ile Ile Ser Ala
        195                 200                 205

Ile Gly Leu Asp Ser Leu Leu Ile Ser Phe Ser Tyr Leu Leu Ile Leu
    210                 215                 220

Lys Thr Val Leu Gly Leu Thr Arg Glu Ala Gln Ala Lys Ala Phe Gly
225                 230                 235                 240

Thr Cys Val Ser His Val Cys Ala Val Phe Ile Phe Tyr Val Pro Phe
                245                 250                 255

Ile Gly Leu Ser Met Val His Arg Phe Ser Lys Arg Arg Asp Ser Pro
            260                 265                 270

Leu Pro Val Ile Leu Ala Asn Ile Tyr Leu Leu Val Pro Pro Val Leu
        275                 280                 285

Asn Pro Ile Val Tyr Gly Val Lys Thr Lys Glu Ile Arg Gln Arg Ile
    290                 295                 300

Leu Arg Leu Phe His Val Ala Thr His Ala Ser Glu Pro
305                 310                 315
```

```
<210> SEQ ID NO 3
<211> LENGTH: 320
<212> TYPE: PRT
<213> ORGANISM: Rat Protein

<400> SEQUENCE: 3
```

| | | | | | | | | | | | | | | | |
|---|---|---|---|---|---|---|---|---|---|---|---|---|---|---|---|
| Met | Ser | Ser | Cys | Asn | Phe | Thr | His | Ala | Thr | Phe | Met | Leu | Ile | Gly | Ile |
| 1 | | | | 5 | | | | | 10 | | | | | 15 | |
| Pro | Gly | Leu | Glu | Glu | Ala | His | Phe | Trp | Phe | Gly | Phe | Pro | Leu | Leu | Ser |
| | | | 20 | | | | | 25 | | | | | 30 | | |
| Met | Tyr | Ala | Val | Ala | Leu | Phe | Gly | Asn | Cys | Ile | Val | Val | Phe | Ile | Val |
| | | 35 | | | | | 40 | | | | | 45 | | | |
| Arg | Thr | Glu | Arg | Ser | Leu | His | Ala | Pro | Met | Tyr | Leu | Phe | Leu | Cys | Met |
| | 50 | | | | | 55 | | | | | 60 | | | | |
| Leu | Ala | Ala | Ile | Asp | Leu | Ala | Leu | Ser | Thr | Ser | Thr | Met | Pro | Lys | Ile |
| 65 | | | | | 70 | | | | | 75 | | | | | 80 |
| Leu | Ala | Leu | Phe | Trp | Phe | Asp | Ser | Arg | Glu | Ile | Thr | Phe | Asp | Ala | Cys |
| | | | | 85 | | | | | 90 | | | | | 95 | |
| Leu | Ala | Gln | Met | Phe | Phe | Ile | His | Ala | Leu | Ser | Ala | Ile | Glu | Ser | Thr |
| | | | 100 | | | | | 105 | | | | | 110 | | |
| Ile | Leu | Leu | Ala | Met | Ala | Phe | Asp | Arg | Tyr | Val | Ala | Ile | Cys | His | Pro |
| | | 115 | | | | | 120 | | | | | 125 | | | |
| Leu | Arg | His | Ala | Ala | Val | Leu | Asn | Asn | Thr | Val | Thr | Val | Gln | Ile | Gly |
| | 130 | | | | | 135 | | | | | 140 | | | | |
| Met | Val | Ala | Leu | Val | Arg | Gly | Ser | Leu | Phe | Phe | Phe | Pro | Leu | Pro | Leu |
| 145 | | | | | 150 | | | | | 155 | | | | | 160 |
| Leu | Ile | Lys | Arg | Leu | Ala | Phe | Cys | His | Ser | Asn | Val | Leu | Ser | His | Ser |
| | | | | 165 | | | | | 170 | | | | | 175 | |
| Tyr | Cys | Val | His | Gln | Asp | Val | Met | Lys | Leu | Ala | Tyr | Thr | Asp | Thr | Leu |
| | | | 180 | | | | | 185 | | | | | 190 | | |
| Pro | Asn | Val | Val | Tyr | Gly | Leu | Thr | Ala | Ile | Leu | Leu | Val | Met | Gly | Val |
| | | 195 | | | | | 200 | | | | | 205 | | | |
| Asp | Val | Met | Phe | Ile | Ser | Leu | Ser | Tyr | Phe | Leu | Ile | Ile | Arg | Ala | Val |
| | 210 | | | | | 215 | | | | | 220 | | | | |
| Leu | Gln | Leu | Pro | Ser | Lys | Ser | Glu | Arg | Ala | Lys | Ala | Phe | Gly | Thr | Cys |
| 225 | | | | | 230 | | | | | 235 | | | | | 240 |
| Val | Ser | His | Ile | Gly | Val | Val | Leu | Ala | Phe | Tyr | Val | Pro | Leu | Ile | Gly |
| | | | | 245 | | | | | 250 | | | | | 255 | |
| Leu | Ser | Val | Val | His | Arg | Phe | Gly | Asn | Ser | Leu | Asp | Pro | Ile | Val | His |
| | | | 260 | | | | | 265 | | | | | 270 | | |
| Val | Leu | Met | Gly | Asp | Val | Tyr | Leu | Leu | Leu | Pro | Pro | Val | Ile | Asn | Pro |
| | | 275 | | | | | 280 | | | | | 285 | | | |
| Ile | Ile | Tyr | Gly | Ala | Lys | Thr | Lys | Gln | Ile | Arg | Thr | Arg | Val | Leu | Ala |
| | 290 | | | | | 295 | | | | | 300 | | | | |
| Met | Phe | Lys | Ile | Ser | Cys | Asp | Lys | Asp | Ile | Glu | Ala | Gly | Gly | Asn | Thr |
| 305 | | | | | 310 | | | | | 315 | | | | | 320 |

```
<210> SEQ ID NO 4
<211> LENGTH: 320
<212> TYPE: PRT
<213> ORGANISM: Homo Sapiens

<400> SEQUENCE: 4
```

| | | | | | | | | | | | | | | | |
|---|---|---|---|---|---|---|---|---|---|---|---|---|---|---|---|
| Met | Ser | Ser | Cys | Asn | Phe | Thr | His | Ala | Thr | Cys | Val | Leu | Ile | Gly | Ile |
| 1 | | | | 5 | | | | | 10 | | | | | 15 | |

```
Pro Gly Leu Glu Lys Ala His Phe Trp Val Gly Phe Pro Leu Leu Ser
         20                  25                  30

Met Tyr Val Ala Met Cys Gly Asn Cys Ile Val Phe Ile Val
         35                  40                  45

Arg Thr Glu Arg Ser Leu His Ala Pro Met Tyr Leu Phe Leu Cys Met
     50                  55                  60

Leu Ala Ala Ile Asp Leu Ala Leu Ser Thr Thr Met Pro Lys Ile
 65                  70                  75                  80

Leu Ala Leu Phe Trp Phe Asp Ser Arg Glu Ile Ser Ile Glu Ala Cys
                 85                  90                  95

Leu Thr Gln Met Phe Phe Ile His Ala Leu Ser Ala Ile Glu Ser Thr
                100                 105                 110

Ile Leu Leu Ala Met Ala Phe Asp Arg Tyr Val Ala Ile Cys His Pro
            115                 120                 125

Leu Arg His Ala Ala Val Leu Asn Asn Thr Val Thr Ala Gln Ile Gly
        130                 135                 140

Ile Val Ala Val Val Arg Gly Ser Leu Phe Phe Pro Leu Pro Leu
145                 150                 155                 160

Leu Ile Lys Arg Leu Ala Phe Cys His Ser Asn Val Leu Ser His Ser
                165                 170                 175

Tyr Cys Val His Gln Asp Val Met Lys Leu Ala Tyr Ala Asp Thr Leu
                180                 185                 190

Pro Asn Val Val Tyr Gly Leu Thr Ala Ile Leu Val Met Gly Val
                195                 200                 205

Asp Val Met Phe Ile Ser Leu Ser Tyr Phe Leu Ile Ile Arg Thr Val
        210                 215                 220

Leu Gln Leu Pro Ser Lys Ser Glu Arg Ala Lys Ala Phe Gly Thr Cys
225                 230                 235                 240

Val Ser His Ile Gly Val Val Leu Ala Phe Tyr Val Pro Leu Ile Gly
                245                 250                 255

Leu Ser Val Val His Arg Phe Gly Asn Ser Leu His Pro Ile Val Arg
                260                 265                 270

Val Val Met Gly Asp Ile Tyr Leu Leu Leu Pro Pro Val Ile Asn Pro
            275                 280                 285

Ile Ile Tyr Gly Ala Lys Thr Lys Gln Ile Arg Thr Arg Val Leu Ala
        290                 295                 300

Met Phe Lys Ile Ser Cys Asp Lys Asp Leu Gln Ala Val Gly Gly Lys
305                 310                 315                 320

<210> SEQ ID NO 5
<211> LENGTH: 427
<212> TYPE: DNA
<213> ORGANISM: Homo Sapiens

<400> SEQUENCE: 5
gatcaaactt cttttccatt cagagtcctc tgattcagat tttaatgtta acattttgga    60
agacagtatt cagaaaaaaa atttccttaa taaaaataca actcagatcc ttcaaatatg   120
aaactggttg gggaatctcc attttttcaa tattattttc ttctttgttt tcttgctacg   180
tataattatt aatatcctga ctaggttgtg gttggagggt tattactttt cattttacca   240
tgcagtccaa atctaaactg cttctactga tggtttacag cattctgaga taagaatggt   300
acatctagag aacatttgcc aaaggcctaa gcacagcaaa ggaaaataaa cacagaatat   360
aataaaatga gataatctag cttaaaacta taacttcctc tttagaactc ccaaccacat   420
```

```
                                                    -continued ttggatc                                                         427

<210> SEQ ID NO 6
<211> LENGTH: 501
<212> TYPE: DNA
<213> ORGANISM: Homo Sapiens
<220> FEATURE:
<221> NAME/KEY: CDS
<222> LOCATION: (1)...(501)

<400> SEQUENCE: 6 gct gtg gcc atg ttt att gga gtg ttg gat cta ttc ttt atc atc cta    48
Ala Val Ala Met Phe Ile Gly Val Leu Asp Leu Phe Phe Ile Ile Leu
 1               5                  10                  15 tct tat atc ttt atc ctt cag gca gtt cta caa ctc tcc tct cag gag    96
Ser Tyr Ile Phe Ile Leu Gln Ala Val Leu Gln Leu Ser Ser Gln Glu
             20                  25                  30 gcc cgc tac aaa gca ttt ggg aca tgt gtc tct cac ata ggt gcc atc   144
Ala Arg Tyr Lys Ala Phe Gly Thr Cys Val Ser His Ile Gly Ala Ile
         35                  40                  45 tta gcc ttc tac aca cct tca gtc atc tct tca gtc atg cac cgt gtg   192
Leu Ala Phe Tyr Thr Pro Ser Val Ile Ser Ser Val Met His Arg Val
     50                  55                  60 gcc cgc tgt gct gtg cca cac gtc cac att ctc ctc gcc aat ttc tat   240
Ala Arg Cys Ala Val Pro His Val His Ile Leu Leu Ala Asn Phe Tyr
 65                  70                  75                  80 ctg ctc ttc cca ccc atg gtc aat ccc atc atc tat ggc gtt aag acc   288
Leu Leu Phe Pro Pro Met Val Asn Pro Ile Ile Tyr Gly Val Lys Thr
                 85                  90                  95 aag cag atc cgt gac agt ctt ggg agt att cct gag aaa gga tgt gtg   336
Lys Gln Ile Arg Asp Ser Leu Gly Ser Ile Pro Glu Lys Gly Cys Val
            100                 105                 110 aat aga gag tga gga ata agt gga aaa aga gtg ggg ccc agt gaa tgc   384
Asn Arg Glu  *  Gly Ile Ser Gly Lys Arg Val Gly Pro Ser Glu Cys
        115                 120                 125 tgt agt ggg cca ggg ctg tgc tga gag tag atg ggt cct aga ctc cac   432
Cys Ser Gly Pro Gly Leu Cys  *  Glu  *  Met Gly Pro Arg Leu His
    130                 135                 140 gtt tag ttc ttt tct tgt att atg aaa aga ata aat gat gtc ctg aag   480
Val  *  Phe Phe Ser Cys Ile Met Lys Arg Ile Asn Asp Val Leu Lys
145                 150                 155 ctc aga aaa aaa aaa aaa aaa                                       501
Leu Arg Lys Lys Lys Lys Lys
                160

<210> SEQ ID NO 7
<211> LENGTH: 163
<212> TYPE: PRT
<213> ORGANISM: Homo Sapiens

<400> SEQUENCE: 7

Ala Val Ala Met Phe Ile Gly Val Leu Asp Leu Phe Phe Ile Ile Leu
 1               5                  10                  15

Ser Tyr Ile Phe Ile Leu Gln Ala Val Leu Gln Leu Ser Ser Gln Glu
             20                  25                  30

Ala Arg Tyr Lys Ala Phe Gly Thr Cys Val Ser His Ile Gly Ala Ile
         35                  40                  45

Leu Ala Phe Tyr Thr Pro Ser Val Ile Ser Ser Val Met His Arg Val
     50                  55                  60

Ala Arg Cys Ala Val Pro His Val His Ile Leu Leu Ala Asn Phe Tyr
 65                  70                  75                  80
```

-continued

```
Leu Leu Phe Pro Pro Met Val Asn Pro Ile Ile Tyr Gly Val Lys Thr
                85                  90                  95

Lys Gln Ile Arg Asp Ser Leu Gly Ser Ile Pro Glu Lys Gly Cys Val
            100                 105                 110

Asn Arg Glu Gly Ile Ser Gly Lys Arg Val Gly Pro Ser Glu Cys Cys
        115                 120                 125

Ser Gly Pro Gly Leu Cys Glu Met Gly Pro Arg Leu His Val Phe Phe
    130                 135                 140

Ser Cys Ile Met Lys Arg Ile Asn Asp Val Leu Lys Leu Arg Lys Lys
145                 150                 155                 160

Lys Lys Lys

<210> SEQ ID NO 8
<211> LENGTH: 14
<212> TYPE: PRT
<213> ORGANISM: Homo Sapiens

<400> SEQUENCE: 8

Met Val Asp Pro Asn Gly Asn Glu Ser Ser Ala Thr Tyr Phe
1               5                   10

<210> SEQ ID NO 9
<211> LENGTH: 13
<212> TYPE: PRT
<213> ORGANISM: Homo Sapiens

<400> SEQUENCE: 9

Val His Arg Phe Ser Lys Arg Arg Asp Ser Pro Leu Pro
1               5                   10

<210> SEQ ID NO 10
<211> LENGTH: 4
<212> TYPE: PRT
<213> ORGANISM: Homo Sapiens

<400> SEQUENCE: 10

Asn Glu Ser Ser
1

<210> SEQ ID NO 11
<211> LENGTH: 4
<212> TYPE: PRT
<213> ORGANISM: Homo Sapiens

<400> SEQUENCE: 11

Asn Leu Thr Ile
1

<210> SEQ ID NO 12
<211> LENGTH: 4
<212> TYPE: PRT
<213> ORGANISM: Homo Sapiens

<400> SEQUENCE: 12

Asn Ser Thr Thr
1

<210> SEQ ID NO 13
<211> LENGTH: 4
<212> TYPE: PRT
<213> ORGANISM: Homo Sapiens
```

-continued

```
<400> SEQUENCE: 13

Arg Arg Asp Ser
1

<210> SEQ ID NO 14
<211> LENGTH: 4
<212> TYPE: PRT
<213> ORGANISM: Homo Sapiens

<400> SEQUENCE: 14

Ser Leu His Glu
1

<210> SEQ ID NO 15
<211> LENGTH: 4
<212> TYPE: PRT
<213> ORGANISM: Homo Sapiens

<400> SEQUENCE: 15

Ser Gly Ile Asp
1

<210> SEQ ID NO 16
<211> LENGTH: 4
<212> TYPE: PRT
<213> ORGANISM: Homo Sapiens

<400> SEQUENCE: 16

Ser Gly Met Glu
1

<210> SEQ ID NO 17
<211> LENGTH: 6
<212> TYPE: PRT
<213> ORGANISM: Homo Sapiens

<400> SEQUENCE: 17

Gly Asn Glu Ser Ser Ala
1               5

<210> SEQ ID NO 18
<211> LENGTH: 6
<212> TYPE: PRT
<213> ORGANISM: Homo Sapiens

<400> SEQUENCE: 18

Gly Leu Glu Glu Ala Gln
1               5

<210> SEQ ID NO 19
<211> LENGTH: 6
<212> TYPE: PRT
<213> ORGANISM: Homo Sapiens

<400> SEQUENCE: 19

Gly Met Glu Ser Thr Val
1               5

<210> SEQ ID NO 20
<211> LENGTH: 6
<212> TYPE: PRT
<213> ORGANISM: Homo Sapiens

<400> SEQUENCE: 20
```

```
Gly Thr Cys Val Ser His
 1               5
```

<210> SEQ ID NO 21
<211> LENGTH: 14
<212> TYPE: DNA
<213> ORGANISM: Artificial Sequence
<220> FEATURE:
<223> OTHER INFORMATION: Primer

<400> SEQUENCE: 21
ttttgatcaa gctt                                                       14

<210> SEQ ID NO 22
<211> LENGTH: 42
<212> TYPE: DNA
<213> ORGANISM: Artificial Sequence
<220> FEATURE:
<223> OTHER INFORMATION: Primer

<400> SEQUENCE: 22
ctaatacgac tcactatagg gctcgagcgg ccgcccgggc ag                         42

<210> SEQ ID NO 23
<211> LENGTH: 12
<212> TYPE: DNA
<213> ORGANISM: Artificial Sequence
<220> FEATURE:
<223> OTHER INFORMATION: Primer

<400> SEQUENCE: 23
ggcccgtcct ag                                                         12

<210> SEQ ID NO 24
<211> LENGTH: 40
<212> TYPE: DNA
<213> ORGANISM: Artificial Sequence
<220> FEATURE:
<223> OTHER INFORMATION: Primer

<400> SEQUENCE: 24
gtaatacgac tcactatagg gcagcgtggt cgcggccgag                            40

<210> SEQ ID NO 25
<211> LENGTH: 10
<212> TYPE: DNA
<213> ORGANISM: Artificial Sequence
<220> FEATURE:
<223> OTHER INFORMATION: Primer

<400> SEQUENCE: 25
cggctcctag                                                            10

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
ctaatacgac tcactatagg gc                                              22

<210> SEQ ID NO 27
<211> LENGTH: 22
<212> TYPE: DNA

```
<213> ORGANISM: Artificial Sequence
<220> FEATURE:
<223> OTHER INFORMATION: Primer

<400> SEQUENCE: 27
tcgagcggcc gcccgggcag ga                                      22

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
agcgtggtcg cggccgagga                                         20

<210> SEQ ID NO 29
<211> LENGTH: 25
<212> TYPE: DNA
<213> ORGANISM: Artificial Sequence
<220> FEATURE:
<223> OTHER INFORMATION: Primer

<400> SEQUENCE: 29
atatcgccgc gctcgtcgtc gacaa                                   25

<210> SEQ ID NO 30
<211> LENGTH: 26
<212> TYPE: DNA
<213> ORGANISM: Artificial Sequence
<220> FEATURE:
<223> OTHER INFORMATION: Primer

<400> SEQUENCE: 30
agccacacgc agctcattgt agaagg                                  26

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31
atcctgacta ggttgtggtt ggag                                    24

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
tgtggttggg agttctaaag agga                                    24

<210> SEQ ID NO 33
<211> LENGTH: 24
<212> TYPE: DNA
<213> ORGANISM: Artificial Sequence
<220> FEATURE:
<223> OTHER INFORMATION: FLAG tag

<400> SEQUENCE: 33
gattacaagg atgacgacga taag                                    24
```

<210> SEQ ID NO 34
<211> LENGTH: 27
<212> TYPE: DNA
<213> ORGANISM: Artificial Sequence
<220> FEATURE:
<223> OTHER INFORMATION: Primer

<400> SEQUENCE: 34
ccgaattcca tcttctggtt caatttc                                27

<210> SEQ ID NO 35
<211> LENGTH: 29
<212> TYPE: DNA
<213> ORGANISM: Artificial Sequence
<220> FEATURE:
<223> OTHER INFORMATION: Primer

<400> SEQUENCE: 35
cctctcgagt tcacatggaa aagtcgaag                              29

<210> SEQ ID NO 36
<211> LENGTH: 7
<212> TYPE: PRT
<213> ORGANISM: Homo Sapiens

<400> SEQUENCE: 36

Ser Leu His Glu Pro Met Tyr
1               5

<210> SEQ ID NO 37
<211> LENGTH: 7
<212> TYPE: PRT
<213> ORGANISM: Homo Sapiens

<400> SEQUENCE: 37

Ala Met Ala Phe Asp Arg Tyr
1               5

<210> SEQ ID NO 38
<211> LENGTH: 7
<212> TYPE: PRT
<213> ORGANISM: Homo Sapiens

<400> SEQUENCE: 38

Tyr Val Ala Ile Cys His Pro
1               5

<210> SEQ ID NO 39
<211> LENGTH: 7
<212> TYPE: PRT
<213> ORGANISM: Homo Sapiens

<400> SEQUENCE: 39

Lys Ala Phe Gly Thr Cys Val
1               5

<210> SEQ ID NO 40
<211> LENGTH: 7
<212> TYPE: PRT
<213> ORGANISM: Homo Sapiens

<400> SEQUENCE: 40

Gly Val Lys Thr Lys Glu Ile
1               5

<210> SEQ ID NO 41
<211> LENGTH: 21
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(21)
<223> OTHER INFORMATION: n = A,T,C or G

<400> SEQUENCE: 41
agyctncays mnccnatgta y                                              21

<210> SEQ ID NO 42
<211> LENGTH: 21
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(21)
<223> OTHER INFORMATION: n = A,T,C or G

<400> SEQUENCE: 42
tcnctncays mnccnatgta y                                              21

<210> SEQ ID NO 43
<211> LENGTH: 21
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(21)
<223> OTHER INFORMATION: n = A,T,C or G

<400> SEQUENCE: 43
agyttrcays mnccnatgta y                                              21

<210> SEQ ID NO 44
<211> LENGTH: 21
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(21)
<223> OTHER INFORMATION: n = A,T,C or G

<400> SEQUENCE: 44
tcnttrcays mnccnatgta y                                              21

<210> SEQ ID NO 45
<211> LENGTH: 21
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(21)
<223> OTHER INFORMATION: n = A,T,C or G

<400> SEQUENCE: 45
gcnatggcnt tygaycgnta y                                              21

<210> SEQ ID NO 46
<211> LENGTH: 21

```
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(21)
<223> OTHER INFORMATION: n = A,T,C or G

<400> SEQUENCE: 46
gcnatggcnt tygayagrta y                                      21

<210> SEQ ID NO 47
<211> LENGTH: 21
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(21)
<223> OTHER INFORMATION: n = A,T,C or G

<400> SEQUENCE: 47
taygtngcna thtgycaycc n                                      21

<210> SEQ ID NO 48
<211> LENGTH: 21
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(21)
<223> OTHER INFORMATION: n = A,T,C or G

<400> SEQUENCE: 48
nggrtgrcad atngcnacrt a                                      21

<210> SEQ ID NO 49
<211> LENGTH: 21
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(21)
<223> OTHER INFORMATION: n = A,T,C or G

<400> SEQUENCE: 49
nacrcangtn ccraangcyt t                                      21

<210> SEQ ID NO 50
<211> LENGTH: 21
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(21)
<223> OTHER INFORMATION: n = A,T,C or G

<400> SEQUENCE: 50
datytsyttn gtyttnrcnc c                                      21
```